US009944607B2

(12) United States Patent
Vincent et al.

(10) Patent No.: US 9,944,607 B2
(45) Date of Patent: Apr. 17, 2018

(54) THIOHYDANTOIN DERIVATIVES AND USES THEREOF

(71) Applicants: Whitehead Institute for Biomedical Research, Cambridge, MA (US); Massachusetts Institute of Technology, Cambridge, MA (US); The Broad Institute, Inc., Cambridge, MA (US)

(72) Inventors: Benjamin Vincent, Cambridge, MA (US); Luke Whitesell, Somerville, MA (US); Susan L. Lindquist, Cambridge, MA (US); Willmen Youngsaye, Cumberland, RI (US); Stephen L. Buchwald, Newton, MA (US); Jean-Baptiste Langlois, Sierentz (FR); Jun Pu, Shrewsbury, MA (US); Benito Munoz, Newtonville, MA (US); Sivaraman Dandapani, Malden, MA (US)

(73) Assignees: Whitehead Institute for Biomedical Research, Cambridge, MA (US); Massachusetts Institute of Technology, Cambridge, MA (US); The Broad Institute, Inc., Cambridge, MA (US)

( * ) Notice: Subject to any disclaimer, the term of this patent is extended or adjusted under 35 U.S.C. 154(b) by 0 days.

(21) Appl. No.: 14/435,790

(22) PCT Filed: Oct. 16, 2013

(86) PCT No.: PCT/US2013/065322
§ 371 (c)(1),
(2) Date: Apr. 15, 2015

(87) PCT Pub. No.: WO2014/062852
PCT Pub. Date: Apr. 24, 2014

(65) Prior Publication Data
US 2015/0259298 A1  Sep. 17, 2015

Related U.S. Application Data

(60) Provisional application No. 61/714,583, filed on Oct. 16, 2012.

(51) Int. Cl.
| | | |
|---|---|---|
| C07D 235/02 | (2006.01) |
| C07D 233/86 | (2006.01) |
| C07D 491/052 | (2006.01) |
| A01N 43/52 | (2006.01) |
| A01N 43/653 | (2006.01) |
| A01N 43/90 | (2006.01) |
| A01N 47/20 | (2006.01) |
| A61K 31/4184 | (2006.01) |
| A61K 31/4188 | (2006.01) |
| A61K 31/4196 | (2006.01) |
| C07D 491/107 | (2006.01) |
| C12Q 1/18 | (2006.01) |

(52) U.S. Cl.
CPC .......... *C07D 235/02* (2013.01); *A01N 43/52* (2013.01); *A01N 43/653* (2013.01); *A01N 43/90* (2013.01); *A01N 47/20* (2013.01); *A61K 31/4184* (2013.01); *A61K 31/4188* (2013.01); *A61K 31/4196* (2013.01); *C07D 233/86* (2013.01); *C07D 491/052* (2013.01); *C07D 491/107* (2013.01); *C12Q 1/18* (2013.01); *G01N 2333/395* (2013.01); *G01N 2333/40* (2013.01)

(58) Field of Classification Search
USPC .......................................... 514/3.7, 278, 383
See application file for complete search history.

(56) References Cited

U.S. PATENT DOCUMENTS

| | | | | |
|---|---|---|---|---|
| 3,755,350 A | * | 8/1973 | Sauli .................... | C07D 233/72 548/318.5 |
| 5,187,172 A | | 2/1993 | Austin | |
| 2009/0163545 A1 | | 6/2009 | Goldfarb | |

FOREIGN PATENT DOCUMENTS

| | | |
|---|---|---|
| RU | 2448096 C2 | 4/2012 |
| RU | 2449993 C2 | 5/2012 |
| WO | WO 2011/029392 A1 | 3/2011 |

OTHER PUBLICATIONS

International Search Report and Written Opinion, dated Apr. 24, 2014, in connection with Application No. PCT/US2013/065322.
International Preliminary Report on Patentability, dated Apr. 30, 2015, in connection with Application No. PCT/US2013/065322.

(Continued)

*Primary Examiner* — Pancham Bakshi
(74) *Attorney, Agent, or Firm* — Wolf, Greenfield & Sacks, P.C.

(57) ABSTRACT

The present invention provides novel compounds (e.g., compounds of Formula (I)), and pharmaceutically acceptable salts, solvates, hydrate, polymorphs, co-crystals, tautomers, stereoisomers, isotopically labeled derivatives, prodrugs, and compositions thereof. Also provided are methods and kits comprising the inventive Compounds, or compositions thereof, for treating and/or preventing a fungal or protozoan infection, inhibiting the activity of a fungal or protozoan enzyme, killing a fungus or protozoan, or inhibiting the growth of a fungus or protozoan. The fungus may be a *Candida* species, *Sacchawmyces* species, or other pathogenic fungal species. The compounds of the invention may inhibit the activity of fungal or protozoan mitochondrial phosphate carrier protein.

16 Claims, 15 Drawing Sheets

(56) References Cited

OTHER PUBLICATIONS

Genbank Submission; NIH/NCBI, Accession No. NP_002626.1. Palmieri, Mar. 15, 2015. 3 pages.
Genbank Submission; NIH/NCBI, Accession No. NP_005879.1. Palmieri, Mar. 15, 2015. 4 pages.
Genbank Submission; NIH/NCBI, Accession No. NP_010973.3. Dietrich et al., Jun. 14, 2015. 2 pages.
Genbank Submission; NIH/NCBI, Accession No. NP_012611.1. Goffeau et al., Jun. 14, 2015. 2 pages.
Genbank Submission; NIH/NCBI, Accession No. NP_998776.1. Palmieri, Mar. 15, 2015. 3 pages.
Genbank Submission; NIH/NCBI, Accession No. XP_001268724.1. Nierman, Feb. 21, 2008. 2 pages.
Genbank Submission; NIH/NCBI, Accession No. XP_002373347.1. Nierman, Jan. 19, 2010. 2 pages.
Genbank Submission; NIH/NCBI, Accession No. XP_003191325.1. D'Souza et al., Jul. 7, 2011. 2 pages.
Genbank Submission; NIH/NCBI, Accession No. XP_568892.1. Loftus et al., Aug. 17, 2012. 2 pages.
Genbank Submission; NIH/NCBI, Accession No. XP_723379.1. Jones et al., May 28, 2008. 2 pages.
Genbank Submission; NIH/NCBI, Accession No. XP_752883.1. Nierman et al., Feb. 19, 2008. 2 pages.
[No Author Listed], RN 103155-60-8. STN on the Web, Database CA. Jul. 12, 1986. 1 page.
[No Author Listed], RN 352224-98-7, 352224-96-5, 352224-95-4, 352224-94-3, 352224-932, 352224-92-1, 352224-91-0, 352224-90-9. STN on the Web, Database Chemical Library. Aug. 21, 2001.4 pages.
[No Author Listed], RN 443315-22-8, 443315-19-3, 443315-16-0, 443315-13-7. STN on the Web, Database CA, Chemical Library. Aug. 9, 2002. 3 pages.
[No Author Listed], RN 444151-20-6, 444150-67-8. STN on the Web, Database Chemical Library. Aug. 19, 2002. 1 page.
[No Author Listed], RN 489434-38-0, 489434-37-9, 489434-36-8, 489434-35-7. STN on the Web, Database CA, Chemical Library. Feb. 13, 2003. 2 pages.
[No Author Listed], RN 503561-04-4. STN on the Web, Database Chemical Library. Apr. 21, 2003. 1 page.
Abuhatab et al., Respiration deficiency in the pathogenic yeast, Candida albicans. Biochem Soc Trans. Feb. 1992;20(1):635.
Aoki et al., Induction of petite mutation with acriflavine and elevated temperature in Candida albicans. J Med Vet Mycol. Aug. 1987;25(4):269-77.
Becker et al., Pathway analysis of Candida albicans survival and virulence determinants in a murine infection model. Proc Natl Acad Sci U S A. Dec. 21, 2010;107(51):22044-9. doi: 10.1073/pnas. 1009845107. Epub Dec. 6, 2010.
Berge et al., Pharmaceutical Salts. J Pharm Sci. Jan. 1977;68(1):1-19.
Bouchara et al., In-vivo selection of an azole-resistant petite mutant of Candida glabrata. J Med Microbiol. Nov. 2000;49(11):977-84.
Brun et al., Biological consequences of petite mutations in Candida glabrata. J Antimicrob Chemother. Aug. 2005;56(2):307-14. Epub Jun. 15, 2005.
Cheng et al., A Candida albicans petite mutant strain with uncoupled oxidative phosphorylation overexpresses MDR1 and has diminished susceptibility to fluconazole and voriconazole. Antimicrob Agents Chemother. May 2007;51(5):1855-8. Epub Feb. 26, 2007.
Cheng et al., Uncoupling of oxidative phosphorylation enables Candida albicans to resist killing by phagocytes and persist in tissue. Cell Microbiol. Feb. 2007;9(2):492-501. Epub Sep. 20, 2006.
Cowen et al., Harnessing Hsp90 function as a powerful, broadly effective therapeutic strategy for fungal infectious disease. Proc Natl Acad Sci U S A. Feb. 24, 2009;106(8):2818-23. doi: 10.1073/pnas. 0813394106. Epub Feb. 5, 2009.
Cowen, Hsp90 orchestrates stress response signaling governing fungal drug resistance. PLoS Pathog. Aug. 2009;5(8):e1000471. doi: 10.1371/journal.ppat.1000471. Epub Aug. 28, 2009. 3 pages.
Ferrari et al., Gain of function mutations in CgPDR1 of Candida glabrata not only mediate antifungal resistance but also enhance virulence. PLoS Pathog. Jan. 2009;5(1):e1000268. doi: 10.1371/journal.ppat.1000268. Epub Jan. 16, 2009. 17 pages.
Ferrari et al., Loss of mitochondrial functions associated with azole resistance in Candida glabrata results in enhanced virulence in mice. Antimicrob Agents Chemother. May 2011;55(5):1852-60. doi: 10.1128/AAC.01271-10. Epub Feb. 14, 2011.
Gutierrez-Cirlos et al., Inhibition of the yeast cytochrome bc1 complex by ilicicolin H, a novel inhibitor that acts at the Qn site of the bc1 complex. J Biol Chem. Mar. 5, 2004;279(10):870814. Epub Dec. 10, 2003.
Hayakawa et al., The ilicicolins, antibiotics from Cylindrocladium ilicicola. J Antibiot (Tokyo). Sep. 1971;24(9):653-4.
Liu et al., A new method for the synthesis of 1,4,5-oxadiazocines and its application in the structure modification of natural products. Tetrahedron Lett. 2005;46(46):8009-12.
Martins et al., Classical and alternative components of the mitochondrial respiratory chain in pathogenic fungi as potential therapeutic targets. J Bioenerg Biomembr. Feb. 2011;43(1):81-8. doi: 10.1007/s10863-011-9331-1. Review.
Mathre et al., Mode of action of oxathiin systemic fungicides. III. Effect on mitochondrial activities. Pest Biochem Physiol. 1971;1(2):216-24.
Okamoto et al., Mitochondrial morphology and dynamics in yeast and multicellular eukaryotes. Annu Rev Genet. 2005;39:503-36. Review.
Pfaller et al., Epidemiology of invasive candidiasis: a persistent public health problem. Clin Microbiol Rev. Jan. 2007;20(1):133-63. Review.
Redding et al., Resistance of Candida albicans to fluconazole during treatment of oropharyngeal candidiasis in a patient with AIDS: documentation by in vitro susceptibility testing and DNA subtype analysis. Clin Infect Dis. Feb. 1994;18(2):240-2.
Robbins et al., Metabolic control of antifungal drug resistance. Fungal Genet Biol. Feb. 2010;47(2):81-93. doi: 10.1016/j.fgb.2009. 07.004. Epub Jul. 10, 2009.
Rotsaert et al., Differential efficacy of inhibition of mitochondrial and bacterial cytochrome bc1 complexes by center N inhibitors antimycin, ilicicolin H and funiculosin. Biochim Biophys Acta. Feb. 2008;1777(2):211-9. Epub Nov. 1, 2007.
Shingu-Vazquez et al., Mitochondria and fungal pathogenesis: drug tolerance, virulence, and potential for antifungal therapy. Eukaryot Cell. Nov. 2011;10(11):1376-83. doi: 10.1128/EC.05184-11. Epub Sep. 16, 2011. Review.
Singh et al., Biotransformation of antifungal ilicicolin H. Tetrahedron Lett. 2011;52(46):6190-1.
Sridhara et al., Synthesis, Antimicrobial and Cytotoxicity Studies of Some Novel Phthalazine-Methoxyacrylate Derivatives. J Pharm Res. 2011;4(2):496-500.
Ueki et al., Antifungal Inhibitors of Mitochondrial Respiration: Discovery and Prospects for Development. Curr Opin Anti-Infective Invest Drugs. Jan. 1, 2000;2(4):387-98.
Von Jagow et al., Use of specific inhibitors on the mitochondrial bc1 complex. Methods Enzymol. 1986;126:253-71.
Williams et al., Total synthesis of (.+-.)-ilicicolin H. J Org Chem. 1985;50(15):2807-9.
Zara et al., Yeast Mitochondria Lacking the Phosphate Carrier/p32 are Blocked in Phosphate Transport but Can Import Preproteins after Regeneration of a Membrane Potential. Molec Cell Biol. Nov. 1996;16(11):6524-31.

* cited by examiner ilicicolin H (1)

antimycin (2)

funiculosin (3)

I-A-1 (CID3889161)

■ BRD-K97464451-001-02-7

I-A-1 (CID3889161)

■ BRD-K97464451-001-02-7

MIR1

```
S. Cerevisiae    GFTPILFKQIPYNIAKF
C. Glabrata      GFTPILFKQIPYNIAKF
C. Albicans      GFTPILFKQIPYNIAKF
C. albicans-R    GFTPILFKQIPYTIAKF
C. Neoformans    GFGPILFKQVPYTMAKF
H. Sapiens        GVAPLWRQIPYTMMKF
```

THIOHYDANTOIN DERIVATIVES AND USES THEREOF

RELATED APPLICATIONS

This application is a national stage filing under 35 U.S.C. § 371 of international PCT application, PCT/US2013/065322, filed Oct. 16, 2013, which claims priority under 35 U.S.C. § 119(e) to U.S. Provisional Patent Application U.S. Ser. No. 61/714,583, filed Oct. 16, 2012, each of which is incorporated herein by reference.

GOVERNMENT SUPPORT

This invention was made with government support under grant numbers AI087879, GM106409, GM100518, GM 046059, and GM 058160 awarded by the National Institutes of Health (NIH). The government has certain rights in this invention.

BACKGROUND OF THE INVENTION

Intrinsic and acquired drug resistance by medically relevant microorganisms poses a grave threat to human health and has enormous economic consequences. Fungi are a prominent cause of hospital-acquired infections that is becoming increasingly difficult to control (Pfaller et al., Clin. Microbiol. Rev. 2007, 20:133-163). Fungal pathogens present a particular challenge because they are eukaryotes and share many of the same mechanisms that support the growth and survival of the human host cells they infect. The number of drug classes that have distinct targets in fungi is very limited and the usefulness of current antifungal drugs is compromised by either dose-limiting host toxicity or the frequent emergence of high-grade resistance. New, non-cross-reactive targets for therapeutic intervention are urgently needed (Cowen et al., Proc. Natl. Acad. Sci. USA 2009, 106(8):2818-23).

A frequently overlooked issue in the search for new antifungal targets is that fungal pathogens face a diverse array of environmental challenges during the establishment of invasive infection within a host animal (Cowen et al., PLoS Pathog. 2009, 5(8):e1000471). These can include pH, thermal, and osmotic stresses, as well as the need to utilize alternative carbon sources for energy production (Becker et al., Proc. Natl. Acad. Sci. USA 2010, 107(51):22044-9; Robbins et al., Fungal Genet. Biol. 2010, 47(2):81-93). The role of glycolytic versus respiratory metabolism in supporting fungal virulence and drug-resistance remains unresolved, due in large part to the absence of good tools with which to tackle the question (Brun et al., J. Antimicrob. Chemother. 2005, 56:307-314; Cheng et al., Cell Microbiol. 2007, 9:492-501).

SUMMARY OF THE INVENTION

The role of glycolytic versus respiratory metabolism in supporting fungal virulence and drug-resistance have not been fully investigated due in large part to the lack of appropriate small molecule tool compounds that can reliably discriminate between these two metabolic pathways. A prior MLPCN (Molecular Libraries Probe Centers Network) project designed to identify compounds capable of chemosensitizing drug-resistant Candida albicans (C. albicans) clinical isolates to fluconazole (below) also uncovered compounds possessing potent single-agent activity against a range of opportunistic human fungal pathogens. Further experimentation determined their activity is dependent upon culture conditions that require mitochondrial respiratory metabolism for growth and survival. This subset of compounds were investigated as selective inhibitors of fungal respiration, and compounds of Formula (I) were identified that selectively inhibit the growth of fungi when they are cultured under conditions requiring mitochondrial respiration to support metabolic needs. These compounds, such as compound I-B-4 (ML316, CID56604860), are thiohydantoin derivatives and exhibit potent antifungal activity that can be modulated by replacing carbon source growth media. Compound I-B-4 (ML316) is of value in probing the metabolic requirements for fungal virulence and may provide essential leads for the development of new antifungal drugs.

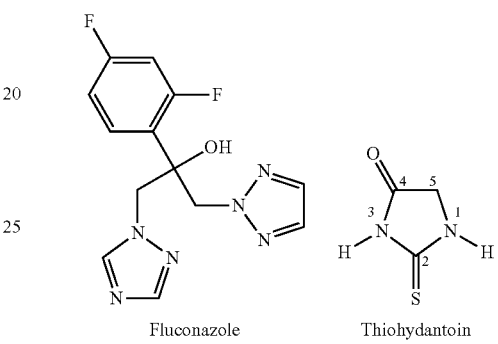

Fluconazole          Thiohydantoin

Certain compounds of Formula (I) (e.g., compound I-B-4 (ML316)) can reliably discriminate between glycolytic versus respiratory metabolism in supporting fungal virulence and growth. These compounds can be used in numerous types of research activities. For example, it can be evaluated in genetic studies using genome-wide over-expression and deletion libraries to define the modes of action in Saccharomyces cerevisiae (S. cerevisiae) assayed under fermentative versus respiratory growth conditions. To complement genetic approaches, affinity precipitation and proteomic approaches based on Stable Isotope Labeling with Amino acids in Cell culture (SILAC) technology may also be used for target identification. Further medicinal chemistry work on compounds of Formula (I) (e.g., compound I-B-4 (ML316)), including optimization of DMPK (drug metabolism and pharmacokinetics) properties, will enable studies in well-established mouse models of infection by drug-resistant fungal species, such as Candida glabrata (C. glabrata) and Candida albicans and potential clinical use in humans.

In one aspect, the present invention provides compounds developed from the identification of compound I-B-4 for treating fungal injections as described above.

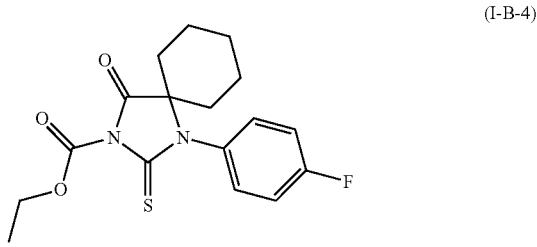 [SMILES: CCOC(=O)N1C(=O)C2(CCCCC2)N(c2ccc(F)cc2)C1=S]

(I-B-4)

In certain embodiments, the present invention provides compounds of Formula (I):

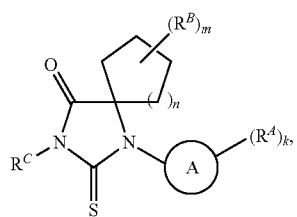
wherein Ring A, $R^A$, $R^B$, $R^C$, k, m, and n are defined herein, and pharmaceutically acceptable salts, solvates, hydrates, polymorphs, co-crystals, tautomers, stereoisomers, isotopically labeled derivatives, and prodrugs thereof.
Exemplary compounds of Formula (I) include, but are not limited to:
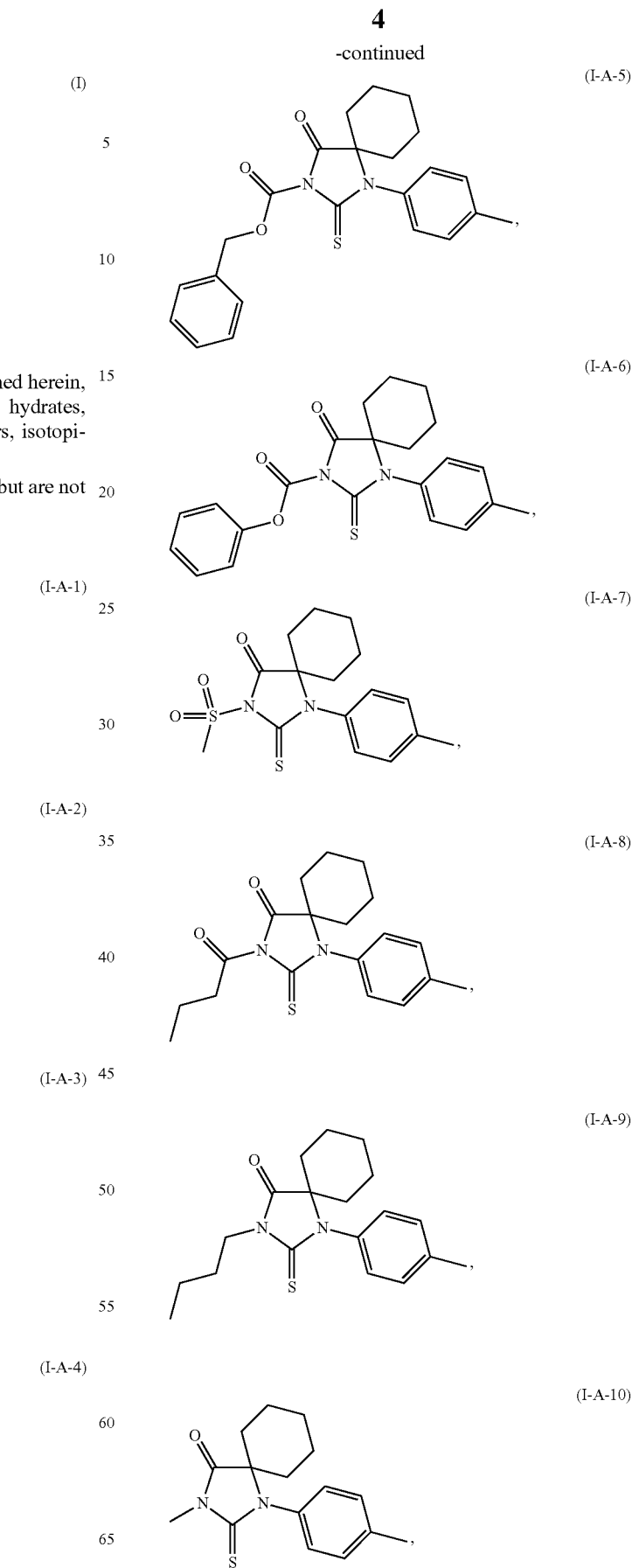

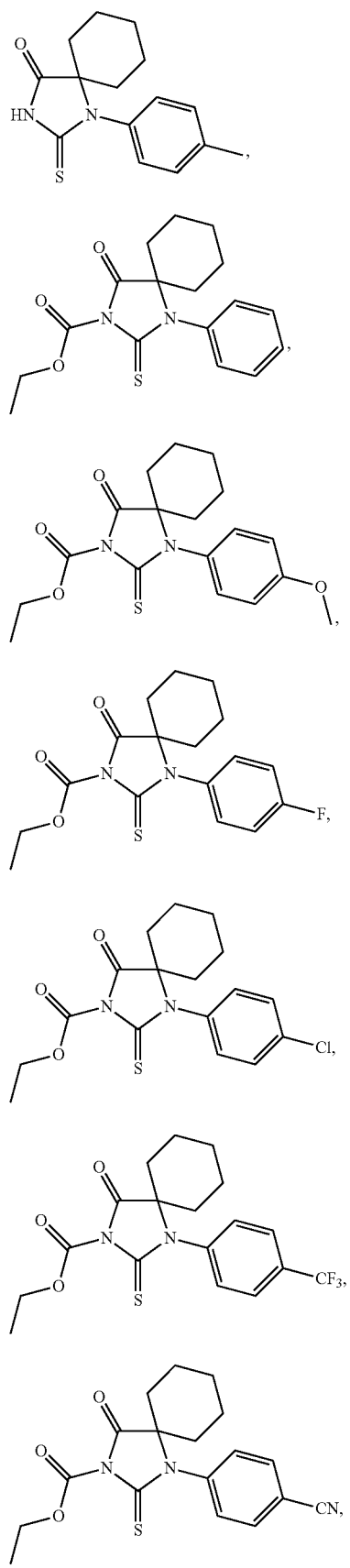
(I-A-11)
(I-B-2)
(I-B-3)
(I-B-4)
(I-B-5)
(I-B-6)
(I-B-7)
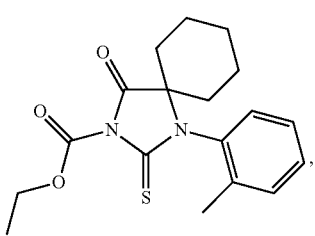
(I-B-8)
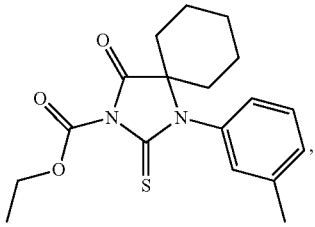
(I-B-9)
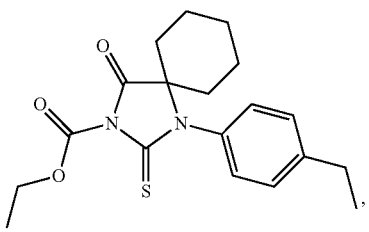
(I-B-10)
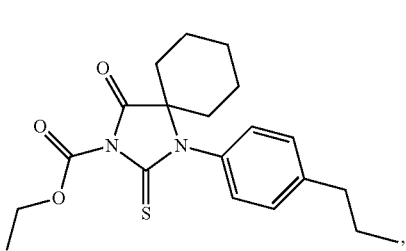
(I-B-11)
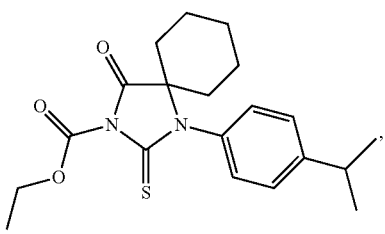
(I-B-12)
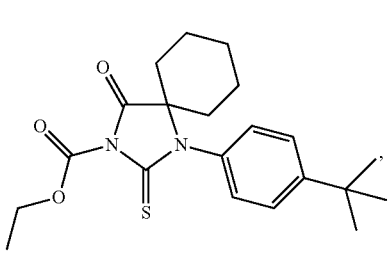
(I-B-13)

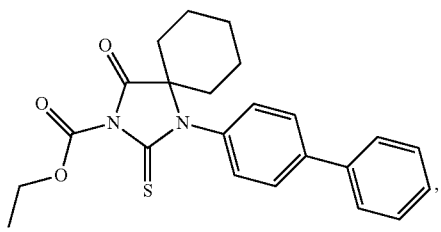

(I-B-14)

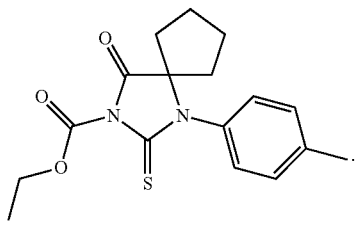

(I-C-3)

In another aspect, the present invention provides pharmaceutical compositions comprising a compound described herein (e.g., a compound of Formula (I)), or a pharmaceutically acceptable salt, solvate, hydrate, polymorph, co-crystal, tautomer, stereoisomer, isotopically labeled derivative, or prodrug thereof, and optionally a pharmaceutically acceptable excipient. In certain embodiments, the pharmaceutical compositions described herein include a therapeutically effective amount of a compound of described herein, or a pharmaceutically acceptable salt, solvate, hydrate, polymorph, co-crystal, tautomer, stereoisomer, isotopically labeled derivative, or prodrug thereof, for treating or preventing a fungal or protozoan infection. The pharmaceutical composition may optionally include another antifungal agent such as an azole antibiotic (e.g., fluconazole).

In one aspect, the present invention provides methods for the treatment of a fungal infection in a subject. In certain embodiments, the fungus causing the fungal infection is a *Candida* species (e.g., *Candida albicans* (e.g., CaCi-2 or CaCi-8)). In certain embodiments, the fungus is a *Saccharomyces* species (e.g., *Saccharomyces cerevisiae*). In certain embodiments, the fungus causing the fungal infection is resistant to an antifungal agent such as fluconazole.

In another aspect, the present invention provides methods for the treatment of a protozoan infection in a subject. In certain embodiments, the protozoon causing the protozoan infection is a *Cryptosporidium*. In certain embodiments, the protozoon causing the protozoan infection is a member of the genus *Trypanosoma*. In certain embodiments, the protozoon causing the protozoan infection is a member of the genus *Pneumocystis*. In certain embodiments, the protozoon causing the protozoan infection is a member of the genus *Plasmodium*. In certain embodiments, the protozoon causing the protozoan infection is a member of the genus *Giardia*.

In still another aspect, the present invention provides methods of inhibiting the activity of fungal and/or protozoan mitochondrial phosphate carrier protein in a subject or biological sample.

In some aspects, the disclosure provides the recognition that mitochondrial phosphate transport processes are useful as targets for antifungal or antiprotozoal agents. In some aspects, the disclosure provides the recognition that mitochondrial phosphate carrier protein (e.g., MIR1) is useful as a target for antifungal or antiprotozoal agents. In some aspects, the disclosure provides the recognition that agents that inhibit mitochondrial phosphate carrier protein (e.g., inhibitors of the expression or activity of mitochondrial phosphate carrier protein) are useful as antifungal or antiprotozoal agents.

Another aspect of the present invention relates to methods of killing a fungus and/or protozoon or inhibiting the growth of a fungus and/or protozoon. In certain embodiments, the methods described herein include administering to a subject, contacting a biological sample, or contacting a fungus and/or protozoon with an effective amount of a compound described herein, or a pharmaceutically acceptable salt, solvate, hydrate, polymorph, co-crystal, tautomer, stereoisomer, isotopically labeled derivative, or prodrug thereof, or a composition thereof. The inventive methods may be performed in vitro or in vivo.

The methods of the present invention may further comprise administering to a subject, contacting a biological sample, or contacting a fungus or protozoon, with one or more additional pharmaceutical agents in combination with a compound described herein, or a pharmaceutically acceptable salt, solvate, hydrate, polymorph, co-crystal, tautomer, stereoisomer, isotopically labeled derivative, or prodrug thereof, or a pharmaceutical composition thereof. The additional pharmaceutical agent may be an antifungal agent (e.g., an azole antifungal agent, such as fluconazole) and/or an antiprotozoan agent.

Another aspect of the invention relates to methods of screening a library of compounds to identify one or more compounds that are useful for the methods of the invention. In certain embodiments, the compound identified by the methods of screening is useful in killing a fungus and/or protozoon or inhibiting the growth of a fungus and/or protozoon when the compound is employed in the absence of one or more additional pharmaceutical agents. In certain embodiments, the compound identified by the methods of screening is useful in killing a fungus and/or protozoon or inhibiting the growth of a fungus and/or protozoon when employed in combination with one or more additional pharmaceutical agents.

In yet another aspect, the present invention provides the compounds described herein, and pharmaceutically acceptable salts, solvates, hydrates, polymorphs, co-crystals, tautomers, stereoisomers, isotopically labeled derivatives, prodrugs, and compositions thereof, for use in the treatment and/or prevention of a fungal and/or protozoan infection in a subject, or in the killing a fungus and/or protozoon or inhibiting the growth of a fungus and/or protozoon.

Another aspect provides methods of making compounds described herein, and methods of making compositions comprising one or more of the compounds described herein.

Another aspect of the present invention relates to kits comprising a container with a compound described herein, or a pharmaceutically acceptable salt, solvate, hydrate, polymorph, co-crystal, tautomer, stereoisomer, isotopically labeled derivative, or prodrug thereof, or a pharmaceutical composition thereof. The kits of the invention may include a single dose or multiple doses of a compound described herein, or a pharmaceutically acceptable salt, solvate, hydrate, polymorph, co-crystal, tautomer, stereoisomer, isotopically labeled derivative, or prodrug thereof, or a pharmaceutical composition thereof. The kits described herein may also include one or more additional pharmaceutical agents, such as antifungal agents (e.g., azole antifungal agents such as fluconazole) and antiprotozoan agents. The provided kits may be useful for the treatment and/or prevention of a fungal and/or protozoan infection. In certain embodiments, the kits described herein further include instructions for administering a compound described herein, or a pharmaceutically acceptable salt, solvate, hydrate, polymorph, co-crystal, tautomer, stereoisomer, isotopically labeled derivative, or prodrug thereof, or a pharmaceutical composition thereof.

The details of particular embodiments of the invention are set forth herein. Other features, objects, and advantages of the invention will be apparent from the Detailed Description, the Figures, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3}$-cycloalkyl groups include the aforementioned $C_{5}$-cycloalkyl groups as well as cyclopropyl ($C_3$) and cyclobutyl ($C_4$). Examples of $C_{3-8}$ cycloalkyl groups include the aforementioned $C_{3}$-cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl, as defined herein, and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 p electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl, as defined herein, and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, as defined herein, which are divalent bridging groups are further referred to using the suffix -ene, e.g., alkylene, alkenylene, alkynylene, carbocyclylene, heterocyclylene, arylene, and heteroarylene.

As used herein, the term "optionally substituted" refers to substituted or unsubstituted.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$ =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH (C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, C$^-$, Br$^-$, I$^-$), NO$_3^-$, ClO$_4^-$, OH$^-$, H$_2$PO$_4^-$, HSO$_4^-$, sulfonate ions (e.g., methanesulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Acyl" as used herein refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, Ru$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{cc}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$_{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O) SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$) N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O) (OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is an sulfur protecting group (also referred to as a thiol protecting group). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb}$, and $-P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

As used herein, the term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, -OTs), methanesulfonate (mesylate, -OMs), p-bromobenzenesulfonyloxy (brosylate, -OBs), or trifluoromethanesulfonate (triflate, -OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

These and other exemplary substituents are described in more detail in the Detailed Description, Figures, Examples, and Claims. The invention is not intended to be limited in any manner by the above exemplary listing of substituents.

Other Definitions

The following definitions are more general terms used throughout the present application:

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R·x H$_2$O, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates (R·0.5 H$_2$O)), and polyhydrates (x is a number greater than 1, e.g., dihydrates (R·2 H$_2$O) and hexahydrates (R·6 H$_2$O)).

The term "tautomers" refer to compounds that are interchangeable forms of a particular compound structure, and that vary in the displacement of hydrogen atoms and electrons. Thus, two structures may be in equilibrium through the movement of x electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds described herein, which have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is non-human animal. In certain embodiments, the animal is fish.

The terms "administer," "administering," or "administration," as used herein, refers to implanting, absorbing, ingesting, injecting, inhaling, or otherwise introducing an inventive compound, or a pharmaceutical composition thereof, in or on a subject.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein, such as a fungal or protozoan infection. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of exposure to a pathogen). Treatment may also be continued after symptoms have resolved, for example, to delay or prevent recurrence.

As used herein, the terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment. For example, in treating a fungal or protozoan infection, an effective amount of an inventive compound may inhibit the growth of the fungi and/or kill the fungi.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments, or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

A "protein" or "peptide" comprises a polymer of amino acid residues linked together by peptide bonds. The term, as used herein, refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The mitochondrial phosphate carrier protein or the mitochondrial phosphate transporter provides the inorganic phosphate for ATP synthase to couple to ADP. The yeast transporter is encoded by the MIR1 gene and is about 40% identical to the corresponding phosphate carrier protein in humans, which is encoded by the SLC25A3 gene. In yeast, the mutation associated with resistance to I-B-4 (ML316) is N184T. It will be understood that the precise sequence of MIR1 may vary in different isolates, strains, and species of fungi and protozoa. Representative sequences are provided under the NBCI accession numbers provided herein and are readily evident to those of ordinary skill in the art. Sequences of MIR1 homologs expressed in different fungal strains or protozoa may be identified by performing appropriate searches in publicly available databases using a provided sequence as a query sequence. In some embodiments a variant sequence comprising a sequence at least 80%, 85%, 90%, 95%, 96%, 97%, 98%, 99%, 99.5%, or more identical to a reference sequence may be used. It will be appreciated that recombinant proteins expressed in a cell, e.g., used in a method described herein, may be tagged with, for example, an epitope tag, if desired, in certain embodiments. It will also be understood that mammalian, e.g., human SLC25A3, has more than one isoform. Any isoform may be used in various embodiments. For example, human SLC25A3 isoform b may be used.

The following are Gene symbols, Gene ID, and representative mRNA and protein sequences for various exemplary mitochondrial phosphate carrier proteins:

Gene symbol MIR1: Saccharomyces cerevisiae strain S288c; NCBI Gene ID: 853540; NCBI RefSeq accession numbers: NM_001181735.1→NP_012611.1

Gene symbol MIR1: Candida albicans strain SC5314, Gene ID: 3635000; NCBI RefSeq accession numbers: XM_718286.1→XP_723379.1

Gene symbol AFUA_1G15140 Aspergillus fumigatus Af293, Gene ID: 3509906; NCBI RefSeq accession numbers: XM_747790.1→XP_752883.1

Gene symbol ACLA_020050 Aspergillus clavatus NRRL 1, Gene ID: 4700963; NCBI RefSeq accession numbers: XM_001268723.1→XP_001268724.1

Gene symbol AFLA_084330 Aspergillus flavus NRRL3357, Gene ID: 7910873; NCBI RefSeq accession numbers: XM_002373306.1→XP_002373347.1

Gene symbol CGB_A3210W Cryptococcus gattii WM276; Gene ID: 10188619; NCBI RefSeq accession numbers: XM_003191277.1→XP_003191325.1

Gene symbol CNB03150 Cryptococcus neoformans var. neoformans JEC21 Gene ID: 3256072; NCBI RefSeq accession numbers: XM_568892.1→XP_568892.1

Gene symbol SLC25A3 Homo sapiens, Gene ID: 5250; NCBI RefSeq accession numbers:

NM_002635.3→NP_002626.1 phosphate carrier protein, mitochondrial isoform b precursor. This transcript variant (variant 2) represents the predominant transcript. Variants 2 and 3 encode the same isoform (b);

NM_213611.2→NP_998776.1 phosphate carrier protein, mitochondrial isoform b precursor. This transcript variant (variant 3) differs in the 5' UTR, compared to variant 2. Variants 2 and 3 both encode isoform b;

NM_005888.3→NP_005879.1 phosphate carrier protein, mitochondrial isoform a precursor. This transcript variant (variant 1) has an alternate exon in the 5' coding region, compared to variant 2. It encodes isoform a, which has an internal segment that differs from isoform b.

The present application refers to various issued patent, published patent applications, journal articles, and other publications, all of which are incorporated herein by reference.

The details of one or more embodiments of the invention are set forth herein. Other features, objects, and advantages of the invention will be apparent from the Detailed Description, the Figures, the Examples, and the Claims.

DETAILED DESCRIPTION OF CERTAIN EMBODIMENTS OF THE INVENTION

Figure 1:
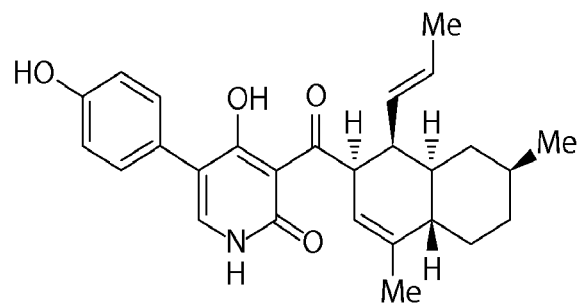
FIG. 1 shows some known inhibitors of fungal mitochondria oxidative phosphorylation. Ilicicolin H (1) has demonstrated 100-fold selectivity for fungal mitochondria in biochemical assays but displays moderate toxicity against HeLa cells. Antimycin (2) and funiculosin (3) are potent, but non-selective, inhibitors of mitochondrial function.
Figure 1:
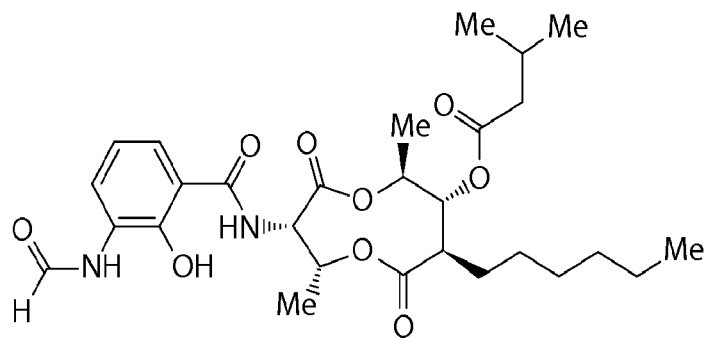
Figure 1:
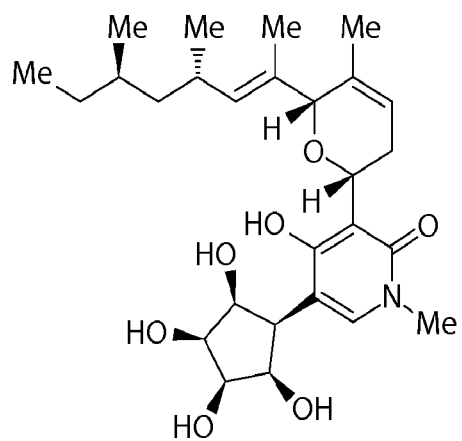

Provided herein are novel thiohydantoin derivatives and uses thereof. In one aspect, the present invention provides compounds described herein. In certain embodiments, the compounds are of Formula (I). These compounds have been found to be antifungal agents, antiprotozoan agents, and/or chemosensitizers capable of reversing the resistance of a fungus to an antifungal agent (e.g., fluconazole) and/or resistance of a protozoon to an antiprotozoan agent. Without wishing to be bound by any particular theory, the provided compounds may inhibit the activity of fungal mitochondrial phosphate carrier protein. The invention also provides pharmaceutical compositions and kits comprising the compounds described herein. Also provided are methods of using the compounds described herein (e.g., compounds of Formula (I)), to treat and/or prevent a fungal or protozoan infection, kill a fungus or protozoon, and/or inhibit the growth of a fungus or protozoon. In certain embodiments, the fungus described herein is a Candida species. In certain embodiments, the fungus described herein is a Saccharomyces species. In certain embodiments, the compounds described herein are used in the inventive methods in combination with one or more additional pharmaceutical agents (e.g., an antifungal agent (such as an azole antifungal agent such as fluconazole and/or antiprotozoan agent). In certain embodiments, the fungus or protozoon described herein is resistant to the additional antifungal agent.

Compounds

In one aspect of the present invention, the present invention provides compounds of Formula (I):

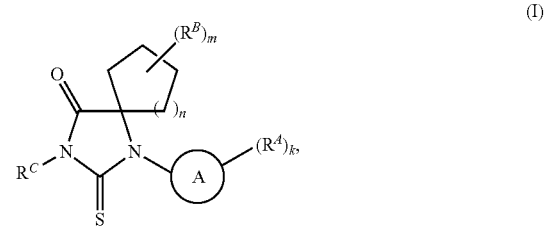

and pharmaceutically acceptable salts, solvates, hydrates, polymorphs, co-crystals, tautomers, stereoisomers, isotopically labeled derivatives, and prodrugs thereof;

wherein:

Ring A is a substituted or unsubstituted aryl ring, or substituted or unsubstituted heteroaryl ring;

each instance of $R^A$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{A1}$, —N(R$^{A1}$)$_2$, —SR$^{A1}$, —CN, —SCN, —C(=NR$^{A1}$)R$^{A1}$, —C(=NR$^{A1}$)OR$^{A1}$, —C(=NR$^{A1}$)N(R$^{A1}$)$_2$, —C(=O)R$^{A1}$, —C(=O)OR$^{A1}$, —C(=O)N(R$^{A1}$)$_2$, —NO$_2$, —NR$^{A1}$C(=O)R$^{A1}$, —NR$^{A1}$C(=O)OR$^{A1}$, NR$^{A1}$C(=O)N(R$^{A1}$)$_2$, —OC(=O)R$^{A1}$, —OC(=O)OR$^{A1}$, —OC(=O)N(R$^{A1}$)$_2$, or a nitrogen protecting group when attached to a nitrogen atom, or optionally two $R^A$ groups are joined to form a substituted or unsubstituted carbocyclic, substituted or unsubstituted heterocyclic, substituted or unsubstituted aryl, or substituted or unsubstituted heteroaryl ring;

each instance of $R^{A1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or optionally two $R^{A1}$ groups are joined to form a substituted or unsubstituted heterocyclic ring;

k is 0, 1, 2, 3, 4, or 5;

each instance of $R^B$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{B1}$, $-N(R^{B1})_2$, $-SR^{B1}$, $-CN$, $-SCN$, $-C(=NR^{B1})R^{B1}$, $-C(=NR^{B1})OR^{B1}$, $-C(=NR^{B1})N(R^{B1})_2$, $-C(=O)R^{B1}$, $-C(=O)OR^{B1}$, $-C(=O)N(R^{B1})_2$, $-NO_2$, $-NR^{B1}C(=O)R^{B1}$, $-NR^{B1}C(=O)OR^{B1}$, $-NR^{B1}C(=O)N(R^{B1})_2$, $-OC(=O)R^{B1}$, $-OC(=O)OR^{B1}$, or $-OC(=O)N(R^{B1})_2$, or optionally two $R^B$ groups are joined to form a substituted or unsubstituted carbocyclic, substituted or unsubstituted heterocyclic, substituted or unsubstituted aryl, or substituted or unsubstituted heteroaryl ring;

each instance of $R^{B1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or optionally two $R^{B1}$ groups are joined to form a substituted or unsubstituted heterocyclic ring;

m is 0, 1, 2, 3, 4, 5, 6, 7, 8, 9, or 10;

n is 1 or 2;

$R^C$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-C(=NR^{C1})R^{C1}$, $-C(=NR^{C1})OR^{C1}$, $-C(=NR^{C1})N(R^{C1})_2$, $-C(=O)R^{C1}$, $-C(=O)OR^{C1}$, $-C(=O)N(R^{C1})_2$, $-S(=O)R^{C1}$, $-S(=O)OR^{C1}$, $-S(=O)N(R^{C1})_2$, $-S(=O)_2R^{C1}$, $-S(=O)_2OR^{C1}$, $-S(=O)_2N(R^{C1})_2$, $-C(CN)=NOR^{C1}$, $-CF_2-R^{C1}$,

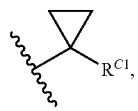

or a nitrogen protecting group; and each instance of $R^{C1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or an oxygen protecting group when attached to an oxygen atom, or optionally two $R^{C1}$ groups are joined to form a substituted or unsubstituted heterocyclic ring.

In certain embodiments, the present invention provides compounds of Formula (I), and pharmaceutically acceptable salts thereof.

Compounds of Formula (I) include a substituted or unsubstituted aryl ring, or substituted or unsubstituted heteroaryl ring as Ring A. In certain embodiments, Ring A is a substituted aryl ring. In certain embodiments, Ring A is an unsubstituted aryl ring. In certain embodiments, Ring A is a monocyclic aryl ring. In certain embodiments, Ring A is substituted phenyl. In certain embodiments, Ring A is of the formula:

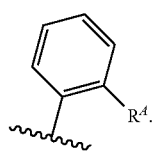

In certain embodiments, Ring A is of the formula:

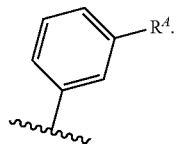

In certain embodiments, Ring A is of the formula:

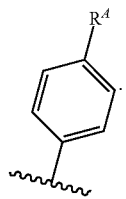

In certain embodiments, Ring A is of the formula

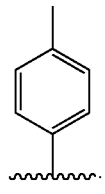

In certain embodiments, Ring A is of the formula:

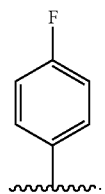

In certain embodiments, Ring A is of the formula:

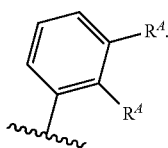

In certain embodiments, Ring A is the formula:

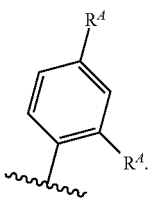

In certain embodiments, Ring A is of the formula:

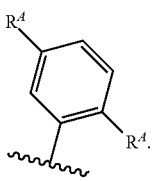

In certain embodiments, Ring A is of the formula:

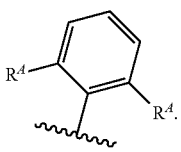

In certain embodiments, Ring A is of the formula:

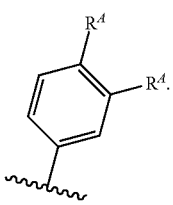

In certain embodiments, Ring A is of the formula:

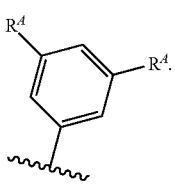

In certain embodiments, Ring A is unsubstituted phenyl. In certain embodiments, Ring A is a bicyclic aryl ring. In certain embodiments, Ring A is substituted naphthyl. In certain embodiments, Ring A is unsubstituted naphthyl. In certain embodiments, Ring A is a tricyclic aryl ring. In certain embodiments, Ring A is substituted anthracenyl. In certain embodiments, Ring A is unsubstituted anthracenyl. In certain embodiments, Ring A is an optionally substituted aryl ring fused with one or more optionally substituted carbocyclic, optionally substituted heterocyclic, optionally substituted aryl, or optionally substituted heteroaryl groups wherein the point of attachment is on the aryl ring.

Ring A of Formula (I) may also be an optionally substituted heteroaryl ring. In certain embodiments, Ring A is a substituted heteroaryl ring. In certain embodiments, Ring A is an unsubstituted heteroaryl ring. In certain embodiments, Ring A is a monocyclic heteroaryl ring. In certain embodiments, Ring A is a 6-membered monocyclic heteroaryl ring. In certain embodiments, Ring A is a 6-membered monocyclic heteroaryl ring, wherein only one of the six atoms in the ring of the heteroaryl is nitrogen. In certain embodiments, Ring A is of the formula:

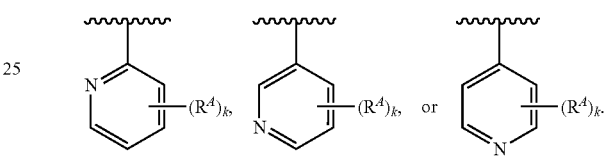

In certain embodiments, Ring A is a 6-membered monocyclic heteroaryl ring, wherein only two of the six atoms in the ring of the heteroaryl are nitrogen. In certain embodiments, Ring A is of the formula:

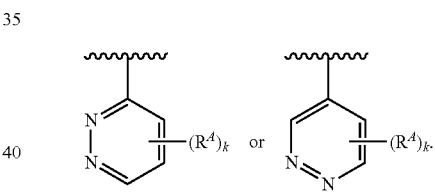

In certain embodiments, Ring A is of the formula:

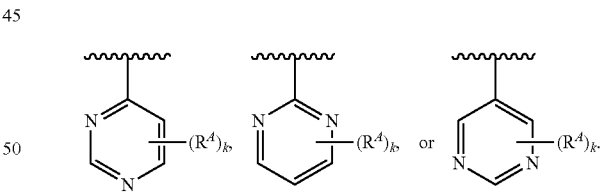

In certain embodiments, Ring A is of the formula:

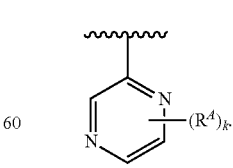

In certain embodiments, Ring A is a 6-membered monocyclic heteroaryl ring, wherein only three of the six atoms in the ring of the heteroaryl are nitrogen. In certain embodiments, Ring A is of the formula:

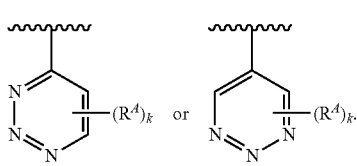

In certain embodiments, Ring A is of the formula:

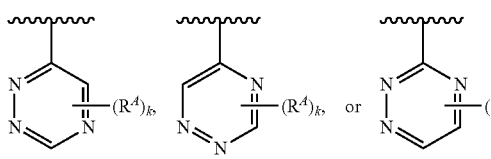

In certain embodiments, Ring A is of the formula:

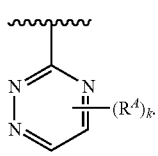

In certain embodiments, Ring A is a 5-membered monocyclic heteroaryl ring. In certain embodiments, Ring A is a 5-membered monocyclic heteroaryl ring, wherein only one of the five atoms in the ring of the heteroaryl is nitrogen, oxygen, or sulfur. In certain embodiments, Ring A is of the formula:

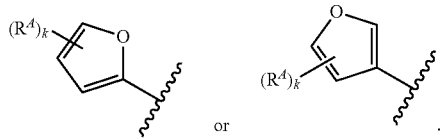

In certain embodiments, Ring A is of the formula:

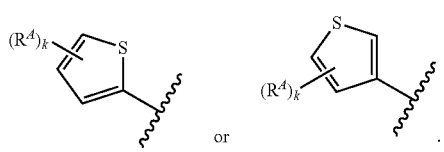

In certain embodiments, Ring A is of the formula:

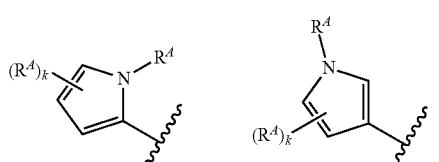

In certain embodiments, Ring A is a 5-membered monocyclic heteroaryl ring, wherein only two of the five atoms in the ring of the heteroaryl are independently nitrogen, oxygen, or sulfur. In certain embodiments, Ring A is of the formula:

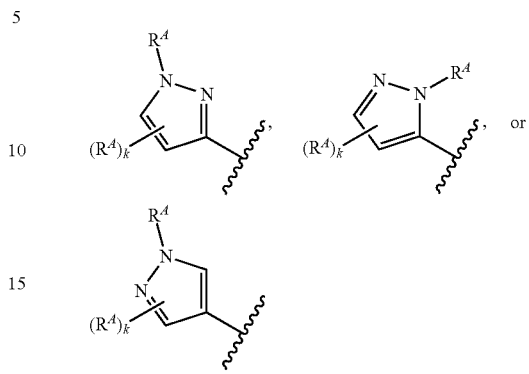

In certain embodiments, Ring A is of the formula:

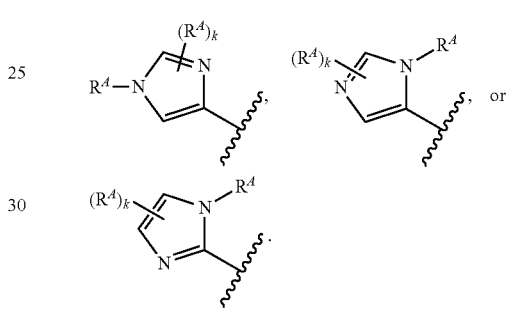

In certain embodiments, Ring A is of the formula:

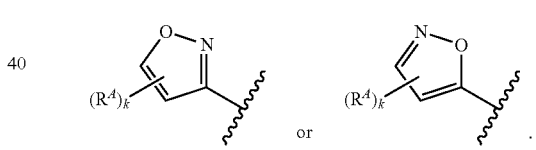

In certain embodiments, Ring A is of the formula:

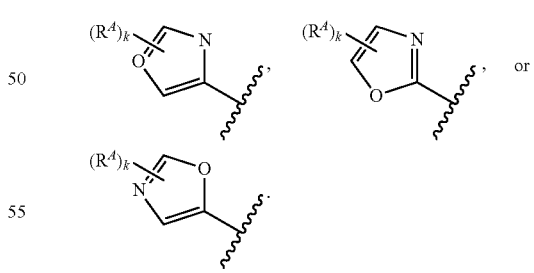

In certain embodiments, Ring A is of the formula:

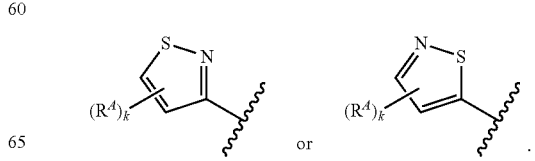

In certain embodiments, Ring A is of the formula:

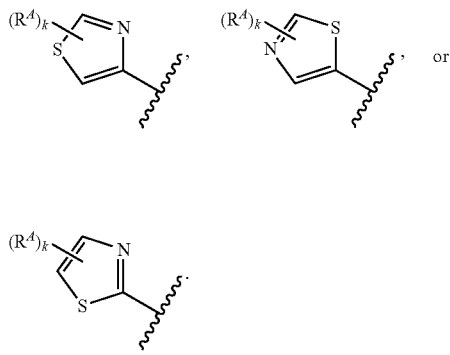

In certain embodiments, Ring A is a 5-membered monocyclic heteroaryl ring, wherein only three of the five atoms in the ring of the heteroaryl are independently nitrogen, oxygen, or sulfur. In certain embodiments, Ring A is of the formula:

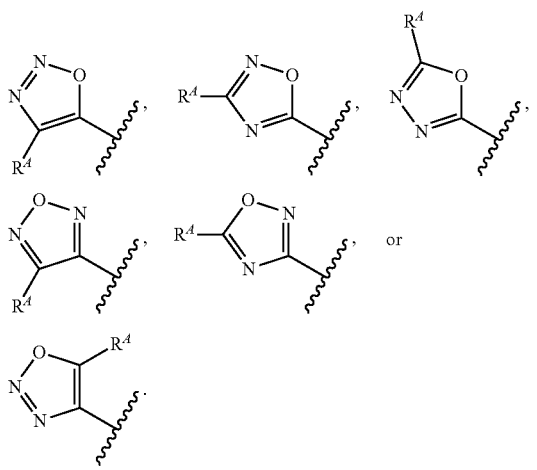

In certain embodiments, Ring A is of the formula:

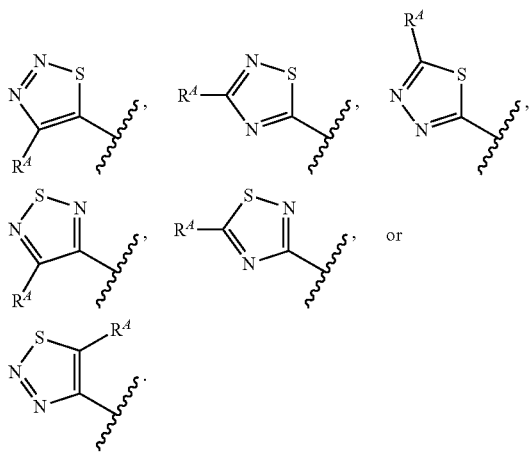

In certain embodiments, Ring A is of the formula:

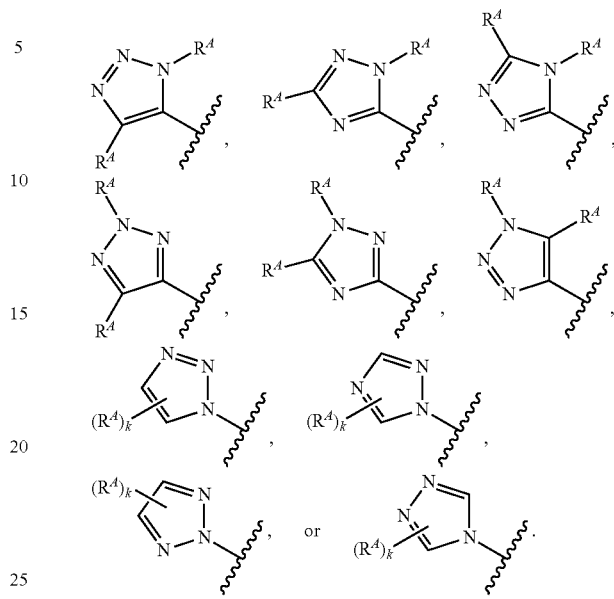

In certain embodiments, Ring A is a 5-membered monocyclic heteroaryl ring, wherein only four of the five atoms in the ring of the heteroaryl are nitrogen, oxygen, or sulfur. In certain embodiments, Ring A is of the formula:

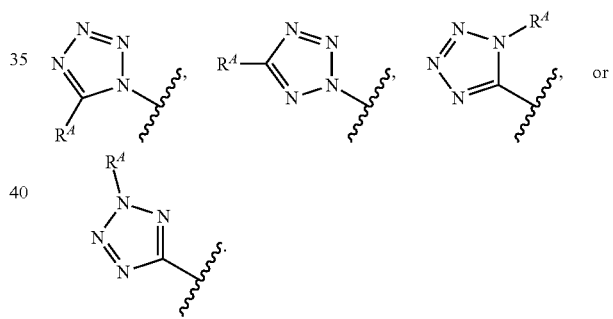

In certain embodiments, Ring A is bicyclic heteroaryl, wherein the point of attachment may be on any atom of the bicyclic heteroaryl ring system, as valency permits. In certain embodiments, Ring A is a monocyclic heteroaryl ring fused with phenyl. In certain embodiments, Ring A is a 5-membered monocyclic heteroaryl ring fused with phenyl. In certain embodiments, Ring A is a 6-membered monocyclic heteroaryl ring fused with phenyl. In certain embodiments, Ring A is a monocyclic heteroaryl ring fused with another monocyclic heteroaryl. In certain embodiments, Ring A is a 5-membered monocyclic heteroaryl ring fused with another 5-membered monocyclic heteroaryl. In certain embodiments, Ring A is a 5-membered monocyclic heteroaryl ring fused with a 6-membered monocyclic heteroaryl. In certain embodiments, Ring A is a 6-membered monocyclic heteroaryl ring fused with another 6-membered monocyclic heteroaryl.

Ring A of compounds of Formula (I) may include one or more substituents $R^A$. In certain embodiments, at least one $R^A$ is H. In certain embodiments, at least one $R^A$ is halogen. In certain embodiments, at least one $R^A$ is F. In certain embodiments, at least one $R^A$ is Cl. In certain embodiments, at least one $R^A$ is Br. In certain embodiments, at least one $R^A$ is I (iodine). In certain embodiments, at least one $R^A$ is substituted acyl. In certain embodiments, at least one $R^A$ is unsubstituted acyl. In certain embodiments, at least one $R^A$ is substituted alkyl. In certain embodiments, at least one $R^A$ is unsubstituted alkyl. In certain embodiments, at least one $R^A$ is $C_{1-6}$ alkyl. In certain embodiments, at least one $R^A$ is methyl. In certain embodiments, at least one $R^A$ is substituted methyl. In certain embodiments, at least one $R^A$ is —$CH_2F$. In certain embodiments, at least one $R^A$ is —$CHF_2$. In certain embodiments, at least one $R^A$ is —$CF_3$. In certain embodiments, at least one $R^A$ is Bn. In certain embodiments, at least one $R^A$ is ethyl. In certain embodiments, at least one $R^A$ is substituted ethyl. In certain embodiments, at least one $R^A$ is —$(CH_2)_2Ph$. In certain embodiments, at least one $R^A$ is propyl. In certain embodiments, at least one $R^A$ is butyl. In certain embodiments, at least one $R^A$ is pentyl. In certain embodiments, at least one $R^A$ is hexyl. In certain embodiments, at least one $R^A$ is substituted alkenyl. In certain embodiments, at least one $R^A$ is unsubstituted alkenyl. In certain embodiments, at least one $R^A$ is vinyl. In certain embodiments, at least one $R^A$ is substituted alkynyl. In certain embodiments, at least one $R^A$ is unsubstituted alkynyl. In certain embodiments, at least one $R^A$ is ethynyl. In certain embodiments, at least one $R^A$ is substituted carbocyclyl. In certain embodiments, at least one $R^A$ is unsubstituted carbocyclyl. In certain embodiments, at least one $R^A$ is cylcopropyl. In certain embodiments, at least one $R^A$ is cylcobutyl. In certain embodiments, at least one $R^A$ is cyclopentyl. In certain embodiments, at least one $R^A$ is cyclohexyl. In certain embodiments, at least one $R^A$ is cycloheptyl. In certain embodiments, at least one $R^A$ is substituted heterocyclyl. In certain embodiments, at least one $R^A$ is unsubstituted heterocyclyl. In certain embodiments, at least one $R^A$ is substituted aryl. In certain embodiments, at least one $R^A$ is unsubstituted aryl. In certain embodiments, at least one $R^A$ is substituted phenyl. In certain embodiments, at least one $R^A$ is unsubstituted phenyl. In certain embodiments, at least one $R^A$ is substituted naphthyl. In certain embodiments, at least one $R^A$ is unsubstituted naphthyl. In certain embodiments, at least one $R^A$ is substituted heteroaryl. In certain embodiments, at least one $R^A$ is unsubstituted heteroaryl. In certain embodiments, at least one $R^A$ is monocyclic heteroaryl. In certain embodiments, at least one $R^A$ is 5-membered monocyclic heteroaryl. In certain embodiments, at least one $R^A$ is 5-membered monocyclic heteroaryl, wherein only one of the five atoms in the ring of the heteroaryl is nitrogen, oxygen, or sulfur. In certain embodiments, at least one $R^A$ is 5-membered monocyclic heteroaryl, wherein only two of the five atoms in the ring of the heteroaryl are independently nitrogen, oxygen, or sulfur. In certain embodiments, at least one $R^A$ is 5-membered monocyclic heteroaryl, wherein only three of the five atoms in the ring of the heteroaryl are independently nitrogen, oxygen, or sulfur. In certain embodiments, at least one $R^A$ is tetrazolyl. In certain embodiments, at least one $R^A$ is 6-membered monocyclic heteroaryl. In certain embodiments, at least one $R^A$ is 6-membered monocyclic heteroaryl, wherein only one of the six atoms in the ring of the heteroaryl is nitrogen. In certain embodiments, at least one $R^A$ is 6-membered monocyclic heteroaryl, wherein only two of the six atoms in the ring of the heteroaryl are nitrogen. In certain embodiments, at least one $R^A$ is triazinyl. In certain embodiments, at least one $R^A$ is tetrazinyl. In certain embodiments, at least one $R^A$ is bicyclic heteroaryl, wherein the point of attachment may be on any atom of the bicyclic heteroaryl ring system, as valency permits. In certain embodiments, at least one $R^A$ is a monocyclic heteroaryl ring fused with phenyl. In certain embodiments, at least one $R^A$ is a 5-membered monocyclic heteroaryl ring fused with phenyl. In certain embodiments, at least one $R^A$ is a 6-membered monocyclic heteroaryl ring fused with phenyl. In certain embodiments, at least one $R^A$ is a monocyclic heteroaryl ring fused with another monocyclic heteroaryl. In certain embodiments, at least one $R^A$ is a 5-membered monocyclic heteroaryl ring fused with another 5-membered monocyclic heteroaryl. In certain embodiments, at least one $R^A$ is a 5-membered monocyclic heteroaryl ring fused with a 6-membered monocyclic heteroaryl. In certain embodiments, at least one $R^A$ is a 6-membered monocyclic heteroaryl fused with another 6-membered monocyclic heteroaryl. In certain embodiments, at least one $R^A$ is —$OR^{A1}$. In certain embodiments, at least one $R^A$ is -OMe. In certain embodiments, at least one $R^A$ is -OEt. In certain embodiments, at least one $R^A$ is -OPr. In certain embodiments, at least one $R^A$ is -OBu. In certain embodiments, at least one $R^A$ is —O(pentyl). In certain embodiments, at least one $R^A$ is —O(hexyl). In certain embodiments, at least one $R^A$ is -OPh. In certain embodiments, at least one $R^A$ is -OBn. In certain embodiments, at least one $R^A$ is —$O(CH_2)_2Ph$. In certain embodiments, at least one $R^A$ is —OH. In certain embodiments, at least one $R^A$ is —$SR^{A1}$. In certain embodiments, at least one $R^A$ is —SH. In certain embodiments, at least one $R^A$ is —$N(R^A)_2$. In certain embodiments, at least one $R^A$ is —$NH_2$. In certain embodiments, at least one $R^A$ is —CN. In certain embodiments, at least one $R^A$ is —SCN. In certain embodiments, at least one $R^A$ is —$C(=NR^{A1})R^{A1}$, —$C(=NR^{A1})OR^{A1}$, or —$C(=NR^{A1})N(R^{A1})_2$. In certain embodiments, at least one $R^A$ is —$C(=O)R^{A1}$, —$C(=O)OR^{A1}$, or —$C(=O)N(R^{A1})_2$. In certain embodiments, at least one $R^A$ is —$NO_2$. In certain embodiments, at least one $R^A$ is —$NR^{A1}C(=O)R^{A1}$, —$NR^{A1}C(=O)OR^{A1}$, or —$NR^{A1}C(=O)N(R^{A1})_2$. In certain embodiments, at least one $R^A$ is —$OC(=O)R^{A1}$, —$OC(=O)OR^{A1}$, or —$OC(=O)N(R^A)_2$. In certain embodiments, at least one $R^A$ is a nitrogen protecting group when attached to a nitrogen atom. In certain embodiments, at least one $R^A$ is Bn, BOC, Cbz, Fmoc, trifluoroacetyl, triphenylmethyl, or Ts when attached to a nitrogen atom.

In compounds of Formula (I), two $R^A$ groups may be joined to form a substituted or unsubstituted carbocyclic ring. In certain embodiments, two $R^A$ groups are joined to form a substituted or unsubstituted cyclopropyl ring. In certain embodiments, two $R^A$ groups are joined to form a substituted or unsubstituted cyclobutyl ring. In certain embodiments, two $R^A$ groups are joined to form a substituted or unsubstituted cyclopentyl ring. In certain embodiments, two $R^A$ groups are joined to form a substituted or unsubstituted cyclohexyl ring. In certain embodiments, two $R^A$ groups are joined to form a substituted or unsubstituted cycloheptyl ring. In certain embodiments, two $R^A$ groups are joined to form a substituted or unsubstituted cyclooctyl ring. In certain embodiments, two $R^A$ groups are joined to form a substituted or unsubstituted cyclononyl ring. In certain embodiments, two $R^A$ groups are joined to form a substituted or unsubstituted cyclodecyl ring.

In certain embodiments, two $R^A$ groups are joined to form a substituted or unsubstituted heterocyclic ring. In certain embodiments, two $R^A$ groups are joined to form a substituted or unsubstituted 4-membered heterocyclic ring. In certain embodiments, two $R^A$ groups are joined to form a substituted or unsubstituted 5-membered heterocyclic ring. In certain embodiments, two $R^A$ groups are joined to form a substituted or unsubstituted 6-membered heterocyclic ring. In certain embodiments, two $R^A$ groups are joined to form a substituted or unsubstituted 7-membered heterocyclic ring. In certain embodiments, two $R^A$ groups are joined to form a substituted or unsubstituted 8-membered heterocyclic ring. In certain embodiments, two $R^A$ groups are joined to form a substituted or unsubstituted 9-membered heterocyclic ring. In certain embodiments, two $R^A$ groups are joined to form a substituted or unsubstituted 10-membered heterocyclic ring.

In certain embodiments, two $R^A$ groups are joined to form a substituted or unsubstituted aryl ring. In certain embodiments, two $R^A$ groups are joined to form a substituted or unsubstituted monocyclic aryl ring. In certain embodiments, two $R^A$ groups are joined to form a substituted or unsubstituted phenyl ring. In certain embodiments, two $R^A$ groups are joined to form a substituted or unsubstituted bicyclic aryl ring. In certain embodiments, two $R^A$ groups are joined to form a substituted or unsubstituted naphthyl ring.

In certain embodiments, two $R^A$ groups are joined to form a substituted or unsubstituted heteroaryl ring. In certain embodiments, two $R^A$ groups are joined to form a substituted or unsubstituted monocyclic heteroaryl ring. In certain embodiments, two $R^A$ groups are joined to form a substituted or unsubstituted 5-membered monocyclic heteroaryl ring. In certain embodiments, two $R^A$ groups are joined to form a substituted or unsubstituted 6-membered monocyclic heteroaryl ring. In certain embodiments, two $R^A$ groups are joined to form a substituted or unsubstituted, bicyclic heteroaryl ring. In certain embodiments, two $R^A$ groups are joined to form a substituted or unsubstituted, 5,6-membered bicyclic heteroaryl ring. In certain embodiments, two $R^A$ groups are joined to form a substituted or unsubstituted, 6,5-membered bicyclic heteroaryl ring. In certain embodiments, two $R^A$ groups are joined to form a substituted or unsubstituted, 6,6-membered bicyclic heteroaryl ring.

In certain embodiments, at least one $R^{A1}$ is H. In certain embodiments, at least one $R^{A1}$ is substituted acyl. In certain embodiments, at least one $R^{A1}$ is unsubstituted acyl. In certain embodiments, at least one $R^{A1}$ is acetyl. In certain embodiments, at least one $R^{A1}$ is substituted alkyl. In certain embodiments, at least one $R^{A1}$ is unsubstituted alkyl. In certain embodiments, at least one $R^{A1}$ is $C_{1-6}$ alkyl. In certain embodiments, at least one $R^{A1}$ is methyl. In certain embodiments, at least one $R^{A1}$ is ethyl. In certain embodiments, at least one $R^{A1}$ is propyl. In certain embodiments, at least one $R^{A1}$ is butyl. In certain embodiments, at least one $R^{A1}$ is pentyl. In certain embodiments, at least one $R^{A1}$ is hexyl. In certain embodiments, at least one $R^{A1}$ is substituted alkenyl. In certain embodiments, at least one $R^{A1}$ is unsubstituted alkenyl. In certain embodiments, at least one $R^{A1}$ is vinyl. In certain embodiments, at least one $R^{A1}$ is substituted alkynyl. In certain embodiments, at least one $R^{A1}$ is unsubstituted alkynyl. In certain embodiments, at least one $R^{A1}$ is ethynyl. In certain embodiments, at least one $R^{A1}$ is substituted carbocyclyl. In certain embodiments, at least one $R^{A1}$ is unsubstituted carbocyclyl. In certain embodiments, at least one $R^{A1}$ is cylcopropyl. In certain embodiments, at least one $R^{A1}$ is cylcobutyl. In certain embodiments, at least one $R^{A1}$ is cyclopentyl. In certain embodiments, at least one $R^{A1}$ is cyclohexyl. In certain embodiments, at least one $R^{A1}$ is cycloheptyl. In certain embodiments, at least one $R^{A1}$ is substituted heterocyclyl. In certain embodiments, at least one $R^{A1}$ is unsubstituted heterocyclyl. In certain embodiments, at least one $R^{A1}$ is substituted aryl. In certain embodiments, at least one $R^{A1}$ is unsubstituted aryl. In certain embodiments, at least one $R^{A1}$ is substituted phenyl. In certain embodiments, at least one $R^{A1}$ is unsubstituted phenyl. In certain embodiments, at least one $R^{A1}$ is substituted heteroaryl. In certain embodiments, at least one $R^{A1}$ is unsubstituted heteroaryl. In certain embodiments, at least one $R^{A1}$ is substituted pyridyl. In certain embodiments, at least one $R^{A1}$ is unsubstituted pyridyl. In certain embodiments, at least one $R^{A1}$ is a nitrogen protecting group when attached to a nitrogen atom. In certain embodiments, at least one $R^{A1}$ is Bn, Boc, Cbz, Fmoc, trifluoroacetyl, triphenylmethyl, or Ts when attached to a nitrogen atom. In certain embodiments, $R^{A1}$ is an oxygen protecting group when attached to an oxygen atom. In certain embodiments, $R^{A1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{A1}$ is a sulfur protecting group when attached to a sulfur atom. In certain embodiments, $R^{A1}$ is acetamidomethyl, t-Bu, 3-nitro-2-pyridine sulfenyl, 2-pyridine-sulfenyl, or triphenylmethyl when attached to a sulfur atom. In certain embodiments, two $R^{A1}$ groups are joined to form a substituted heterocyclic ring. In certain embodiments, two $R^{A1}$ groups are joined to form an unsubstituted heterocyclic ring. In certain embodiments, two $R^{A1}$ groups are joined to form a substituted heteroaryl ring. In certain embodiments, two $R^{A1}$ groups are joined to form an unsubstituted heteroaryl ring.

In certain embodiments, k is 0. In certain embodiments, k is 1. In certain embodiments, k is 2. In certain embodiments, k is 3. In certain embodiments, k is 4. In certain embodiments, k is 5.

Compounds of Formula (I) may include zero, one, two, or more substituents $R^B$. In certain embodiments, at least one $R^B$ is H. In certain embodiments, at least one $R^B$ is halogen. In certain embodiments, at least one $R^B$ is F. In certain embodiments, at least one $R^B$ is Cl. In certain embodiments, at least one $R^B$ is Br. In certain embodiments, at least one $R^B$ is I (iodine). In certain embodiments, at least one $R^B$ is substituted acyl. In certain embodiments, at least one $R^B$ is unsubstituted acyl. In certain embodiments, at least one $R^B$ is substituted alkyl. In certain embodiments, at least one $R^B$ is unsubstituted alkyl. In certain embodiments, at least one $R^B$ is $C_{1-6}$ alkyl. In certain embodiments, at least one $R^B$ is methyl. In certain embodiments, at least one $R^B$ is substituted methyl. In certain embodiments, at least one $R^B$ is —CH$_2$F. In certain embodiments, at least one $R^B$ is —CHF$_2$. In certain embodiments, at least one $R^B$ is —CF$_3$. In certain embodiments, at least one $R^B$ is benzyl (Bn). In certain embodiments, at least one $R^B$ is ethyl. In certain embodiments, at least one $R^B$ is substituted ethyl. In certain embodiments, at least one $R^B$ is —(CH$_2$)$_2$Ph. In certain embodiments, at least one $R^B$ is propyl. In certain embodiments, at least one $R^B$ is butyl. In certain embodiments, at least one $R^B$ is pentyl. In certain embodiments, at least one $R^B$ is hexyl. In certain embodiments, at least one $R^B$ is substituted alkenyl. In certain embodiments, at least one $R^B$ is unsubstituted alkenyl. In certain embodiments, at least one $R^B$ is vinyl. In certain embodiments, at least one $R^B$ is substituted alkynyl. In certain embodiments, at least one $R^B$ is unsubstituted alkynyl. In certain embodiments, at least one $R^B$ is ethynyl. In certain embodiments, at least one $R^B$ is substituted carbocyclyl. In certain embodiments, at least one $R^B$ is unsubstituted carbocyclyl. In certain embodiments, at least one $R^B$ is cylcopropyl. In certain embodiments, at least one $R^B$ is cylcobutyl. In certain embodiments, at least one $R^B$ is cyclopentyl. In certain embodiments, at least one $R^B$ is cyclohexyl. In certain embodiments, at least one $R^B$ is cycloheptyl. In certain embodiments, at least one $R^B$ is substituted heterocyclyl. In certain embodiments, at least one $R^B$ is unsubstituted heterocyclyl. In certain embodiments, at least one $R^B$ is substituted aryl. In certain embodiments, at least one $R^B$ is unsubstituted aryl. In certain embodiments, at least one $R^B$ is substituted phenyl. In certain embodiments, at least one $R^B$ is unsubstituted phenyl. In certain embodiments, at least one $R^B$ is substituted naphthyl. In certain embodiments, at least one $R^B$ is unsubstituted naphthyl. In certain embodiments, at least one $R^B$ is substituted heteroaryl. In certain embodiments, at least one $R^B$ is unsubstituted heteroaryl. In certain embodiments, at least one $R^B$ is monocyclic heteroaryl. In certain embodiments, at least one $R^B$ is 5-membered monocyclic heteroaryl. In certain embodiments, at least one $R^B$ is 5-membered monocyclic heteroaryl, wherein only one of the five atoms in the ring of the heteroaryl is nitrogen, oxygen, or sulfur. In certain embodiments, at least one $R^B$ is 5-membered monocyclic heteroaryl, wherein only two of the five atoms in the ring of the heteroaryl are independently nitrogen, oxygen, or sulfur. In certain embodiments, at least one $R^B$ is 5-membered monocyclic heteroaryl, wherein only three of the five atoms in the ring of the heteroaryl are independently nitrogen, oxygen, or sulfur. In certain embodiments, at least one $R^B$ is tetrazolyl. In certain embodiments, at least one $R^B$ is 6-membered monocyclic heteroaryl. In certain embodiments, at least one $R^B$ is 6-membered monocyclic heteroaryl, wherein only one of the six atoms in the ring of the heteroaryl is nitrogen. In certain embodiments, at least one $R^B$ is 6-membered monocyclic heteroaryl, wherein only two of the six atoms in the ring of the heteroaryl are nitrogen. In certain embodiments, at least one $R^B$ is triazinyl. In certain embodiments, at least one $R^B$ is tetrazinyl. In certain embodiments, at least one $R^B$ is bicyclic heteroaryl, wherein the point of attachment may be on any atom of the bicyclic heteroaryl, as valency permits. In certain embodiments, at least one $R^B$ is a monocyclic heteroaryl fused with phenyl. In certain embodiments, at least one $R^B$ is a 5-membered monocyclic heteroaryl fused with phenyl. In certain embodiments, at least one $R^B$ is a 6-membered monocyclic heteroaryl fused with phenyl. In certain embodiments, at least one $R^B$ is a monocyclic heteroaryl fused with another monocyclic heteroaryl. In certain embodiments, at least one $R^B$ is a 5-membered monocyclic heteroaryl fused with another 5-membered monocyclic heteroaryl. In certain embodiments, at least one $R^B$ is a 5-membered monocyclic heteroaryl fused with a 6-membered monocyclic heteroaryl. In certain embodiments, at least one $R^B$ is a 6-membered monocyclic heteroaryl fused with another 6-membered monocyclic heteroaryl. In certain embodiments, at least one $R^B$ is —$OR^{B1}$. In certain embodiments, at least one $R^B$ is -OMe. In certain embodiments, at least one $R^B$ is -OEt. In certain embodiments, at least one $R^B$ is -OPr. In certain embodiments, at least one $R^B$ is -OBu. In certain embodiments, at least one $R^B$ is —O(pentyl). In certain embodiments, at least one $R^B$ is —O(hexyl). In certain embodiments, at least one $R^B$ is -OPh. In certain embodiments, at least one $R^B$ is -OBn. In certain embodiments, at least one $R^B$ is —O(CH$_2$)$_2$Ph. In certain embodiments, at least one $R^B$ is —OH. In certain embodiments, at least one $R^B$ is —$SR^{B1}$. In certain embodiments, at least one $R^B$ is -SMe. In certain embodiments, at least one $R^B$ is —SH. In certain embodiments, at least one $R^B$ is —N($R^{B1}$)$_2$. In certain embodiments, at least one $R^B$ is —N(Me)$_2$. In certain embodiments, at least one $R^B$ is —NHMe. In certain embodiments, at least one $R^B$ is —NHAc. In certain embodiments, at least one $R^B$ is —NH$_2$. In certain embodiments, at least one $R^B$ is —CN. In certain embodiments, at least one $R^B$ is —SCN. In certain embodiments, at least one $R^B$ is —C(=N$R^{B1}$)$R^{B1}$, —C(=N$R^{B1}$)O$R^{B1}$, or —C(=N$R^{B1}$)N($R^{B1}$)$_2$. In certain embodiments, at least one $R^B$ is —C(=O) $R^{B1}$. In certain embodiments, at least one $R^B$ is —C(=O) O$R^{B1}$. In certain embodiments, at least one $R^B$ is —C(=O) OMe. In certain embodiments, at least one $R^B$ is —C(=O) N($R^{B1}$)$_2$. In certain embodiments, at least one $R^B$ is —C(=O)N(Me)$_2$. In certain embodiments, at least one $R^B$ is —C(=O)NHMe. In certain embodiments, at least one $R^B$ is —C(=O)NH$_2$. In certain embodiments, at least one $R^B$ is —NO$_2$. In certain embodiments, at least one $R^B$ is —$NR^{B1}$C (=O)$R^{B1}$, —$NR^{B1}$C(=O)O$R^{B1}$, or —$NR^{B1}$C(=O)N($R^{B1}$)$_2$. In certain embodiments, at least one $R^B$ is —OC(=O)$R^{B1}$, —OC(=O)O$R^{B1}$, or —OC(=O)N($R^{B1}$)$_2$.

In compounds of Formula (I), two $R^B$ groups may be joined to form a substituted or unsubstituted carbocyclic ring. In certain embodiments, two $R^B$ groups are joined to form a substituted or unsubstituted cyclopropyl ring. In certain embodiments, two $R^B$ groups are joined to form a substituted or unsubstituted cyclobutyl ring. In certain embodiments, two $R^B$ groups are joined to form a substituted or unsubstituted cyclopentyl ring. In certain embodiments, two $R^B$ groups are joined to form a substituted or unsubstituted cyclohexyl ring. In certain embodiments, two $R^B$ groups are joined to form a substituted or unsubstituted cycloheptyl ring. In certain embodiments, two $R^B$ groups are joined to form a substituted or unsubstituted cyclooctyl ring. In certain embodiments, two $R^B$ groups are joined to form a substituted or unsubstituted cyclononyl ring. In certain embodiments, two $R^B$ groups are joined to form a substituted or unsubstituted cyclodecyl ring.

In certain embodiments, two $R^B$ groups are joined to form a substituted or unsubstituted heterocyclic ring. In certain embodiments, two $R^B$ groups are joined to form a substituted or unsubstituted 4-membered heterocyclic ring. In certain embodiments, two $R^B$ groups are joined to form a substituted or unsubstituted 5-membered heterocyclic ring. In certain embodiments, two $R^B$ groups are joined to form a substituted or unsubstituted 6-membered heterocyclic ring. In certain embodiments, two $R^B$ groups are joined to form a substituted or unsubstituted 7-membered heterocyclic ring. In certain embodiments, two $R^B$ groups are joined to form a substituted or unsubstituted 8-membered heterocyclic ring. In certain embodiments, two $R^B$ groups are joined to form a substituted or unsubstituted 9-membered heterocyclic ring. In certain embodiments, two $R^B$ groups are joined to form a substituted or unsubstituted 10-membered heterocyclic ring.

In certain embodiments, two $R^B$ groups are joined to form a substituted or unsubstituted aryl ring. In certain embodiments, two $R^B$ groups are joined to form a substituted or unsubstituted monocyclic aryl ring. In certain embodiments, two $R^B$ groups are joined to form a substituted or unsubstituted phenyl ring. In certain embodiments, two $R^B$ groups are joined to form a substituted or unsubstituted bicyclic aryl ring. In certain embodiments, two $R^B$ groups are joined to form a substituted or unsubstituted naphthyl ring.

In certain embodiments, two $R^B$ groups are joined to form a substituted or unsubstituted heteroaryl ring. In certain embodiments, two $R^B$ groups are joined to form a substituted or unsubstituted monocyclic heteroaryl ring. In certain embodiments, two $R^B$ groups are joined to form a substituted or unsubstituted, 5-membered monocyclic heteroaryl ring. In certain embodiments, two $R^B$ groups are joined to form a substituted or unsubstituted, 6-membered monocyclic heteroaryl ring. In certain embodiments, two $R^B$ groups are joined to form a substituted or unsubstituted, bicyclic heteroaryl ring. In certain embodiments, two $R^B$ groups are joined to form a substituted or unsubstituted, 5,6-membered bicyclic heteroaryl ring. In certain embodiments, two $R^B$ groups are joined to form a substituted or unsubstituted, 6,5-membered bicyclic heteroaryl ring. In certain embodiments, two $R^B$ groups are joined to form a substituted or unsubstituted, 6,6-membered bicyclic heteroaryl ring.

In certain embodiments, at least one $R^{B1}$ is H. In certain embodiments, at least one $R^{B1}$ is substituted acyl. In certain embodiments, at least one $R^{B1}$ is unsubstituted acyl. In certain embodiments, at least one $R^{B1}$ is acetyl. In certain embodiments, at least one $R^{B1}$ is substituted alkyl. In certain embodiments, at least one $R^{B1}$ is unsubstituted alkyl. In certain embodiments, at least one $R^{B1}$ is $C_{1-6}$ alkyl. In certain embodiments, at least one $R^{B1}$ is methyl. In certain embodiments, at least one $R^{B1}$ is ethyl. In certain embodiments, at least one $R^{B1}$ is propyl. In certain embodiments, at least one $R^{B1}$ is butyl. In certain embodiments, at least one $R^{B1}$ is pentyl. In certain embodiments, at least one $R^{B1}$ is hexyl. In certain embodiments, at least one $R^{B1}$ is substituted alkenyl. In certain embodiments, at least one $R^{B1}$ is unsubstituted alkenyl. In certain embodiments, at least one $R^{B1}$ is vinyl. In certain embodiments, at least one $R^{B1}$ is substituted alkynyl. In certain embodiments, at least one $R^{B1}$ is unsubstituted alkynyl. In certain embodiments, at least one $R^{B1}$ is ethynyl. In certain embodiments, at least one $R^{B1}$ is substituted carbocyclyl. In certain embodiments, at least one $R^{B1}$ is unsubstituted carbocyclyl. In certain embodiments, at least one $R^{B1}$ is cylcopropyl. In certain embodiments, at least one $R^{B1}$ is cylcobutyl. In certain embodiments, at least one $R^{B1}$ is cyclopentyl. In certain embodiments, at least one $R^{B1}$ is cyclohexyl. In certain embodiments, at least one $R^{B1}$ is cycloheptyl. In certain embodiments, at least one $R^{B1}$ is substituted heterocyclyl. In certain embodiments, at least one $R^{B1}$ is unsubstituted heterocyclyl. In certain embodiments, at least one $R^{B1}$ is substituted aryl. In certain embodiments, at least one $R^{B1}$ is unsubstituted aryl. In certain embodiments, at least one $R^{B1}$ is substituted phenyl. In certain embodiments, at least one $R^{B1}$ is unsubstituted phenyl. In certain embodiments, at least one $R^{B1}$ is substituted heteroaryl. In certain embodiments, at least one $R^{B1}$ is unsubstituted heteroaryl. In certain embodiments, at least one $R^{B1}$ is substituted pyridyl. In certain embodiments, at least one $R^{B1}$ is unsubstituted pyridyl. In certain embodiments, at least one $R^{B1}$ is a nitrogen protecting group when attached to a nitrogen atom. In certain embodiments, at least one $R^{B1}$ is Bn, Boc, Cbz, Fmoc, trifluoroacetyl, triphenylmethyl, or Ts when attached to a nitrogen atom. In certain embodiments, $R^{B1}$ is an oxygen protecting group when attached to an oxygen atom. In certain embodiments, $R^{B1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{B1}$ is a sulfur protecting group when attached to a sulfur atom. In certain embodiments, $R^{B1}$ is acetamidomethyl, t-Bu, 3-nitro-2-pyridine sulfenyl, 2-pyridine-sulfenyl, or triphenylmethyl when attached to a sulfur atom. In certain embodiments, two $R^{B1}$ groups are joined to form a substituted heterocyclic ring. In certain embodiments, two $R^{B1}$ groups are joined to form an unsubstituted heterocyclic ring. In certain embodiments, two $R^{B1}$ groups are joined to form a substituted heteroaryl ring. In certain embodiments, two $R^{B1}$ groups are joined to form an unsubstituted heteroaryl ring.

In certain embodiments, m is 0. In certain embodiments, m is 1. In certain embodiments, m is 2. In certain embodiments, m is 3. In certain embodiments, m is 4. In certain embodiments, m is 5. In certain embodiments, m is 6. In certain embodiments, m is 7. In certain embodiments, m is 8. In certain embodiments, m is 9. In certain embodiments, m is 10.

In certain embodiments, n is 1. In certain embodiments, n is 2.

In certain embodiments, n is 1, and m is 0. In certain embodiments, n is 2, and m is 0.

In certain embodiments, n is 1, m is 0, and Ring A is monosubstituted phenyl. In certain embodiments, n is 2, m is 0, and Ring A is monosubstituted phenyl.

Compounds of Formula (I) include a substituent $R^C$ attached to the 3-nitrogen atom of the thiohydantoin moiety. In certain embodiments, $R^C$ is H. In certain embodiments, $R^C$ is substituted acyl. In certain embodiments, $R^C$ is unsubstituted acyl. In certain embodiments, $R^C$ is substituted alkyl. In certain embodiments, $R^C$ is unsubstituted alkyl. In certain embodiments, $R^C$ is $C_{1-6}$ alkyl. In certain embodiments, $R^C$ is methyl. In certain embodiments, $R^C$ is substituted methyl. In certain embodiments, $R^C$ is —$CH_2F$. In certain embodiments, $R^C$ is —$CHF_2$. In certain embodiments, $R^C$ is —$CF_3$. In certain embodiments, $R^C$ is Bn. In certain embodiments, $R^C$ is ethyl. In certain embodiments, $R^C$ is substituted ethyl. In certain embodiments, $R^C$ is —$(CH_2)_2$Ph. In certain embodiments, $R^C$ is propyl. In certain embodiments, $R^C$ is butyl. In certain embodiments, $R^C$ is pentyl. In certain embodiments, $R^C$ is hexyl. In certain embodiments, $R^C$ is substituted alkenyl. In certain embodiments, $R^C$ is unsubstituted alkenyl. In certain embodiments, $R^C$ is vinyl. In certain embodiments, $R^C$ is substituted alkynyl. In certain embodiments, $R^C$ is unsubstituted alkynyl. In certain embodiments, $R^C$ is ethynyl. In certain embodiments, $R^C$ is substituted carbocyclyl. In certain embodiments, $R^C$ is unsubstituted carbocyclyl. In certain embodiments, $R^C$ is cylcopropyl. In certain embodiments, $R^C$ is cylcobutyl. In certain embodiments, $R^C$ is cyclopentyl. In certain embodiments, $R^C$ is cyclohexyl. In certain embodiments, $R^C$ is cycloheptyl. In certain embodiments, $R^C$ is substituted heterocyclyl. In certain embodiments, $R^C$ is unsubstituted heterocyclyl. In certain embodiments, $R^C$ is substituted aryl. In certain embodiments, $R^C$ is unsubstituted aryl. In certain embodiments, $R^C$ is substituted phenyl. In certain embodiments, $R^C$ is unsubstituted phenyl. In certain embodiments, $R^C$ is substituted naphthyl. In certain embodiments, $R^C$ is unsubstituted naphthyl. In certain embodiments, $R^C$ is —C(=$NR^{C1}$)$R^{C1}$, —C(=$NR^{C1}$)$OR^{C1}$, or —C(=$NR^{C1}$)N($R^{C1}$)$_2$. In certain embodiments, $R^C$ is —C(=O)$R^{C1}$. In certain embodiments, $R^C$ is —C(=O)Me, —C(=O)Et, —C(=O)Pr, or —C(=O)Bu. In certain embodiments, $R^C$ is —C(=O)$OR^{C1}$. In certain embodiments, $R^C$ is —C(=O)OMe. In certain embodiments, $R^C$ is —C(=O)OEt. In certain embodiments, $R^C$ is —C(=O)OPr. In certain embodiments, $R^C$ is —C(=O)OBu. In certain embodiments, $R^C$ is —C(=O)N($R^{C1}$)$_2$. In certain embodiments, $R^C$ is —C(=O)N(Me)$_2$. In certain embodiments, $R^C$ is —C(=O)NHMe. In certain embodiments, $R^C$ is —C(=O)$NH_2$. In certain embodiments, $R^C$ is —S(=O)$R^{C1}$, —S(=O)$OR^{C1}$, or —S(=O)N($R^{C1}$)$_2$. In certain embodiments, $R^C$ is —S(=O)$_2R^{C1}$. In certain embodiments, $R^C$ is —S(=O)$_2$Me, —S(=O)$_2CF_3$, —S(=O)$_2$Et, —S(=O)$_2$Pr, or —S(=O)$_2$Bu. In certain embodiments, $R^C$ is —S(=O)$_2OR^{C1}$. In certain embodiments, $R^C$ is —S(=O)$_2$OMe, —S(=O)$_2$OEt, —S(=O)$_2$OPr, or —S(=O)$_2$OBu. In certain embodiments, $R^C$ is —S(=O)$_2N(R^{C1})_2$. In certain embodiments, $R^C$ is —S(=O)$_2$N(Me)$_2$, —S(=O)$_2$NHMe, or —S(=O)$_2NH_2$. In certain embodiments, $R^C$ is —C(CN)=$NOR^{C1}$. In certain embodiments, $R^C$ is —C(CN)=NOMe, —C(CN)=NOEt, —C(CN)=NOPr, or —C(CN)=NOBu. In certain embodiments, $R^C$ is $CF_2$—$R^{C1}$. In certain embodiments, $R^C$ is —CHF—$R^C$. In certain embodiments, $R^C$ is

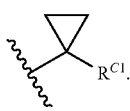

In certain embodiments, $R^C$ is unsubstituted heteroaryl. In certain embodiments, $R^C$ is substituted heteroaryl. In certain embodiments, $R^C$ is heteroaryl substituted with $-(R^D)_p$, wherein:

each instance of $R^D$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{D1}$, $-N(R^{D1})_2$, $-SR^{D1}$, $-CN$, $-SCN$, $-C(=NR^{D1})R^{D1}$, $-C(=NR^{D1})OR^{D1}$, $-C(=NR^{D1})N(R^{D1})_2$, $-C(=O)R^{D1}$, $-C(=O)OR^{D1}$, $-C(=O)N(R^{D1})_2$, $-NO_2$, $-NR^{D1}C(=O)R^{D1}$, $-NR^{D1}C(=O)OR^{D1}$, $-NR^{D1}C(=O)N(R^{D1})_2$, $-OC(=O)R^{D1}$, $-OC(=O)OR^{D1}$, $-OC(=O)N(R^{D1})_2$, or a nitrogen protecting group when attached to a nitrogen atom, or optionally two $R^D$ groups are joined to form a substituted or unsubstituted carbocyclic, substituted or unsubstituted heterocyclic, substituted or unsubstituted aryl, or substituted or unsubstituted heteroaryl ring;

each instance of $R^{D1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or optionally two $R^{D1}$ groups are joined to form a substituted or unsubstituted heterocyclic ring; and p is 0, 1, 2, 3, or 4.

In certain embodiments, $R^C$ is monocyclic heteroaryl. In certain embodiments, $R^C$ is 6-membered monocyclic heteroaryl. In certain embodiments, $R^C$ is 6-membered monocyclic heteroaryl, wherein only one of the six atoms of the heteroaryl ring is nitrogen. In certain embodiments, $R^C$ is of the formula:

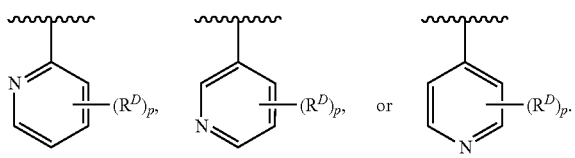

In certain embodiments, $R^C$ is 6-membered monocyclic heteroaryl, wherein only two of the six atoms in the ring of the heteroaryl are nitrogen. In certain embodiments, $R^C$ is of the formula:

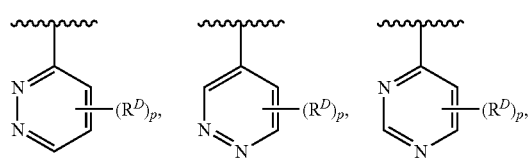

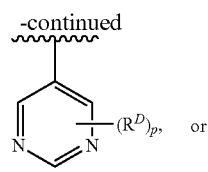

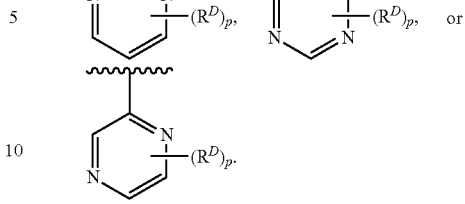

In certain embodiments, $R^C$ is 6-membered monocyclic heteroaryl, wherein only three of the six atoms of the heteroaryl ring are nitrogen. In certain embodiments, $R^C$ is of the formula:

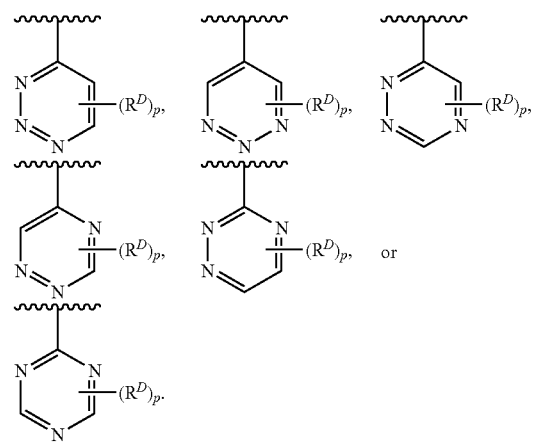

In certain embodiments, $R^C$ is 5-membered monocyclic heteroaryl. In certain embodiments, $R^C$ is 5-membered monocyclic heteroaryl, wherein one of the five atoms of the heteroaryl ring is nitrogen, oxygen, or sulfur. In certain embodiments, $R^C$ is of the formula:

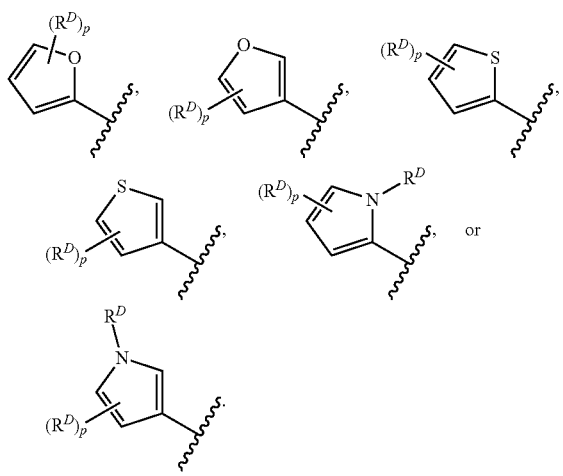

In certain embodiments, $R^C$ is 5-membered monocyclic heteroaryl, wherein two of the five atoms of the heteroaryl ring are independently selected from the group consisting of nitrogen, oxygen, and sulfur. In certain embodiments, $R^C$ is of the formula:

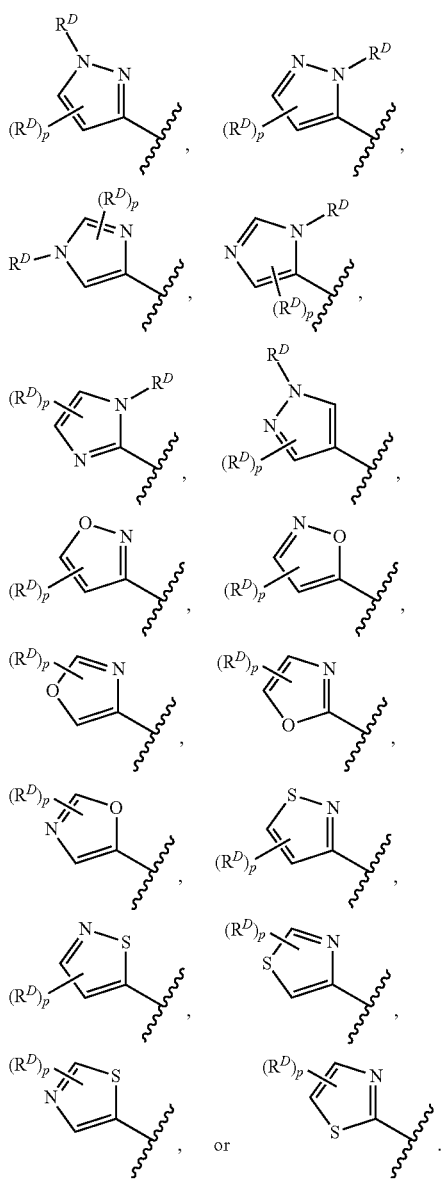

In certain embodiments, $R^C$ is 5-membered monocyclic heteroaryl, wherein three of the five atoms of the heteroaryl ring are independently selected from the group consisting of nitrogen, oxygen, and sulfur. In certain embodiments, $R^C$ is of the formula:

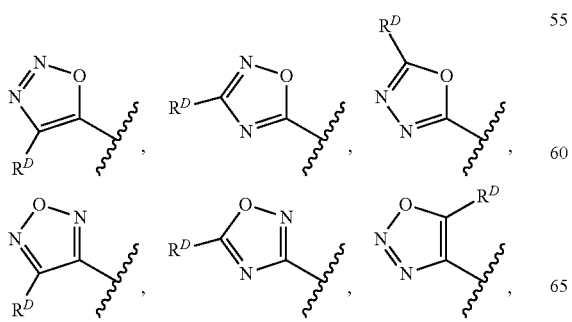

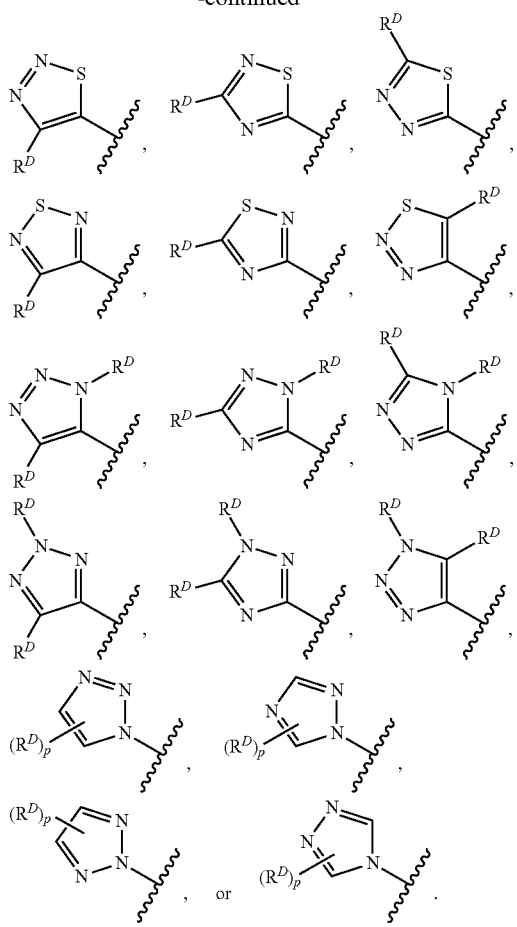

In certain embodiments $R^C$ is a 5-membered monocyclic heteroaryl, wherein four of the five atoms of the heteroaryl ring are independently selected from the group consisting of nitrogen, oxygen, and sulfur. In certain embodiments, $R^C$ is of the formula:

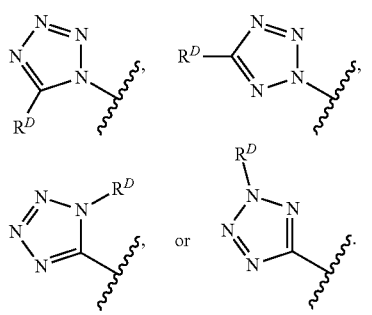

In certain embodiments, $R^C$ is of the formula:

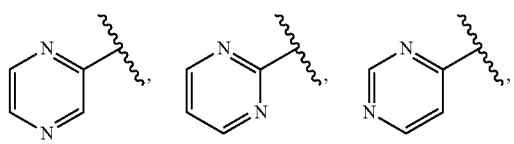

In certain embodiments, $R^C$ is bicyclic heteroaryl, wherein the point of attachment may be on any atom of the bicyclic heteroaryl ring system, as valency permits. In certain embodiments, $R^C$ is monocyclic heteroaryl fused with phenyl. In certain embodiments, $R^C$ is 5-membered monocyclic heteroaryl fused with phenyl. In certain embodiments, $R^C$ is 6-membered monocyclic heteroaryl fused with phenyl. In certain embodiments, $R^C$ is monocyclic heteroaryl fused with another monocyclic heteroaryl. In certain embodiments, $R^C$ is 5-membered monocyclic heteroaryl fused with another 5-membered monocyclic heteroaryl. In certain embodiments, $R^C$ is 5-membered monocyclic heteroaryl fused with a 6-membered monocyclic heteroaryl. In certain embodiments, $R^C$ is 6-membered monocyclic heteroaryl fused with another 6-membered monocyclic heteroaryl.

In certain embodiments, $R^{C1}$ is H. In certain embodiments, $R^{C1}$ is substituted acyl. In certain embodiments, $R^{C1}$ is unsubstituted acyl. In certain embodiments, $R^{C1}$ is acetyl. In certain embodiments, $R^{C1}$ is substituted alkyl. In certain embodiments, $R^{C1}$ is unsubstituted alkyl. In certain embodiments, $R^{C1}$ is $C_{1-6}$ alkyl. In certain embodiments, $R^{C1}$ is methyl. In certain embodiments, $R^{C1}$ is ethyl. In certain embodiments, $R^{C1}$ is propyl. In certain embodiments, $R^{C1}$ is butyl. In certain embodiments, $R^{C1}$ is pentyl. In certain embodiments, $R^{C1}$ is hexyl. In certain embodiments, $R^{C1}$ is substituted alkenyl. In certain embodiments, $R^{C1}$ is unsubstituted alkenyl. In certain embodiments, $R^{C1}$ is vinyl. In certain embodiments, $R^{C1}$ is substituted alkynyl. In certain embodiments, $R^{C1}$ is unsubstituted alkynyl. In certain embodiments, $R^{C1}$ is ethynyl. In certain embodiments, $R^{C1}$ is substituted carbocyclyl. In certain embodiments, $R^{C1}$ is unsubstituted carbocyclyl. In certain embodiments, $R^{C1}$ is cylcopropyl. In certain embodiments, $R^{C1}$ is cylcobutyl. In certain embodiments, $R^{C1}$ is cyclopentyl. In certain embodiments, $R^{C1}$ is cyclohexyl. In certain embodiments, $R^{C1}$ is cycloheptyl. In certain embodiments, $R^{C1}$ is substituted heterocyclyl. In certain embodiments, $R^{C1}$ is unsubstituted heterocyclyl. In certain embodiments, $R^{C1}$ is substituted aryl. In certain embodiments, $R^{C1}$ is unsubstituted aryl. In certain embodiments, $R^{C1}$ is substituted phenyl. In certain embodiments, $R^{C1}$ is unsubstituted phenyl. In certain embodiments, $R^{C1}$ is substituted heteroaryl. In certain embodiments, $R^{C1}$ is unsubstituted heteroaryl. In certain embodiments, $R^{C1}$ is substituted pyridyl. In certain embodiments, $R^{C1}$ is unsubstituted pyridyl. In certain embodiments, $R^{C1}$ is a nitrogen protecting group when attached to a nitrogen atom. In certain embodiments, $R^{C1}$ is Bn, Boc, Cbz, Fmoc, trifluoroacetyl, triphenylmethyl, or Ts when attached to a nitrogen atom. In certain embodiments, $R^{C1}$ is an oxygen protecting group when attached to an oxygen atom. In certain embodiments, $R^{C1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, two $R^{C1}$ groups are joined to form a substituted heterocyclic ring. In certain embodiments, two $R^{C1}$ groups are joined to form an unsubstituted heterocyclic ring. In certain embodiments, two $R^{C1}$ groups are joined to form a substituted heteroaryl ring. In certain embodiments, two $R^{C1}$ groups are joined to form an unsubstituted heteroaryl ring.

When $R^C$ of compounds of Formula (I) is heteroaryl, $R^C$ may include one or more substituents $R^D$. In certain embodiments, at least one $R^D$ is H. In certain embodiments, at least one $R^D$ is halogen. In certain embodiments, at least one $R^D$ is F. In certain embodiments, at least one $R^D$ is Cl. In certain embodiments, at least one $R^D$ is Br. In certain embodiments, at least one $R^D$ is I (iodine). In certain embodiments, at least one $R^D$ is substituted acyl. In certain embodiments, at least one $R^D$ is unsubstituted acyl. In certain embodiments, at least one $R^D$ is substituted alkyl. In certain embodiments, at least one $R^D$ is unsubstituted alkyl. In certain embodiments, at least one $R^D$ is $C_{1-6}$ alkyl. In certain embodiments, at least one $R^D$ is methyl. In certain embodiments, at least one $R^D$ is substituted methyl. In certain embodiments, at least one $R^D$ is —$CH_2F$. In certain embodiments, at least one $R^D$ is —$CHF_2$. In certain embodiments, at least one $R^D$ is —$CF_3$. In certain embodiments, at least one $R^D$ is benzyl (Bn). In certain embodiments, at least one $R^D$ is ethyl. In certain embodiments, at least one $R^D$ is substituted ethyl. In certain embodiments, at least one $R^D$ is —$(CH_2)_2$Ph. In certain embodiments, at least one $R^D$ is propyl. In certain embodiments, at least one $R^D$ is butyl. In certain embodiments, at least one $R^D$ is pentyl. In certain embodiments, at least one $R^D$ is hexyl. In certain embodiments, at least one $R^D$ is substituted alkenyl. In certain embodiments, at least one $R^D$ is unsubstituted alkenyl. In certain embodiments, at least one $R^D$ is vinyl. In certain embodiments, at least one $R^D$ is substituted alkynyl. In certain embodiments, at least one $R^D$ is unsubstituted alkynyl. In certain embodiments, at least one $R^D$ is ethynyl. In certain embodiments, at least one $R^D$ is substituted carbocyclyl. In certain embodiments, at least one $R^D$ is unsubstituted carbocyclyl. In certain embodiments, at least one $R^D$ is cylcopropyl. In certain embodiments, at least one $R^D$ is cylcobutyl. In certain embodiments, at least one $R^D$ is cyclopentyl. In certain embodiments, at least one $R^D$ is cyclohexyl. In certain embodiments, at least one $R^D$ is cycloheptyl. In certain embodiments, at least one $R^D$ is substituted heterocyclyl. In certain embodiments, at least one $R^D$ is unsubstituted heterocyclyl. In certain embodiments, at least one $R^D$ is substituted aryl. In certain embodiments, at least one $R^D$ is unsubstituted aryl. In certain embodiments, at least one $R^D$ is substituted phenyl. In certain embodiments, at least one $R^D$ is unsubstituted phenyl. In certain embodiments, at least one $R^D$ is substituted naphthyl. In certain embodiments, at least one $R^D$ is unsubstituted naphthyl. In certain embodiments, at least one $R^D$ is substituted heteroaryl. In certain embodiments, at least one $R^D$ is unsubstituted heteroaryl. In certain embodiments, at least one $R^D$ is monocyclic heteroaryl. In certain embodiments, at least one $R^D$ is 5-membered monocyclic heteroaryl. In certain embodiments, at least one $R^D$ is 5-membered monocyclic heteroaryl, wherein only one of the five atoms of the heteroaryl ring is nitrogen, oxygen, or sulfur. In certain embodiments, at least one $R^D$ is 5-membered monocyclic heteroaryl, wherein only two of the five atoms of the heteroaryl ring are independently nitrogen, oxygen, or sulfur. In certain embodiments, at least one $R^D$ is 5-membered monocyclic heteroaryl, wherein only three of the five atoms of the heteroaryl ring are independently nitrogen, oxygen, or sulfur. In certain embodiments, at least one $R^D$ is tetrazolyl. In certain embodiments, at least one $R^D$ is 6-membered monocyclic heteroaryl. In certain embodiments, at least one $R^D$ is 6-membered monocyclic heteroaryl, wherein only one of the six atoms of the heteroaryl ring is nitrogen. In certain embodiments, at least one $R^D$ is 6-membered monocyclic heteroaryl, wherein only two of the six atoms of the heteroaryl ring are nitrogen. In certain embodiments, at least one $R^D$ is triazinyl. In certain embodiments, at least one $R^D$ is tetrazinyl. In certain embodiments, at least one $R^D$ is bicyclic heteroaryl, wherein the point of attachment may be on any atom of the bicyclic heteroaryl ring system, as valency permits. In certain embodiments, at least one $R^D$ is a monocyclic heteroaryl ring fused with phenyl. In certain embodiments, at least one $R^D$ is a 5-membered monocyclic heteroaryl ring fused with phenyl. In certain embodiments, at least one $R^D$ is a 6-membered monocyclic heteroaryl ring fused with phenyl. In certain embodiments, at least one $R^D$ is a monocyclic heteroaryl ring fused with another monocyclic heteroaryl. In certain embodiments, at least one $R^D$ is a 5-membered monocyclic heteroaryl ring fused with another 5-membered monocyclic heteroaryl. In certain embodiments, at least one $R^D$ is a 5-membered monocyclic heteroaryl ring fused with a 6-membered monocyclic heteroaryl ring. In certain embodiments, at least one $R^D$ is a 6-membered monocyclic heteroaryl fused with another 6-membered monocyclic heteroaryl. In certain embodiments, at least one $R^D$ is —$OR^{D1}$. In certain embodiments, at least one $R^D$ is -OMe. In certain embodiments, at least one $R^D$ is -OEt. In certain embodiments, at least one $R^D$ is -OPr. In certain embodiments, at least one $R^D$ is -OBu. In certain embodiments, at least one $R^D$ is —O(pentyl). In certain embodiments, at least one $R^D$ is —O(hexyl). In certain embodiments, at least one $R^D$ is -OPh. In certain embodiments, at least one $R^D$ is -OBn. In certain embodiments, at least one $R^D$ is —$O(CH_2)_2Ph$. In certain embodiments, at least one $R^D$ is —OH. In certain embodiments, at least one $R^D$ is —$SR^{D1}$. In certain embodiments, at least one $R^D$ is —SH. In certain embodiments, at least one $R^D$ is —$N(R^{D1})_2$. In certain embodiments, at least one $R^D$ is —$NH_2$. In certain embodiments, at least one $R^D$ is —CN. In certain embodiments, at least one $R^D$ is —SCN. In certain embodiments, at least one $R^D$ is —$C(=NR^{D1})R^{D1}$, —$C(=NR^{D1})OR^{D1}$, or —$C(=NR^{D1})N(R^{D1})_2$. In certain embodiments, at least one $R^D$ is —$C(=O)R^{D1}$, —$C(=O)OR^{D1}$, or —$C(=O)N(R^{D1})_2$. In certain embodiments, at least one $R^D$ is —$NO_2$. In certain embodiments, at least one $R^D$ is —$NR^{D1}C(=O)R^{D1}$, —$NR^{D1}C(=O)OR^{D1}$, or —$NR^{D1}C(=O)N(R^{D1})_2$. In certain embodiments, at least one $R^D$ is —$OC(=O)R^{D1}$, —$OC(=O)OR^{D1}$, or —$OC(=O)N(R^{D1})_2$. In certain embodiments, at least one $R^D$ is a nitrogen protecting group when attached to a nitrogen atom. In certain embodiments, at least one $R^D$ is Bn, BOC, Cbz, Fmoc, trifluoroacetyl, triphenylmethyl, or Ts when attached to a nitrogen atom.

When $R^C$ of compounds of Formula (I) is heteroaryl substituted with two or more $R^D$ groups, two $R^D$ groups may be joined to form a substituted or unsubstituted carbocyclic ring. In certain embodiments, two $R^D$ groups are joined to form a substituted or unsubstituted cyclopropyl ring. In certain embodiments, two $R^D$ groups are joined to form a substituted or unsubstituted cyclobutyl ring. In certain embodiments, two $R^D$ groups are joined to form a substituted or unsubstituted cyclopentyl ring. In certain embodiments, two $R^D$ groups are joined to form a substituted or unsubstituted cyclohexyl ring. In certain embodiments, two $R^D$ groups are joined to form a substituted or unsubstituted cycloheptyl ring. In certain embodiments, two $R^D$ groups are joined to form a substituted or unsubstituted cyclooctyl ring. In certain embodiments, two $R^D$ groups are joined to form a substituted or unsubstituted cyclononyl ring. In certain embodiments, two $R^D$ groups are joined to form a substituted or unsubstituted cyclodecyl ring.

When $R^C$ of compounds of Formula (I) is heteroaryl substituted with two or more $R^D$ groups, two $R^D$ groups are joined to form a substituted or unsubstituted heterocyclic ring. In certain embodiments, two $R^D$ groups are joined to form a substituted or unsubstituted 4-membered heterocyclic ring. In certain embodiments, two $R^D$ groups are joined to form a substituted or unsubstituted 5-membered heterocyclic ring. In certain embodiments, two $R^D$ groups are joined to form a substituted or unsubstituted 6-membered heterocyclic ring. In certain embodiments, two $R^D$ groups are joined to form a substituted or unsubstituted 7-membered heterocyclic ring. In certain embodiments, two $R^D$ groups are joined to form a substituted or unsubstituted 8-membered heterocyclic ring. In certain embodiments, two $R^D$ groups are joined to form a substituted or unsubstituted 9-membered heterocyclic ring. In certain embodiments, two $R^D$ groups are joined to form a substituted or unsubstituted 10-membered heterocyclic ring.

When $R^C$ of compounds of Formula (I) is heteroaryl substituted with two or more $R^D$ groups, two $R^D$ groups are joined to form a substituted or unsubstituted aryl ring. In certain embodiments, two $R^D$ groups are joined to form a substituted or unsubstituted monocyclic aryl ring. In certain embodiments, two $R^D$ groups are joined to form a substituted or unsubstituted phenyl ring. In certain embodiments, two $R^D$ groups are joined to form a substituted or unsubstituted bicyclic aryl ring. In certain embodiments, two $R^D$ groups are joined to form a substituted or unsubstituted naphthyl ring.

When $R^C$ of compounds of Formula (I) is heteroaryl substituted with two or more $R^D$ groups, two $R^D$ groups are joined to form a substituted or unsubstituted heteroaryl ring. In certain embodiments, two $R^D$ groups are joined to form a substituted or unsubstituted monocyclic heteroaryl ring. In certain embodiments, two $R^D$ groups are joined to form a substituted or unsubstituted, 5-membered monocyclic heteroaryl ring. In certain embodiments, two $R^D$ groups are joined to form a substituted or unsubstituted, 6-membered monocyclic heteroaryl ring. In certain embodiments, two $R^D$ groups are joined to form a substituted or unsubstituted, bicyclic heteroaryl ring. In certain embodiments, two $R^D$ groups are joined to form a substituted or unsubstituted, 5,6-membered bicyclic heteroaryl ring. In certain embodiments, two $R^D$ groups are joined to form a substituted or unsubstituted, 6,5-membered bicyclic heteroaryl ring. In certain embodiments, two $R^D$ groups are joined to form a substituted or unsubstituted, 6,6-membered bicyclic heteroaryl ring.

In certain embodiments, $R^{D1}$ is H. In certain embodiments, $R^{D1}$ is substituted acyl. In certain embodiments, $R^{D1}$ is unsubstituted acyl. In certain embodiments, $R^{D1}$ is acetyl. In certain embodiments, $R^{D1}$ is substituted alkyl. In certain embodiments, $R^{D1}$ is unsubstituted alkyl. In certain embodiments, $R^{D1}$ is $C_{1-6}$ alkyl. In certain embodiments, $R^{D1}$ is methyl. In certain embodiments, $R^{D1}$ is ethyl. In certain embodiments, $R^{D1}$ is propyl. In certain embodiments, $R^{D1}$ is butyl. In certain embodiments, $R^{D1}$ is pentyl. In certain embodiments, $R^{D1}$ is hexyl. In certain embodiments, $R^{D1}$ is substituted alkenyl. In certain embodiments, $R^{D1}$ is unsubstituted alkenyl. In certain embodiments, $R^{D1}$ is vinyl. In certain embodiments, $R^{D1}$ is substituted alkynyl. In certain embodiments, $R^{D1}$ is unsubstituted alkynyl. In certain embodiments, $R^{D1}$ is ethynyl. In certain embodiments, $R^{D1}$ is substituted carbocyclyl. In certain embodiments, $R^{D1}$ is unsubstituted carbocyclyl. In certain embodiments, $R^{D1}$ is cylcopropyl. In certain embodiments, $R^{D1}$ is cylcobutyl. In certain embodiments, $R^{D1}$ is cyclopentyl. In certain embodiments, $R^{D1}$ is cyclohexyl. In certain embodiments, $R^{D1}$ is cycloheptyl. In certain embodiments, $R^{D1}$ is substituted heterocyclyl. In certain embodiments, $R^{D1}$ is unsubstituted heterocyclyl. In certain embodiments, $R^{D1}$ is substituted aryl. In certain embodiments, $R^{D1}$ is unsubstituted aryl. In certain embodiments, $R^{D1}$ is substituted phenyl. In certain embodiments, $R^{D1}$ is unsubstituted phenyl. In certain embodiments, $R^{D1}$ is substituted heteroaryl. In certain embodiments, $R^{D1}$ is unsubstituted heteroaryl. In certain embodiments, $R^{D1}$ is substituted pyridyl. In certain embodiments, $R^{D1}$ is unsubstituted pyridyl. In certain embodiments, $R^{D1}$ is a nitrogen protecting group when attached to a nitrogen atom. In certain embodiments, $R^{D1}$ is Bn, Boc, Cbz, Fmoc, trifluoroacetyl, triphenylmethyl, or Ts when attached to a nitrogen atom. In certain embodiments, $R^{D1}$ is an oxygen protecting group when attached to an oxygen atom. In certain embodiments, $R^{D1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D1}$ is a sulfur protecting group when attached to a sulfur atom. In certain embodiments, $R^{D1}$ is acetamidomethyl, t-Bu, 3-nitro-2-pyridine sulfenyl, 2-pyridine-sulfenyl, or triphenylmethyl when attached to a sulfur atom. In certain embodiments, two $R^{D1}$ groups are joined to form a substituted heterocyclic ring. In certain embodiments, two $R^{D1}$ groups are joined to form an unsubstituted heterocyclic ring. In certain embodiments, two $R^{D1}$ groups are joined to form a substituted heteroaryl ring. In certain embodiments, two $R^{D1}$ groups are joined to form an unsubstituted heteroaryl ring.

In certain embodiments, p is 0. In certain embodiments, p is 1. In certain embodiments, p is 2. In certain embodiments, p is 3. In certain embodiments, p is 4.

In certain embodiments, the compound of Formula (I) is of the formula:

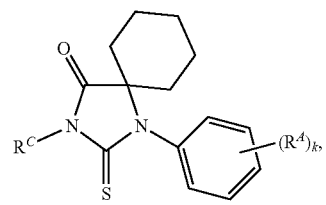

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

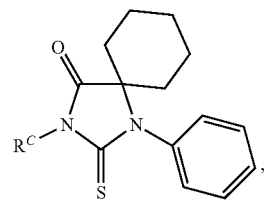

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

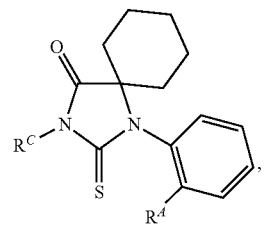

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

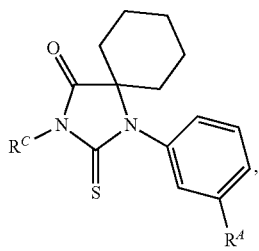

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

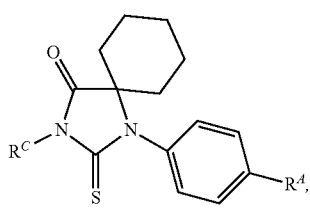

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

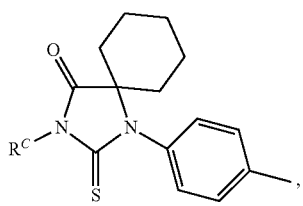

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

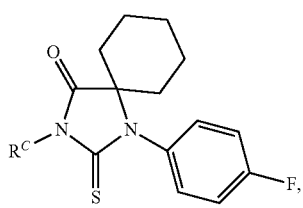

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

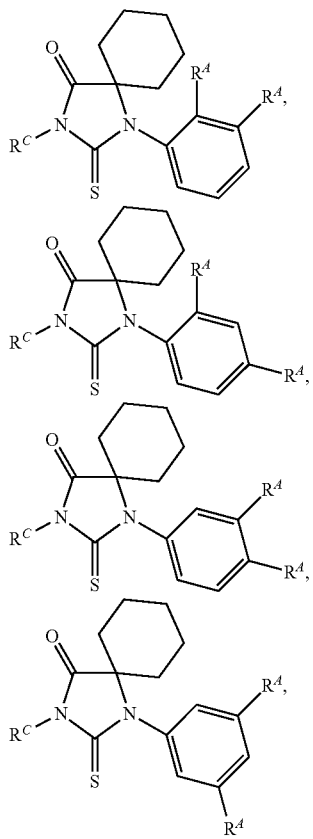

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

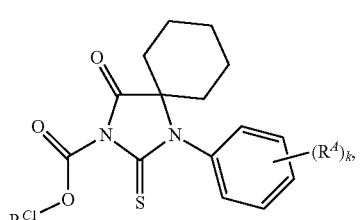

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

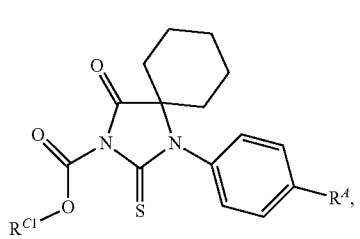

In certain embodiments, the compound of Formula (I) is of the formula:

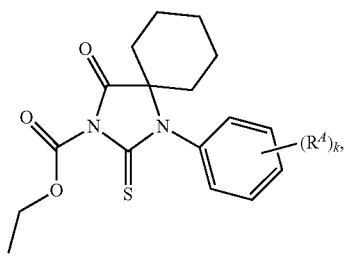

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

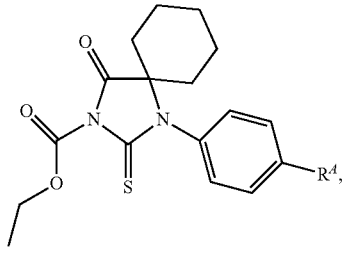

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

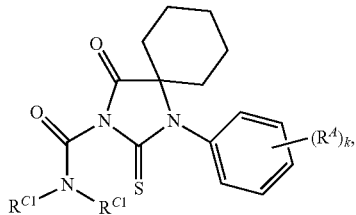

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

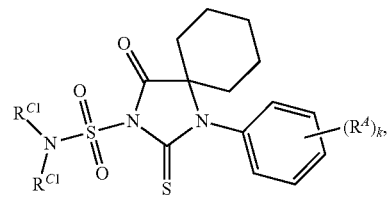

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

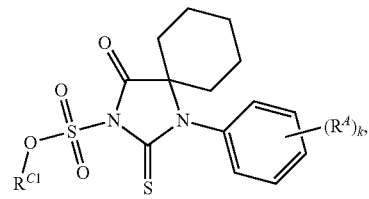

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

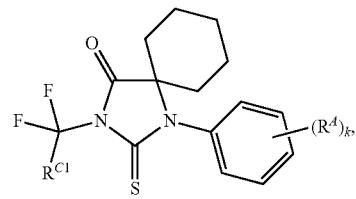

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

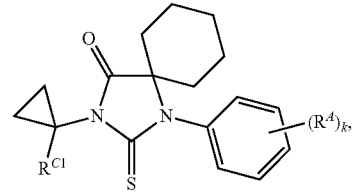

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

(I-A-1)
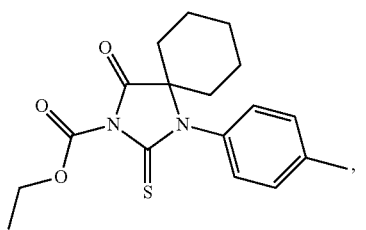
(I-A-2)
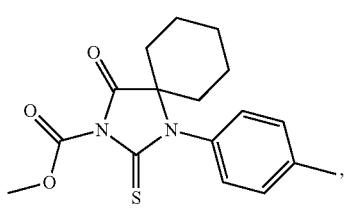
(I-A-3)
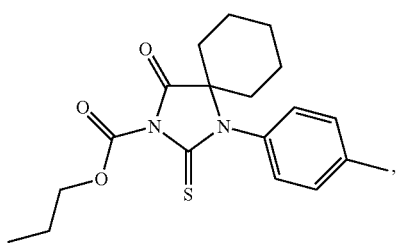
(I-A-4)
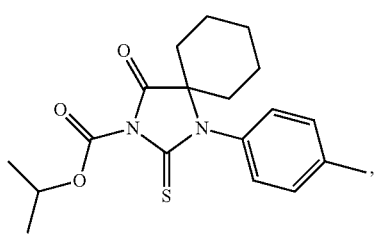
(I-A-5)
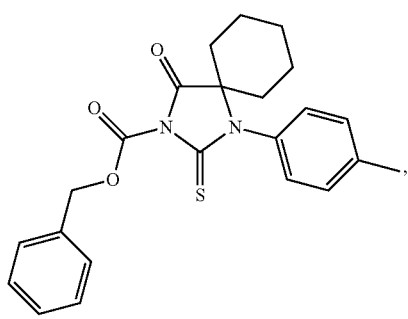
(I-A-6)
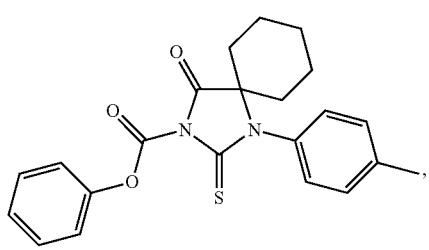
(I-A-7)
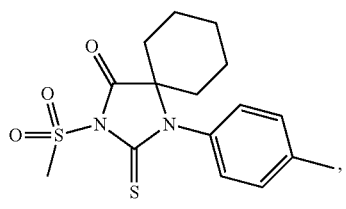
(I-A-8)
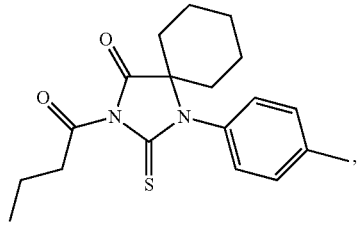
(I-A-9)
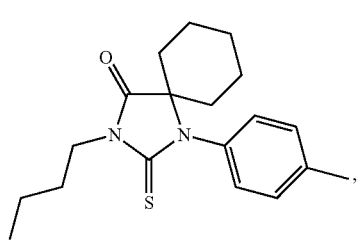
(I-A-10)
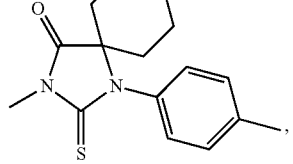
(I-A-11)
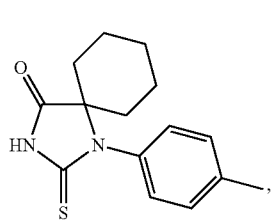
(I-B-2)
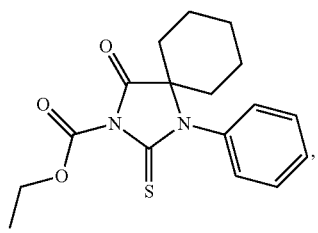
(I-B-3)
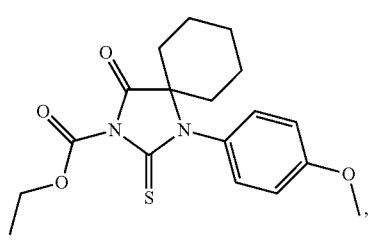

(I-B-4)
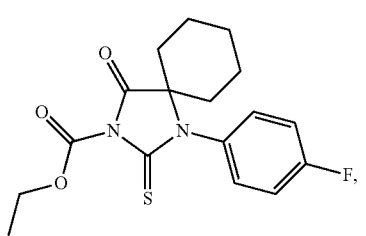

(I-B-5)
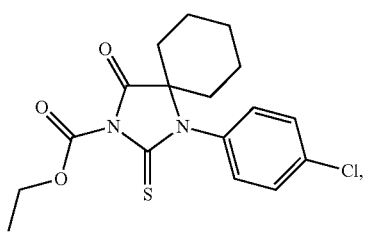

(I-B-6)
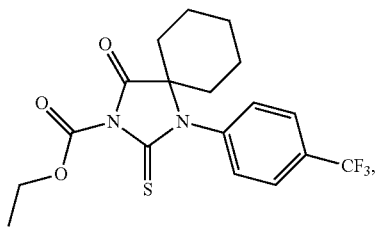

(I-B-7)
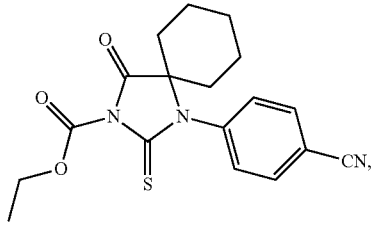

(I-B-8)
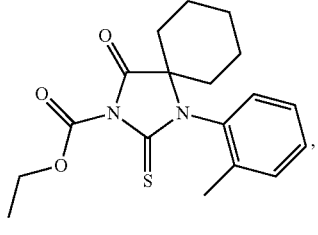

(I-B-9)
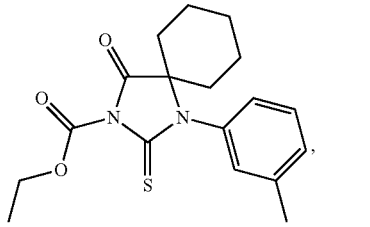

(I-B-10)
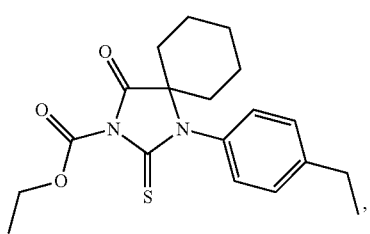

(I-B-11)
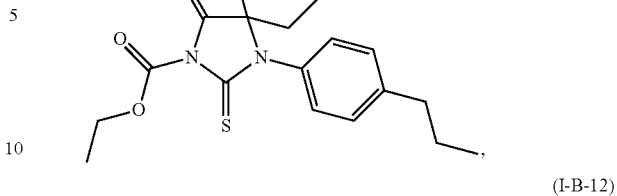

(I-B-12)
(I-B-13)
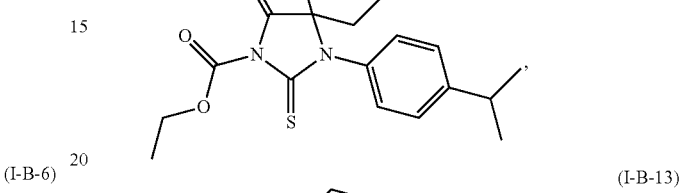

(I-B-14)
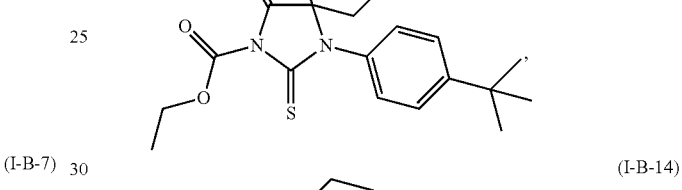

(I-C-3)
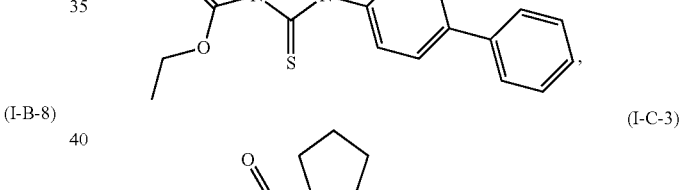

or a pharmaceutically acceptable salt, solvate, hydrate, polymorph, co-crystal, tautomer, stereoisomer, isotopically labeled derivative, or prodrug thereof.

In certain embodiments, the compound of Formula (I) is not of Formula (I-A-1), or a pharmaceutically acceptable salt, solvate, hydrate, polymorph, co-crystal, tautomer, stereoisomer, isotopically labeled derivative, or prodrug thereof.

The compounds described herein (e.g., compounds of Formula (I)) are shown to be antifungal agents, antiprotozoan, and/or chemosensitizers. In certain embodiments, the provided compounds are useful for reversing drug (e.g., fluconazole) resistance in fungi. In certain embodiments, the provided compounds are useful for reversing drug resistance in protozoa. Without wishing to be bound by a particular theory, these compounds may act by inhibiting the activity of fungal or protozoan mitochondrial phosphate carrier protein. In certain embodiments, the compound inhibits the activity of fungal or protozoan mitochondrial phosphate carrier protein without inhibiting, or at least not substantially, inhibiting the activity of the host's mitochondrial phosphate carrier protein (e.g., human phosphate carrier protein). In certain embodiments, the compounds described herein are specific antifungal agents, that is, for example, the compounds described herein do not inhibit normal enzymatic activity in a subject (e.g., a human), biological sample, or plant as much as the compounds inhibit the analogous activity in a fungus or protozoon. Thus, in some embodiments, it is desired that the compounds have high specificity for the fungal or protozoan target. The specificity of the inhibitor may be evaluated by comparing the $IC_{50}$ value with respect to the fungal or protozoan enzyme (i.e., target $IC_{50}$) as compared to that of the analogous host (e.g., human) enzyme (i.e., anti-target $IC_{50}$). An $IC_{50}$ value is defined as the concentration of the compound required to inhibit 50% of the enzymatic activity (e.g., mitochondrial phosphate carrier protein activity). In certain embodiments, the compound described herein exhibits an $IC_{50}$ value of <100 µM. In certain other embodiments, the compound exhibits an $IC_{50}$ value of <50 µM. In certain other embodiments, the compound exhibits an $IC_{50}$ value of <40 µM. In certain other embodiments, the compound exhibits an $IC_{50}$ value of <30 µM. In certain other embodiments, the compound exhibit an $IC_{50}$ value of <20 µM. In certain other embodiments, the compound exhibits an $IC_{50}$ value of <10 µM. In certain other embodiments, the compounds exhibit $IC_{50}$ values<7.5 µM. In certain embodiments, the compound exhibits an $IC_{50}$ value of <5 µM. In certain other embodiments, the compound exhibits an $IC_{50}$ value of <2.5 µM. In certain embodiments, the compound exhibits an $IC_{50}$ value of <1 µM. In certain embodiments, the compound exhibits an $IC_{50}$ value of <0.75 µM. In certain embodiments, the compound exhibits an $IC_{50}$ value of <0.5 µM. In certain embodiments, the compound exhibits an $IC_{50}$ value of <0.25 µM. In certain embodiments, the compound exhibits an $IC_{50}$ value of <0.15 µM. In certain embodiments, the compound exhibits an $IC_{50}$ value of <0.1 µM. In certain other embodiments, the compound exhibit an $IC_{50}$ value of <75 nM. In certain other embodiments, the compound exhibits $IC_{50}$ value of <50 nM. In certain other embodiments, the compound exhibits an $IC_{50}$ value of <5 nM. In certain other embodiments, the compound exhibits $IC_{50}$ value of <10 nM. In other embodiments, the compound exhibits an $IC_{50}$ values of <7.5 nM. In other embodiments, the compound exhibits an $IC_{50}$ value of <5 nM.

In certain embodiments, the compound inhibits the fungal and/or protozoan enzyme at a concentration at least 2-fold, 5-fold, 10-fold, 50-fold, 100-fold, 500-fold, or 1000-fold lower than the concentration needed to inhibit the host's analogous enzyme to the same extent. In certain embodiments, the enzyme being inhibited is mitochondrial phosphate carrier protein.

In certain embodiments, the compound exhibits an $IC_{50}$ value of <100 nM when combined with an additional pharmaceutical agent. In certain embodiments, the compound exhibits an $IC_{50}$ value of <80 nM when combined with an additional pharmaceutical agent. In certain embodiments, the compound exhibits an $IC_{50}$ value of <60 nM when combined with an additional pharmaceutical agent. In certain embodiments, the compound exhibits an $IC_{50}$ value of <40 nM when combined with an additional pharmaceutical agent. In certain embodiments, the compound exhibits an $IC_{50}$ value of <20 nM when combined with an additional pharmaceutical agent. In certain embodiments, the compound exhibits an $IC_{50}$ value of <10 nM when combined with an additional pharmaceutical agent. In certain embodiments, the additional pharmaceutical agent is another antifungal agent (e.g., an azole, e.g., fluconazole) or another antiprotozoan agent.

Provided herein are methods for the identification of fungal or protozoan-selective inhibitors of the MIR1 mitochondrial phosphate transporter by chemical screening. For example, in one embodiment, the method uses a *S. cerevisiae* BY4741 mir1 deletion strain, which cannot grow on media containing glycerol as a sole carbon source. To restore mitochondrial phosphate transport and growth on glycerol media through Mir1 activity, a gene encoding for a mitochondrial phosphate transporter is transformed into this strain. This gene may be either fungal or protozoan phosphate transporter genes (including, but not limited to, Mir1 homologs from *Saccharomyces cerevisiae* (NCBI gene ID 85340) or *Candida albicans* (NCBI gene Id 3635000) or human SLC25A3 (NCBI gene ID 5250). Specific mutations of the yeast or human MIR1 or SLC25A3 gene (including *S. cerevisiae* N184T mutant) may be included to optimize expression or function of the protein in yeast. In this method, strains expressing one of these genes are assayed for growth in the presence of screening compounds or thiohydantoin analogs to identify compounds that inhibit growth of strains expressing MIR1 of pathogens but not inhibit growth of strains expressing human SLC25A3.

In addition or alternatively, mitochondria are purified from these or other strains expressing different mitochondrial phosphate transporters and specific inhibition of mitochondrial phosphate transport activity is assayed. Mitochondrial phosphate uptake inhibition is measured by using an in vitro 32P method (see, e.g., Zara V, Dietmeier K, Palmisano A, et al. Yeast mitochondria lacking the phosphate carrier/p32 are blocked in phosphate transport but can import preproteins after regeneration of a membrane potential. Mol Cell Biol. 1996; 16(11):6524-31), in which 32P phosphoric acid is added to the purified mitochondria in the presence of the screening compounds to be tested, and phosphate accumulation is measured by $^{32}P$ radioactivity counts in mitochondrial pellets after centrifugation.

The exogenously introduced gene (e.g., human SLC25A3) may be codon optimized for expression in the fungal or protozoal cell in which it is to be expressed. Additionally or alternately, the gene encoding a human mitochondrial phosphate transporter may be modified to omit at least a portion of the human mitochondrial targeting sequence or to encode a fungal or protozoal mitochondrial targeting sequence (MTS) instead of or in addition to at least a portion of the human mitochondrial targeting sequence. Without wishing to be bound by any theory, doing so may enhance proper mitochondrial membrane localization of the protein when expressed in fungal or protozoal cells. The MIR1 protein is normally localized to the inner mitochondrial membrane (IMM). In one embodiment, a targeting sequence from any fungal (or protozoal) protein that is localized to the IMM for purposes of achieving appropriate localization of the human homolog is used. The predicted mitochondrial targeting sequence of SLC25A3 is within the N-terminal 49 amino acids. In some embodiments, an N-terminal region of varying lengths, e.g., about the first 20, 25, 30, 35, 40, 45, 50 amino acids. In another embodiment, a chimeric MIR1 protein can be used.

Pharmaceutical Compositions, Kits, and Administration

The present invention also provides pharmaceutical compositions comprising a compound described herein, or a pharmaceutically acceptable salt, solvate, hydrate, polymorph, co-crystals, tautomer, stereoisomer, isotopically labeled derivative, or prodrug thereof, and optionally a pharmaceutically acceptable excipient.

In certain embodiments, the compound described herein, or a pharmaceutically acceptable salt, solvate, hydrate, polymorph, co-crystal, tautomer, stereoisomer, isotopically labeled derivative, or prodrug thereof, is provided in an effective amount in the pharmaceutical composition. In certain embodiments, the effective amount is a therapeutically effective amount. In certain embodiments, the effective amount is a prophylactically effective amount. In certain embodiments, the effective amount is an amount useful for the treatment and/or prevention of a fungal or protozoan infection. The effective amount of the compound in the composition may be useful for the treatment and/or prevention of a fungal or protozoan infection as a single agent or in combination with another agent such as another antifungal agent (e.g., fluconazole) or another antiprotozoan agent. In certain embodiments, the effective amount is an amount useful for inhibiting the activity of a fungal or protozoan enzyme. In certain embodiments, the effective amount is an amount useful for killing a fungus or inhibiting the growth of a fungus. An effective amount of a compound may vary from about 0.001 mg/kg to about 1000 mg/kg in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

Pharmaceutical compositions described herein can be prepared by any method known in the art of pharmacology. In general, such preparatory methods include the steps of bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer P-188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier or excipient and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Alternatively or additionally, conventional syringes can be used in the classical mantoux method of intradermal administration. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds described herein may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., potency and/or efficacy in inhibiting one or more fungal or protozoan enzymes), bioavailability, reduce and/or modify their metabolism, inhibit their excretion, and/or modify their distribution within the body of a subject. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agent(s) and/or the desired therapeutic and/or prophylactic effect to be achieved. In general, it is expected that the additional pharmaceutical agent(s) utilized in combination be utilized at levels that do not exceed the levels at which they are utilized individually. In some embodiments, the levels utilized in combination will be lower than those utilized individually.

Exemplary additional pharmaceutical agents include, but are not limited to, antifungal agents, antiprotozoan agents, anti-bacterial agents, anti-viral agents, anti-inflammatory agents, and pain-relieving agents. The antifungal agents that may be used in combination with the compounds described herein include, but are not limited to, polyene antifungal agents (e.g., amphotericin B, candicidin, filipin, hamycin, natamycin, nystatin, rimocidin) and azole antifungal agents (e.g., imidazole antifungal agents (e.g., bifonazole, butoconazole, clotrimazole, econazole, fenticonazole, isoconazole, ketoconazole, miconazole, omoconazole, oxiconazole, sertaconazole, sulconazole, tioconazole), triazole antifungal agents (e.g., albaconazole, fluconazole, isavuconazole, itraconazole, posaconazole, ravuconazole, terconazole, voriconazole), and thiazole antifungal agents (e.g., abafungin). In certain embodiments, the antifungal agents are antifungal agents against which resistance is developed by the target fungus. Exemplary antiprotozoan agents include, but are not limited to, eflornithine, furazolidone, melarsoprol, metronidazole, ornidazole, paromomycin sulfate, pentamidine, pyrimethamine, tinidazole, artemisinin, artesunate, atovaquone, chloroquine, amodiaquine, lumefantrine, mefloquine, sulfadoxine, dihydroartemisinin, piperaquine, quinine, primaquine, suramin, fexinidazole, nifurtimox, and nitazoxanide. In some embodiments, an antiprotozoan agent is a lincosamide antibiotic, such as clindamycin. In some embodiments, an antiprotozoan agent is a macrolide antibiotic, such as azithromycin. In certain embodiments, the antiprotozoan agents are antiprotozoan agents against which resistance is developed by the target protozoon. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the first container and the second container are combined to form one unit dosage form.

Thus, in one aspect, provided are kits including a first container comprising a compound described herein, or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the kits described herein are useful in preventing and/or treating a fungal or protozoan infection in a subject. In certain embodiments, the kits are useful in inhibiting the activity of a fungal or protozoan enzyme (e.g., mitochondrial phosphate carrier protein) in a subject or biological sample. In certain embodiments, the kits are useful in killing a fungus or inhibiting the growth of a fungus. In certain embodiments, the kits are useful in killing a protozoon or inhibiting the growth of a protozoon. In certain embodiments, the kits further include instructions for administering the compound, or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the kits and instructions provide for treating and/or preventing a fungal or protozoan infection. In certain embodiments, the kits and instructions provide for inhibiting the activity of a fungal or protozoan enzyme. In certain embodiments, the kits and instructions provide for killing a fungus or inhibiting the growth of a fungus. In certain embodiments, the kits and instructions provide for killing a protozoon or inhibiting the growth of a protozoon. The kit may include one or more additional pharmaceutical agents described herein (such as antifungal agents (e.g., azole antifungal agents (e.g., fluconazole) and polyene antifungal agents (e.g., amphotericin B)) and/or antiprotozoan agents as a separate composition.

Methods of Treatment and Uses

In one aspect, the present invention provides methods for the treatment and/or prevention of a fungal or protozoan infection in a subject. In certain embodiments, the infection in the subject is caused by a fungus. In certain embodiments, the fungus is yeast. In certain embodiments, the fungus is a mold. In certain embodiments, the fungus that causes the fungal infection is a *Candida* species. In certain embodiments, the fungus is a *Candida albicans* strain. In certain embodiments, the fungus is *Candida albicans* CaCi-2. In certain embodiments, the fungus is *Candida albicans* CaCi-17. In certain embodiments, the fungus is *Candida albicans* strain 90028. In certain embodiments, the fungus is *Candida albicans* strain Gu5. In certain embodiments, the fungus is *Candida albicans* strain CTBT. In certain embodiments, the fungus is a *Candida glabrata* strain. Additional *Candida* species include, but are not limited to, *C. krusii, C. rugosa, C. parapsilosis, C. tropicalis, C. dubliniensis, C. lusitaniae, C. guilliermondii, C. famata, C. kefyr, C. pelliculosa, C. lipolytica, C. inconspicua, C. sake, C. lambica, C. norvegensis,* and *C. zeylanoides.* In certain embodiments, the fungus is a *Saccharomyces* species. In certain embodiments, the fungus is a *Saccharomyces cerevisiae* strain. In certain embodiments, the fungus is *Saccharomyces cerevisiae* W303 reporter strain (ATCC 208352). Additional *Saccharomyces* species include, but are not limited to, *Saccharomyces bayanus, Saccharomyces boulardii, Saccharomyces bulderi, Saccharomyces cariocanus, Saccharomyces cariocus, Saccharomyces chevalieri, Saccharomyces dairenensis, Saccharomyces ellipsoideus, Saccharomyces eubayanus, Saccharomyces exiguus, Saccharomycesflorentinus, Saccharomyces kluyveri, Saccharomyces martiniae, Saccharomyces monacensis, Saccharomyces norbensis, Saccharomyces paradoxus, Saccharomyces pastorianus, Saccharomyces spencerorum, Saccharomyces turicensis, Saccharomyces unisporus, Saccharomyces uvarum,* and *Saccharomyces zonatus.* In certain embodiments, the fungus is a *Aspergillus* species. In certain embodiments, the fungus is a *Aspergillus terreus* strain. Additional *Aspergillus* species include, but are not limited to, *A. clavatus, A. fumigatus, A. niger,* and *A. flavus.* In certain embodiments, the fungus is a *Cryptococcus* species. In certain embodiments, the fungus is a *Histoplasma* species. In certain embodiments, the fungus is a *Rhizopus* species. In certain embodiments, the fungus is a *Mucor* species. In some embodiments, the fungus is a member of the genus *Coccidioides.* In some embodiments, the fungus is a member of the phylum Ascomycota. In some embodiments, the fungus is a member of the phylum Basidiomycota. In some embodiments, the fungus is a member of the phylum Chytridiomycota. In some embodiments, the fungus is a member of the phylum Glomeromycota. In some embodiments, the fungus is a member of the phylum Zygomycota. The fungus may be any fungus including, but not limited to, a member of a genus selected from the group consisting of *Aspergillus, Blastomyces, Candida, Coccidioides, Cryptococcus, Epidermophytum, Fusarium, Histoplasma, Malassezia, Microsporum, Mucor, Paracoccidioides, Pneumocystis, Pseudallescheria, Rhizopus, Scedosporium, Sporothrix, Stachybotrys, Saccharomyces, Trichophyton, Trichosporon, Bipolaris, Exserohilum, Curvularia, Alternaria,* and *Cladophialophora.*

In some embodiments, the fungus of the genus *Blastomyces* is *Blastomyces dermatitidis.* In some embodiments, the fungus of the genus *Coccidioides* is *Coccidioides immitis* or *Coccidioides posadasii.* In some embodiments, the fungus of the genus *Cryptococcus* is *Cryptococcus neoformans, C. gattii, C. albidus, C. laurentii,* or *C. uniguttulas.* In some embodiments, the fungus of the genus *Epidermophyton* is *E. floccosum.* In some embodiments, the fungus of the genus *Fusarium* is *Fusarium graminearum Fusarium oxysporum* fsp. *cubense,* a member of the *Fusarium solani* complex, *Fusarium oxysporum, Fusarium verticillioides,* or *Fusarium proliferatum.* In some embodiments, the fungus of the genus *Histoplasma* is *Histoplasma capsulatum.* In some embodiments, the fungus of the genus *Malassezia* is *Malassezia furfur.* In some embodiments, the fungus of the genus *Mucor* is *M. circinelloides.* In some embodiments, the fungus of the genus *Paracoccidioides* is *Paracoccidioides brasiliensis.* In some embodiments, the fungus of the genus *Penicillium* is *Penicillium marneffei.* In some embodiments, the fungus of the genus *Pichia* is *Pichia anomala, Pichia guilliermondi.* In some embodiments, the fungus of the genus *Pneumocystis* is *Pneumocystis carinii* or *Pneumocystis jirovecii.* In some embodiments, the fungus of the genus Pseudallescheria is Pseudallescheria *boydii.* In some embodiments, a parasite of the genus *Rhizopus* is *Rhizopus oryzae.* In some embodiments, the fungus of the genus *Rhodotorula* is *Rhodotorula rubra.* In some embodiments, the fungus of the genus *Scedosporium* is *Scedosporium apiospermum.* In some embodiments, the fungus of the genus *Schizophyllum* is *Schizophyllum commune.* In some embodiments, the fungus of the genus *Sporothrix* is *Sporothrix schenckii.* In some embodiments, the fungus of the genus *Trichophyton* is *Trichophyton mentagrophytes, Trichophyton rubrum, Trichophyton verrucosum, Trichophyton tonsurans,* or *Trichophyton violaceum.* In some embodiments, the fungus of the genus *Trichosporon* is *Trichosporon asahii, Trichosporon cutaneum, Trichosporon inkin,* or *Trichosporon mucoides.* In some embodiments, a member of the genus *Exserohilum* is *Exserohilum rostratum, E. meginnisii,* or *E. longirostratum.*

In certain embodiments, the fungus is a fungus resistant to one or more azole antifungal agents. In certain embodiments, the fungus is a fungus resistant to fluconazole. In certain embodiments, the fungus is a fungus resistant to one or more polyene antifungal agents. In certain embodiments, the fungus is a fungus resistant to amphotericin B.

In some embodiments, the fungus is a pathogen that affects one or more cultivated plants. In some embodiments, the fungus is a member of the genus *Magnaporthe, Ophiostoma, Cryphonectria, Thielaviopsis, Verticillium, Fusarium, Ustilago, Alternaria, Rhizoctonia, Phakospora, Puccinia,* or *Cochliobolus.* In some embodiments, a member of the genus *Plasmodium* is a causative agent of malaria, e.g., *Plasmodium falciparum, Plasmodium vivax, Plasmodium ovale curtisi, Plasmodium ovale wallikeri, Plasmodium malariae,* or *Plasmodium knowlesi.* In some embodiments, a member of the genus *Cryptosporidium* is *C. parvum, C. hominis, C. canis, C. felis, C. meleagridis,* or *C. muris.*

The protozoan infection in the subject may be caused by a protozoon. In some embodiments, the protozoon is an Apicomplexan, e.g., a member of the genus *Babesia, Plasmodium, Cryptosporidium, Isospora,* or *Toxoplasma.* In some embodiments, the member of the genus *Isospora* is *Isospora belli.* In some embodiments, the member of the genus *Babesia* is *Babesia microti* or *Babesia divergens.* In some embodiments, the protozoon is *Toxoplasma gondii.* In some embodiments, the protozoon is a member of a genus of amoebae. In some embodiments, the protozoon is a member of the genus *Entamoeba*. In some embodiments, a member of the genus *Entamoeba* is *Entamoeba histolytica*, *Entamoeba dispar*, or *Entamoeba moshkovskii*. In some embodiments, the protozoon is a member of the genus *Naegleria*, e.g., *Naegleria fowleri*. In some embodiments, the protozoon is a member of the genus *Balamuthia*, e.g., *Balamuthia mandriallaris*. In some embodiments, the protozoon is a member of the genus *Acanthameba*. In some embodiments, a member of the genus *Giardia* is *Giardia lamblia* (sometimes referred to as *Giardia duodenalis* or *Giardia intestinalis*). In certain embodiments, the protozoon is a member of genus *Sarcocystis*, e.g., *Sarcocystis bovohominis*, *Sarcocystis suihominis*, or *Sarcocystis bovicanis*. In certain embodiments, a protozoon is a member of genus *Cyclospora*, e.g., *Cyclospora cayetanensis*. In certain embodiments, the protozoon is a member of genus *Neospora*, e.g., *Neospora caninum*. In certain embodiments, the protozoon is a member of genus *Theileria*, e.g., *Theileria parva*. In certain embodiments, the protozoon is a member of genus *Trichomonas*, e.g., *Trichomonas vaginalis*. In some embodiments, the protozoon is a kinetoplastid. In some embodiments, a kinetoplastid is a trypanosomatid, e.g., a member of the genus *Leishmania* (e.g., *L. donovani, L. major, L. tropica*, or *L. braziliensis*) or a member of the genus *Trypanosoma* (e.g., *T. brucii, T. cruzii, T. congolense*, or *T. equiperdum*).

In certain embodiments, the compounds described herein, or a composition thereof, inhibits a eukaryotic parasite.

In certain embodiments, the compounds described herein, or a composition thereof, inhibits an enzyme of a microbial organism that requires mitochondrial respiratory function for virulence in a host of the microbial organism.

The compounds of the present invention, or pharmaceutical compositions thereof, may inhibit the fungal or protozoan mitochondrial phosphate carrier protein. In certain embodiments, the compounds described herein (e.g., compounds of Formula (I)), or pharmaceutical compositions thereof, inhibit the fungal or protozoan mitochondrial phosphate carrier protein with selectivity over the analogous human enzyme. This activity results in single-agent killing of pathogenic *Saccharomyces* molds. In vitro this activity sensitizes fungal or protozoan pathogens (e.g., *Candida albicans*) to the commonly used antifungal agents (e.g., azole antifungal agents (e.g., fluconazole) and polyene antifungal agents (e.g., amphotericin B)) and/or antiprotozoan agents, and it is hypothesized that these compounds would have enhanced activity in a whole animal model of infection. In addition, these compounds may have use in the control of agricultural fungal or protozoan pathogens.

In certain embodiments, the subject described herein is a human. In certain embodiments, the subject is an animal. The animal may be of either sex and may be at any stage of development. In certain embodiments, the subject is a fish. In certain embodiments, the subject is a mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal. In certain embodiments, the subject is immunocompromised. For example, the subject may have reduced immune system function as a result of a disease such as HIV infection, acquired immunodeficiency syndrome (AIDS), cancer (e.g., solid tumor or leukemia), bone marrow disorder, or a genetic immunodeficiency. In some embodiments, the subject is immunocompromised as a result of a medication, e.g., immunosuppressive therapy or chemotherapy, bone marrow transplant, stem cell transplant, or exposure to radiation. In some embodiments, reduced immune system function comprises neutropenia. In some embodiments, the subject suffers from a nosocomial fungal infection.

Another aspect of the present invention involves methods of preventing a fungal infection in a subject who was or may be exposed to a fungus. In certain embodiments, the subject has been exposed to a fungus. In certain embodiments, the subject may have been exposed to a fungus. In these circumstances, the subject may not have developed the signs or symptoms of a fungal infection.

Another aspect of the present invention involves methods of preventing a protozoan infection in a subject who was or may be exposed to a protozoon. In certain embodiments, the subject has been exposed to a protozoon. In certain embodiments, the subject may have been exposed to a protozoon. In these circumstances, the subject may not have developed the signs or symptoms of a protozoan infection.

In another aspect, the present invention provides methods of inhibiting the activity of a fungal enzyme in a subject or biological sample. All types of biological samples described herein or known in the art are contemplated as being within the scope of the invention. In certain embodiments, the activity inhibited by the inventive methods is the activity of fungal mitochondrial phosphate carrier protein.

In another aspect, the present invention provides methods of inhibiting the activity of a protozoan enzyme in a subject or biological sample. In certain embodiments, the activity inhibited by the inventive methods is the activity of protozoan mitochondrial phosphate carrier protein.

Another aspect of the present invention relates to methods of killing a fungus or inhibiting the growth of a fungus. In certain embodiments, the fungus is killed. In certain embodiments, the growth of the fungus is inhibited.

Another aspect of the present invention relates to methods of killing a protozoon or inhibiting the growth of a protozoon. In certain embodiments, the protozoon is killed. In certain embodiments, the growth of the protozoon is inhibited.

In certain embodiments, the methods described herein include administering to a subject, contacting a biological sample, or contacting a fungus and/or protozoon with an effective amount of a compound described herein, or a pharmaceutically acceptable salt, solvate, hydrate, polymorph, co-crystal, tautomer, stereoisomer, isotopically labeled derivative, or prodrug thereof, or a composition thereof. In certain embodiments, the methods described herein include administering to a subject, contacting a biological sample, or contacting a fungus and/or protozoon with an effective amount of a compound described herein, or a pharmaceutically acceptable salt thereof, or a composition thereof. In certain embodiments, the compound, or a composition thereof, is administered to a subject. In certain embodiments, the compound, or a composition thereof, is contacted with a biological sample. In certain embodiments, the compound, or a composition thereof, is contacted with a fungus and/or protozoon. In certain embodiments, the compound, or a composition thereof, is contacted with a fungus and/or protozoon in an agricultural setting. In certain embodiments, the compound, or a composition thereof, is contacted with a fungus and/or protozoon in an environmental setting. In certain embodiments, the compound, or a composition thereof, is contacted with a fungus and/or protozoon in a healthcare setting. In certain embodiments, the compound, or a composition thereof, is contacted with a fungus and/or protozoon in a clinical setting. In certain embodiments, the compound, or a composition thereof, is contacted with a fungus and/or protozoon in a research setting. In certain embodiments, the compound, or a composition thereof, is contacted with a fungus and/or protozoon in or on a subject.

In certain embodiments, the compound, or a composition thereof, is contacted with a fungus and/or protozoon in or on a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub. In certain embodiments, the compound is contacted with a leaf, branch, trunk, root, or seed. In some embodiments, the compound is contacted with a plant by spraying, dusting, introducing the compound into soil into which a seed is to be planted or has been planted or in which a plant is growing. A compound of the invention may be formulated with one or more vehicles appropriate for use in agricultural setting and/or may be present in a composition together with one or more other compounds useful for agricultural purposes, such as other antifungal and/or antiprotozoan agent(s). In some embodiments, a compound of the invention is used to inhibit fungal and/or protozoan growth on a harvested plant material, e.g., crops or seeds, which may be stored for future use. In certain embodiments, the compound, or a composition thereof, is contacted with a fungus and/or protozoon in or on the soil. In certain embodiments, the compound, or a composition thereof, is contacted with a fungus and/or protozoon in water. The compounds described herein may be capable of killing or controlling various fungi and/or protozoa without adversely affecting plants, such as cultivated plants. The compounds described herein may also be readily decomposable and/or may present no substantial acute and chronic toxicity to mammals, such as humans.

The methods of the present invention may further comprise administering to a subject, contacting a biological sample, or contacting a fungus and/or protozoon with one or more additional pharmaceutical agents in combination with a compound described herein, or a pharmaceutically acceptable salt, solvate, hydrate, polymorph, co-crystal, tautomer, stereoisomer, isotopically labeled derivative, or prodrug thereof, or composition thereof. In certain embodiments, the additional pharmaceutical agents are as described herein. The additional pharmaceutical agent may be an antifungal agent. In certain embodiments, the additional pharmaceutical agent is an azole antifungal agent. In certain embodiments, the additional pharmaceutical agent is fluconazole. In certain embodiments, the additional pharmaceutical agent is a polyene antifungal agent. In certain embodiments, the additional pharmaceutical agent is amphotericin B. The additional pharmaceutical agent may also be an antiprotozoal agent. In certain embodiments, the additional pharmaceutical agent is an inhibitor of fungal and/or protozoan mitochondrial phosphate carrier protein.

In certain embodiments, the additional pharmaceutical agent inhibits synthesis of a component of the fungal plasma membrane, such as ergosterol. In certain embodiments, the additional pharmaceutical agent inhibits a fungal enzyme. In certain embodiments, the fungal enzyme is involved in synthesis of a component of the fungal membrane. In certain embodiments, the enzyme is fungal lanosterol 14α-demethylase. In certain embodiments, the additional pharmaceutical agent is an allylamine. Allylamines inhibit squalene epoxidase, an enzyme required for ergosterol synthesis. In some embodiments, the allylamine is amorolfin, butenafine, naftifine, or terbinafine.

In certain embodiments, the additional pharmaceutical agent inhibits synthesis of a component of the fungal cell wall, such as fungal glucan. In some embodiments, the additional pharmaceutical agent inhibits fungal enzyme 1,3-β glucan synthase. In some embodiments, the additional pharmaceutical agent is an echinocandin, such as caspofungin, micafungin, or anidulafungin. In some embodiments, the additional pharmaceutical agent is a polyene antifungal agent, such as amphotericin B, amphotericin A, nystatin, candicidin, filipin, hamycin, natamycin, timocidin, filipin, pimaricin, rimocidin, eurocidin, candidin, perimycin, levorin, or trichomycin.

The inventive compounds or compositions may synergistically augment the fungal- and/or protozoan-inhibitory activity of the additional pharmaceutical agent(s). Therefore, the combination of the inventive compound and the additional pharmaceutical agent(s) may be useful in inhibiting the activity of a fungal and/or protozoan enzyme that is resistant to the additional pharmaceutical agent(s) in the absence the inventive compounds. The combination of the inventive compound and the additional pharmaceutical agent(s) may also be useful in treating and/or preventing a fungal and/or protozoan infection caused by a fungus and/or protozoon resistant to the additional pharmaceutical agent(s) in the absence of the inventive compound. The combination of the inventive compound and the additional pharmaceutical agent(s) may further be useful in killing a fungus and/or protozoon or inhibiting the growth of a fungus and/or protozoon resistant to the additional pharmaceutical agent(s) in the absence of the inventive compound. In some embodiments, resistance is innate resistance. In some embodiments, resistance is acquired resistance. Resistance may be acquired as a result of a mutation. In some embodiments, a mutation is in a gene that encodes a target of an antifungal and/or antiprotozoan agent or a gene in the same biosynthetic pathway. In some embodiments, a mutation is in a gene that encodes a transcription factor that results in overexpression of a target of an antifungal and/or antiprotozoan agent or a gene in the same biosynthetic pathway.

In certain embodiments, a compound of the invention or composition comprising such compound may be used to inhibit fungal and/or protozoan growth on or in an inanimate object or in an environment such as the interior of a building that may contain one or more fungal and/or protozoan cells or spores.

In some embodiments, the methods of the invention comprise detecting a fungus or protozoan. In some embodiments, the methods of the invention comprise diagnosing a subject as having a fungal infection or a protozoal infection. Methods for detecting fungi and protozoa, and methods for diagnosis of fungal or protozoal infections, are known in the art. In some embodiments, the methods of the invention comprise obtaining a sample and testing the sample for presence of a fungus, fungal product, protozoan, or protozoal product. In some embodiments, the methods of the invention comprise obtaining a biological sample from a subject and testing the sample for presence of a fungus, fungal product, protozoan, or protozoal product. In some embodiments, the methods of the invention comprise obtaining a biological sample from a subject and testing the sample for presence of an antibody to a fungus, protozoan, fungal antigen, or protozoal antigen. In some embodiments, a fungus produces a mycotoxin. In some embodiments, a sample is tested for presence of a mycotoxin. In some embodiments, a sample contains a mycotoxin.

In some embodiments, a sample comprises soil, plant material, dust, air, and/or water. In some embodiments, a sample is obtained from a food, beverage, or medication, In some embodiments, a sample is obtained by collecting a material from an inanimate object, e.g., an inanimate object found in a healthcare setting or environmental setting. In some embodiments, an inanimate object is a medical device, wall, floor, heating, air conditioning, or ventilating system.

Another aspect of the invention relates to methods of screening a library of compounds to identify one or more compounds that are useful in the methods of the invention. In certain embodiments, the one or more compounds identified are useful for treating and/or preventing a fungal and/or protozoan infection in a subject. In certain embodiments, the one or more compounds identified are useful for inhibiting the activity of a fungal and/or protozoan enzyme in a subject or biological sample. In certain embodiments, the one or more compounds identified are useful for killing a fungus or inhibiting the growth of a fungus. In certain embodiments, the one or more compounds identified are useful for killing a protozoon or inhibiting the growth of a protozoon. In certain embodiments, the library of compounds is a library of compounds described herein. In certain embodiments, the methods of screening a library include providing at least two different compounds described herein, or pharmaceutically acceptable salts, solvates, hydrates, polymorphs, co-crystals, tautomers, stereoisomers, isotopically labeled derivatives, or prodrugs thereof; and performing at least one assay using the different compounds described herein, to identify one or more compounds that potentiates the effect of an antifungal agent, reverses the resistance of a fungus to a particular antifungal agent, and/or that kills a fungus or inhibits the growth of a fungus. In certain embodiments, the methods of screening a library include providing at least two different compounds described herein, or pharmaceutically acceptable salts, solvates, hydrates, polymorphs, co-crystals, tautomers, stereoisomers, isotopically labeled derivatives, or prodrugs thereof; and performing at least one assay using the different compounds described herein, to identify one or more compounds that potentiates the effect of an antiprotozoan agent, reverses the resistance of a protozoon to a particular antiprotozoan agent, and/or that kills a protozoan or inhibits the growth of a protozoan.

In some aspects, the disclosure provides a method of identifying an antifungal agent or antiprotozoal agent, the method comprising identifying an agent that inhibits expression or activity of a fungal or protozoal mitochondrial phosphate carrier protein. In some embodiments the agent is identified in a high throughput screen. In some embodiments the agent does not substantially inhibit human SLC25A3. In some embodiments the agent does not substantially inhibit proliferation or survival of human cells. In some embodiments the agent has an $IC_{50}$ for SLC25A3 at least 5, 10, 20, 50, 100, 250, 500, or 1,000 times as great (or more) as its $IC_{50}$ for a fungal or protozoal mitochondrial carrier protein (e.g., MIR1).

In some embodiments the agent is a small molecule. In some aspects, a "small molecule" as used herein, is an organic molecule that is less than about 2 kilodaltons (kDa) in mass. In some embodiments, a small molecule is less than about 1.5 kDa, or less than about 1 kDa. In some embodiments, a small molecule is less than about 800 daltons (Da), 600 Da, 500 Da, 400 Da, 300 Da, 200 Da, or 100 Da. Often, a small molecule has a mass of at least 50 Da. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. Small molecules often comprise one or more cyclic carbon or heterocyclic structures and/or aromatic or polyaromatic structures, optionally substituted with one or more of the above functional groups.

In some embodiments the method of identifying comprises contacting isolated fungal or protozoal mitochondria with a test agent and assaying the ability of the test agent to inhibit phosphate transport into the mitochondria. In some embodiments isolated fungal or protozoal mitochondria are contacted with a test agent and labeled phosphate (optionally $^{32}$P-labeled phosphate), and the ability of the test agent to inhibit phosphate transport into the mitochondria is measured.

In some embodiments, the method of identifying comprises (a) contacting fungal or protozoal cells that have reduced or absent expression or activity of endogenous mitochondrial phosphate transporter polypeptide (e.g., that have a deletion or disruption of the endogenous MIR1 gene), wherein the cells are rescued by an introduced nucleic acid encoding a fungal or protozoal mitochondrial phosphate transporter polypeptide, with a test agent; (b) contacting fungal or protozoal cells that have reduced or absent expression or activity of endogenous mitochondrial phosphate transporter polypeptide (e.g., that have a deletion or disruption of the endogenous MIR1 gene), wherein the cells are rescued by an introduced nucleic acid encoding at least a portion of a mammalian, e.g., human, mitochondrial phosphate transporter polypeptide, with said test agent; and (c) identifying the test agent as an inhibitor of expression or activity of the fungal or protozoal mitochondrial phosphate transporter polypeptide if the test agent inhibits growth of fungal or protozoal cells of (a) but does not substantially inhibit growth of fungal or protozoal cells of (b). In some embodiments the cells are cultured in or on media that contains glycerol as the carbon source. In some embodiments the yeast cells have a deleted, disrupted, or otherwise disabled PIC2 gene (*S. cerevesiae* Gene ID: 856779; RefSeq accession numbers NM_001178944.3→NP_010973.3) or homolog thereof in a different fungal species or protozoal species. PIC2 encodes a second mitochondrial phosphate transporter that may provide a very slight rescue of the growth defect of MIR1 deletion strains. It may normally be expressed at a lower level than MIR1.

In some aspects, an agent identified using a method described herein may be considered a candidate antifungal or antiprotozoal agent. In some embodiments a method of identifying an antifungal agent or antiprotozoal agent further comprises testing the ability of a candidate antifungal agent identified as described herein to inhibit growth of a fungal or protozoal cells in vitro in vivo, or both. In some embodiments tests are performed using a test animal, e.g., a test mammal such as a rodent, e.g., a mouse, rat, hamster, or guinea pig, or a rabbit, or a non-human primate. In some embodiments test may be performed using an avian, bovine, ovine, porcine, or other mammalian species.

The different compounds described herein may be generated by synthetic methods such as combinatorial chemistry (see, e.g., Ecker et al., *Bio/Technology*, (1995) 13:351-360 and U.S. Pat. No. 5,571,902). In certain embodiments, the different compounds are provided by liquid-phase or solution synthesis. In certain embodiments, the different compounds are provided by solid-phase synthesis. In certain embodiments, the different compounds are provided by a high-throughput, parallel, or combinatorial synthesis. In certain embodiments, the different compounds are provided by a low-throughput synthesis. In certain embodiments, the different compounds are provided by a one-pot synthesis. The different compounds may be provided robotically or manually. In certain embodiments, the step of providing at least two different compounds of the present invention include arraying into at least two vessels at least two different compounds of the present invention wherein the compounds are bound to solid supports, cleaving the compounds from the solid supports, and dissolving the cleaved compounds in a solvent. The solid supports include, but do not limit to, beads (e.g., resin beads and magnetic beads), hollow fibers, solid fibers, plates, dishes, flasks, meshes, screens, and membranes. In certain embodiments, the solid supports are beads. In certain embodiments, one solid support is capable of supporting at least 50 nmol of a compound. In certain embodiments, one solid support is capable of supporting at least 100 nmol of a compound. In certain embodiments, one solid support is capable of supporting at least 200 nmol of a compound. Each vessel may contain one or more support-bound compounds of the present invention. In certain embodiments, each vessel contains one support-bound compounds of the present invention. The solid supports and/or the compounds may be labeled with one or more labeling agents for the identification or detection of the compounds. The vessels may be wells of a microtiter plate. The solvent may be an inorganic solvent, organic solvent, or a mixture thereof. The steps of arraying, cleaving, and dissolving may be performed robotically or manually.

Typically, the methods of screening a library of compounds involve at least one assay. In certain embodiments, the assay is performed to detect one or more characteristics associated with the treatment of a fungal or protozoan infection. The assay may be an immunoassay, such as a sandwich-type assay, competitive binding assay, one-step direct test, two-step test, or blot assay. The step of performing at least one assay may be performed robotically or manually.

In yet another aspect, the present invention provides the compounds described herein, and pharmaceutically acceptable salts, solvates, hydrates, polymorphs, co-crystals, tautomers, stereoisomers, isotopically labeled derivatives, prodrugs, and compositions thereof, for use in the treatment and/or prevention of a fungal or protozoan infection in a subject.

Another aspect of the present invention relates to the compounds described herein, and pharmaceutically acceptable salts, solvates, hydrates, polymorphs, co-crystals, tautomers, stereoisomers, isotopically labeled derivatives, prodrugs, and compositions thereof, for use in inhibiting the activity of a fungal or protozoan enzyme in a subject or biological sample.

In still another aspect, the present invention provides the compounds described herein, and pharmaceutically acceptable salts, solvates, hydrates, polymorphs, co-crystals, tautomers, stereoisomers, isotopically labeled derivatives, prodrugs, and compositions thereof, for use in killing a fungus or inhibiting the growth of a fungus.

In yet another aspect, the present invention provides the compounds described herein, and pharmaceutically acceptable salts, solvates, hydrates, polymorphs, co-crystals, tautomers, stereoisomers, isotopically labeled derivatives, prodrugs, and compositions thereof, for use in killing a protozoon or inhibiting the growth of a protozoan.

In certain embodiments, the provided compounds, or compositions thereof, are useful as a pesticide (e.g., a fungicide).

In certain embodiments, the provided compounds, or compositions thereof, are useful as a disinfectant.

In some embodiments, a compound described herein (e.g., a compound of Formula (I)) is tested in an animal model of a fungal or protozoan infection. For example, in some embodiments, a non-human animal such as a rodent (e.g., a mouse) or non-human primate is experimentally infected with a fungus or protozoan. A compound described herein is administered one or more times to the non-human animal. In some embodiments, an additional antifungal or antiprotozoan agent is also administered. The ability of the compound, or compound combination (i.e., the compound and the additional antifungal or antiprotozoan agent), to reduce mortality or morbidity due to the fungus or protozoan or to reduce fungal or protozoan burden in one or more organs, tissues, or the blood is assessed at one or more time points.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Example 1

Compounds Screening Strategy

The various metabolic pathways of medically relevant fungi have recently come under investigation for their roles in fungal pathogenicity and the acquisition of drug resistance (Shingu-Vazquez et al., *Eukaryot. Cell* 2011, 10(11): 1376-83; Martins et al., *J. Bioenerg. Biomembr.* 2011, 43(1):81-8). Specifically, the mitochondrion and its numerous components and functions are emerging as factors in determining the effectiveness of current antimycotic therapies in controlling human fungal infections. In vitro experiments have shown that loss of mitochondrial DNA (mtDNA) in *C. glabrata* correlates to increased resistance to azole antifungals (Brun et al., *J. Antimicrob. Chemother.* 2005, 56:307-314). Paradoxically, clinical isolates of azole-resistant *C. glabrata* rarely show impairment of mtDNA function. The significance of the seemingly contradictory in vitro assays remains to be seen (Bouchara et al., *J. Med. Microbiol.* 2000, 49(11):977-84; Ferrari et al., *PLoS Pathog.* 2009, 5(1):e1000268).

The importance of mitochondrial function to fungal virulence is no better understood. *C. glabrata* with dysfunctional or missing mtDNA, also known as petite strains, are documented as being less pathogenic than non-petite strains (Brun et al., *J. Antimicrob. Chemother.* 2005, 56:307-314). However, this observation is only reproducible when the genetic damage is artificially induced with chemical reagents such as ethidium bromide. The work of Ferrari et al.

showed the *C. glabrata* petite mutant clinical isolate BPY41 was actually more virulent than its non-petite parent BPY40 in murine infection models (Ferrari et al., *Antimicrob. Agents Chemother*. 2011, 55(5):1852-60). The 15-day survival rate of mice infected with BPY41 was 25% compared to 65% when infected with BPY40. Similarly, murine fungal loads of BPY41 after 7-day infection were 10- to 100-fold greater on average. Interestingly, when BPY40 was treated with ethidium bromide to generate a petite mutant, this newly generated petite strain was noticeably less pathogenic than BPY41, with a 15-day survival rate of 85% but similar fungal loads to its parent strain BPY40 (Ferrari et al., *Antimicrob. Agents Chemother*. 2011, 55(5):1852-60). These conflicting observations underscore the need to better understand the role mitochondria play in pathogenic fungi.

Similar work with *Candida albicans* has also proven challenging because *C. albicans* petite mutants are more difficult to obtain (Abuhatab et al., *Biochem. Soc. Trans*. 1992, 20(1):63S; Aoki et al., *J. Med. Vet. Mycol*. 1987, 25(4):269-77). In one case, Cheng, et al. were able to produce a viable petite mutant by passing *C. albicans* SC5314 through murine spleens by intravenous inoculation (Cheng et al., *Cell Microbiol*. 2007, 9(2):492-501; Cheng et al., *Antimicrob. Agents Chemother*. 2007, 51(5):1855-8). After five serial passages, a mutant strain named P5 was isolated and characterized. P5 exhibited several phenotypes characteristic of respiratory mutants, including the inability to proliferate on glucose-deficient media. Subsequent oxygen consumption measurements suggested that while the electron transport chain was intact and functional, it was no longer coupled to ATP synthesis (Cheng et al., *Antimicrob. Agents Chemother*. 2007, 51(5): 1855-8). With regards to clinical relevance, P5 was determined to be 10-fold less susceptible to fluconazole and voriconazole, more resistant to phagocytosis and neutrophils, and less sensitive to superoxide generators. In addition, P5 sustained a completely non-lethal infection in mice for up to 60 days. In contrast, SC5314 infection resulted in 100% mortality within 9 days (Cheng et al., *Cell Microbiol*. 2007, 9(2):492-501).

The reported work with *C. glabrata* and *C. albicans* petite mutants suggests that modifying fungal mtDNA in laboratory settings with chemical agents cannot be relied upon to investigate the clinical behavior of these invasive fungi. Similarly, clinically isolated *Candida* petite mutants may not be amenable to further experimentation. The isolation of petite mutants from patients rarely occurs, and for the few strains harvested thus far, the occurrence of nuclear DNA mutations cannot be ruled out. Identifying specific mitochondrial contributions to *Candida* clinical behavior is thus complicated because the selective pressures of the host environment cannot be reasonably and reliably controlled to allow modification of only fungal mtDNA.

An alternative, untested approach would be to modulate fungal mitochondria function during an active infection. Unfortunately, the current toolbox of mitochondria modulators (FIG. 1) target the oxidative phosphorylation pathway and do not discriminate between fungal or mammalian mitochondria (von Jagow et al., *Methods Enzymol*. 1986, 126:253-71; Ueki et al., *Curr. Opin. Anti-Infective Invest. Drugs* 2000, 2(4):387-398; Sridhara et al., *J. Pharmaceutical. Res*. 2011, 4(2):496-500; Mathre, *Pest Biochem. Physiol*. 1971, 1(2):216-224). Disruption of this process is typically a fatal proposition for both the invading fungi and its mammalian host. A possible fungal-selective mitochondria inhibitor is the antibacterial agent ilicicolin H (FIG. 1, compound 1) (Hayakawa et al., *J. Antibiot*. 1971, 24(9):653-4). Studies by Trumpower et al. have shown that ilicicolin H binds to purified *S. cerevisiae* cytochrome $bc_1$ complex with ~100-fold selectivity over isolated bovine $bc_1$ complex ($IC_{50}$=0.003 µM and 0.200 µM, respectively) (Gutierrez-Cirlos et al., *J. Biol. Chem*. 2004, 279(10):8708-14; Rotsaert et al., *Biochim. Biophys. Acta* 2008, 1777(2):211-9). However, compound 1 displays considerable toxicity against HeLa cells (MIC=2 µg/mL or 4.6 µM) (Hayakawa et al., *J. Antibiot*. 1971, 24(9):653-4). Follow-up studies with ilicicolin H have been slow to emerge, possibly because there are no longer any commercial sources of this natural product.

Here compounds identified are capable of modulating cellular respiration in fungi, preferably by affecting mitochondrial function, without triggering a similar response in mammalian cells. It has been reported that fungal mitochondria possess several proteins lacking human orthologs (Shingu-Vazquez et al., *Eukaryot. Cell* 2011, 10(11):1376-83; Okamoto et al., *Annu. Rev. Genet*. 2005, 39:503-36). In this Example, a phenotypic assay tree is adopted to identify modulators of these unique targets. Such compounds are of great value for interrogating the metabolic requirements of fungal virulence and may be useful as new antifungal drugs that operate in a completely unexploited target space.

Example 2

Preparation of the Compounds

Compounds of Formula (I) (e.g., probe compound I-B-4 (ML316)) may be prepared by the synthetic sequence outlined below in Scheme 1. Cyclohexanone was subjected to a Strecker reaction with 4-fluoroaniline and trimethylsilyl cyanide. The resulting adduct 4 was cyclized to the hydantoin 5 with sodium cyanate, converted to the thiohydanatoin 6, and acylated with ethyl chloroformate to provide compound I-B-4.

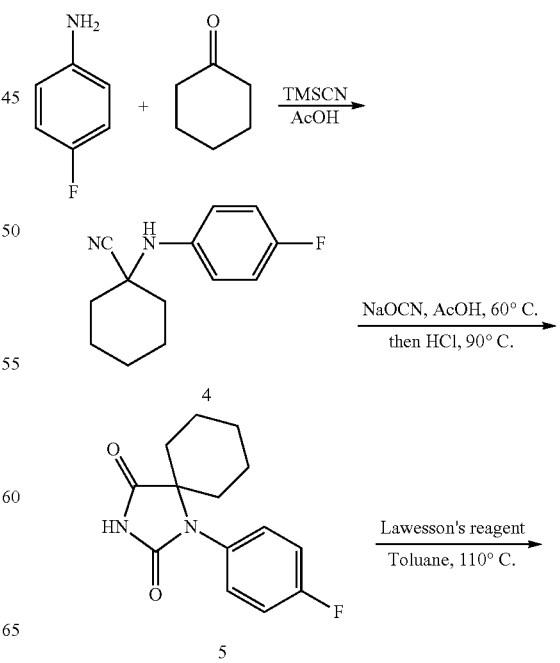

Scheme 1. Exemplary synthesis of compounds of Formula (I) (e.g., compound I-B-4).

87
-continued

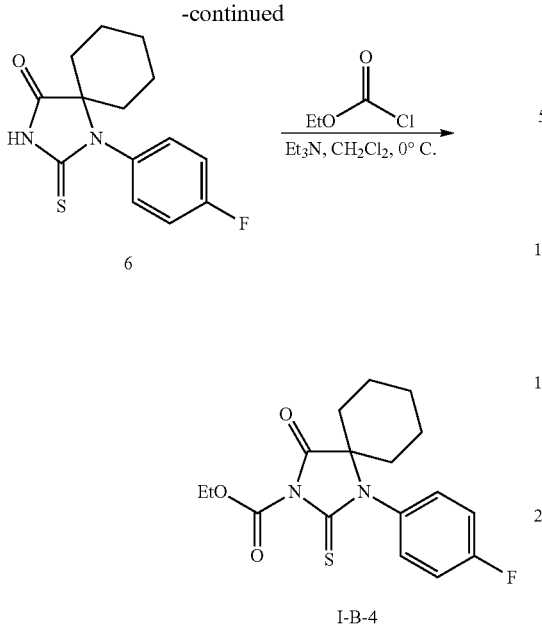

I-B-4

2.1. General Methods

All reagents and solvents were purchased from commercial vendors and used as received. NMR spectra were recorded on a Bruker 300 MHz or Varian UNITY INOVA 500 MHz spectrometer as indicated. Proton, fluorine, and carbon chemical shifts are reported in parts per million (ppm; δ) relative to tetramethylsilane, $CFCl_3$, or $CDCl_3$ solvent ($^1H$ δ 0, $^{19}F$ δ 0, $^{13}C$ δ 77.16, respectively). NMR data are reported as follows: chemical shifts, multiplicity (obs=obscured, app=apparent, br=broad, s=singlet, d=doublet, t=triplet, q=quartet, m=multiplet); coupling constant(s) in Hz; integration. Unless otherwise indicated, NMR data were collected at 25° C. Flash chromatography was performed using 40-60 um Silica Gel (60 Å mesh) on a Teledyne Isco Combiflash Rf system. Tandem liquid chromatography/mass spectrometry (LCMS) was performed on a Waters 2795 separations module and Waters 3100 mass detector. Analytical thin layer chromatography (TLC) was performed on EM Reagent 0.25 mm silica gel 60-F plates. Visualization was accomplished with UV light and aqueous potassium permanganate ($KMnO_4$) stain followed by heating. High-resolution mass spectra were obtained at the MIT Mass Spectrometry Facility with a Bruker Daltonics APEXIV 4.7 Tesla Fourier Transform Ion Cyclotron Resonance mass spectrometer. Compound purity and identity were determined by UPLC-MS (Waters, Milford, Mass.). Purity was measured by UV absorbance at 210 nm. Identity was determined on a SQ mass spectrometer by positive electrospray ionization. Mobile Phase A consisted of either 0.1% ammonium hydroxide or 0.1% trifluoroacetic acid in water, while mobile Phase B consisted of the same additives in acetonitrile. The gradient ran from 5% to 95% mobile Phase B over 0.8 minutes at 0.45 mL/min. An Acquity BEH C18, 1.7 μm, 1.0×50 mm column was used with column temperature maintained at 65° C. Compounds were dissolved in DMSO at a nominal concentration of 1 mg/mL, and 0.25 μL of this solution was injected.

88

2.2. 1-((4-fluorophenyl)amino)cyclohexanecarbonitrile (4)

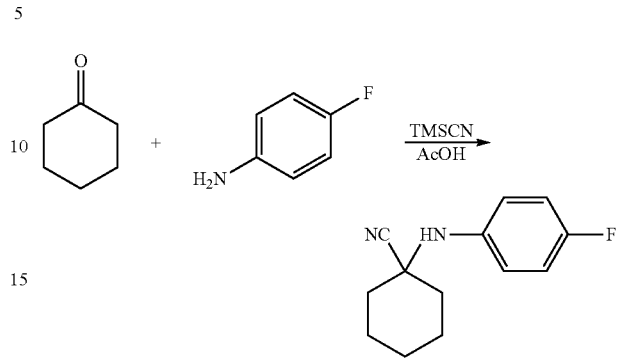

Cyclohexanone (1.0 g, 10.2 mmol) was dissolved in glacial acetic acid (15 mL) and cooled to 10° C. 4-Fluoroaniline (1.4 g, 12.2 mmol, 1.2 equiv.) was added in portions to the reaction, and the resulting mixture was stirred at 10° C. for 15 minutes. Trimethylsilyl cyanide (1.4 mL, 11.2 mmol, 1.1 equiv.) was then added. The reaction was warmed to room temperature and stirred for 15 hours. The reaction was poured into ice-cold ammonium hydroxide solution (30 mL, 20% v/v in water) to give a basic solution (pH>10). This mixture was then extracted with dichloromethane (2×60 mL). The combined organic extracts were washed with brine (80 mL), shaken over magnesium sulfate, filtered, and concentrated under reduced pressure. The crude residue was diluted with hexanes, and the precipitated solids were collected by filtration. After washing with more hexanes, the solids were air-dried and used without further purification (1.7 g, 76%). $^1H$ NMR (300 MHz, $CDCl_3$): δ 7.02-6.88 (m, 4H), 3.46 (br. s, 1H), 2.29-2.19 (m, 2H), 1.85-1.54 (m, 7H), 1.41-1.22 (m, 1H); MS m/z (ESI+): 219 (M+H).

2.3. 1-(4-fluorophenyl)-1,3-diazaspiro[4.5]decane-2,4-dione (5)

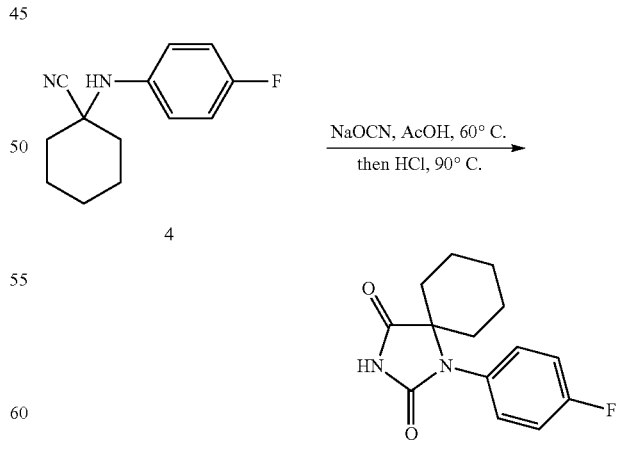

Compound 4 (1.7 g, 7.8 mmol) was suspended in glacial acetic acid (20 mL) and treated with sodium cyanate (0.81 g, 12.5 mmol, 1.6 equiv.). The resulting mixture was heated to 60° C. and stirred at this temperature for 3 hours. A solution of concentrated hydrochloric acid (3 mL) in water (2 mL) was added to the reaction. The resulting mixture was then heated to 90° C. and stirred at this temperature for 30 minutes. The reaction was cooled to room temperature then poured into water (50 mL). The precipitated solids were collected by filtration, washed with water, and air-dried (1.13 g, 55%). $^1$H NMR (300 MHz, CDCl$_3$): δ 8.24 (s, 1H), 7.22-7.10 (m, 4H), 2.15-1.92 (m, 4H), 1.73-1.45 (m, 5H), 1.07-0.90 (m, 1H); MS m/z (ESI+): 263 (M+H).

2.4. 1-(4-fluorophenyl)-2-thioxo-1,3-diazaspiro[4.5]decan-4-one (6)

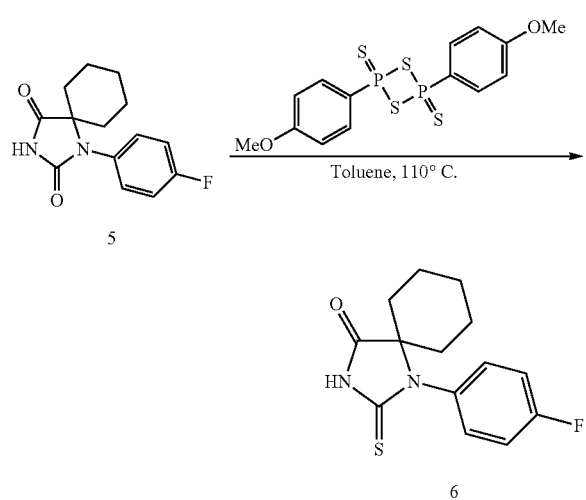 [SMILES: O=C1NC(=O)C2(CCCCC2)N1c1ccc(F)cc1 ; COc1ccc(P2(=S)SP(=S)(c3ccc(OC)cc3)S2)cc1 ; O=C1NC(=S)N(c2ccc(F)cc2)C12CCCCC2]

A solution of compound 5 (0.54 g, 2.1 mmol) in toluene (17 mL) was treated with Lawesson's reagent (0.46 g, 1.1 mmol, 0.55 equiv.). This mixture was heated to reflux and stirred for 5 hours. The reaction was cooled to room temperature and concentrated under reduced pressure. The crude material was purified by column chromatography over silica gel (hexanes/ethyl acetate: 100/0 to 90/10) to give the title compound as a solid (0.50 g, 87%). $^1$H NMR (300 MHz, CDCl$_3$): δ 9.13 (s, 1H), 7.23-7.15 (m, 4H), 2.17-1.96 (m, 4H), 1.75-1.48 (m, 5H), 1.07-0.91 (m, 1H); MS m/z (ESI$^+$): 279 (M+H).

2.5. Ethyl 1-(4-fluorophenyl)-4-oxo-2-thioxo-1,3-diazaspiro[4.5]decane-3-carboxylate (I-B-4)

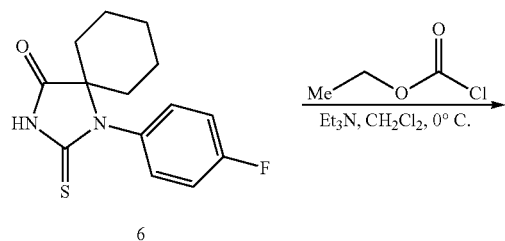

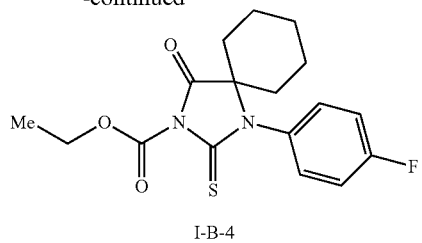

I-B-4

Compound 6 (0.26 g, 0.93 mmol) was dissolved in dichloromethane (9.3 mL) and cooled to 0° C. Triethylamine (0.18 mL, 1.9 mmol, 2.0 equiv.) was added, followed by ethyl chloroformate (0.26 mL, 1.9 mmol, 2.0 equiv.). The reaction was stirred at 0° C. for 2 hours before quenching with water (10 mL). The layers were separated and the aqueous phase was extracted with dichloromethane (3×10 mL). The combined organic layers were dried over magnesium sulfate, filtered, and concentrated under reduced pressure. The crude material was purified by column chromatography over silica gel (hexanes/ethyl acetate: 100/0 to 80/20) to give the title compound as a white solid (87.1 mg, 27%). $^1$H NMR (500 MHz, CDCl$_3$): δ 7.25-7.17 (m, 4H), 4.53 (q, J=7.1 Hz, 2H), 2.13-2.02 (m, 4H), 1.77-1.65 (m, 3H), 1.57 (td, J=13.5, 4.2 Hz, 2H), 1.47 (t, J=7.1 Hz, 3H), 1.06-0.95 (m, 1H); $^{19}$F NMR (282 MHz, CDCl$_3$): δ−110.88 (tt, J=7.6, 5.3 Hz); $^{13}$C NMR (125 MHz, CDCl$_3$): δ 177.3, 171.7, 162.9 (d, $J_{C\text{-}F}$=250.6 Hz), 148.5, 132.4 (d, $J_{C\text{-}CF}$=8.9 Hz), 130.4, 116.9 (d, $J_{C\text{-}CF}$=22.9 Hz), 67.3, 65.8, 32.4, 23.9, 20.6, 13.9; HRMS m/z (ESI$^+$): calculated for C$_{17}$H$_{19}$FN$_2$O$_3$SNa [M+Na]373.0993. found 373.1100.

Example 3

Analytical Assays of the Compounds

Compounds of Formula (I) (e.g., compound I-B-4 (ML316)) were analyzed by UPLC, $^1$H, $^{19}$F, and $^{13}$C NMR spectroscopy, and high-resolution mass spectrometry. The data obtained from NMR and mass spectroscopy are consistent with the structure of the compounds, and UPLC (Ultra Performance Liquid Chromatography) indicates an isolated purity of greater than 95%.

3.1. Solubility

Solubility was determined in phosphate buffered saline (PBS) pH 7.4 with 1% DMSO. Each compound was prepared in duplicate at 100 µM in both 100% DMSO and PBS with 1% DMSO. Compounds were allowed to equilibrate at room temperature with a 250 rpm orbital shake for 24 hours. After equilibration, samples were analyzed by UPLC-MS (Waters, Milford, Mass.) with compounds detected by SIR detection on a single quadrupole mass spectrometer. The DMSO samples were used to create a two-point calibration curve to which the response in PBS was fit.

3.2. PBS Stability

Stability was determined in the presence of PBS pH 7.4 with 0.1% DMSO. Each compound was prepared in duplicate on six separate plates and allowed to equilibrate at room temperature with a 250-rpm orbital shake for 48 hours. One plate was removed at each time point (0, 2, 4, 8, 24, and 48 hours). An aliquot was removed from each well and analyzed by UPLC-MS (Waters, Milford, Mass.) with compounds detected by SIR detection on a single quadrupole mass spectrometer. Additionally, to the remaining material at each time point, acetonitrile was added to force dissolution of compound (to test for recovery of compound). An aliquot of this was also analyzed by UPLC-MS.

3.3. GSH Stability

Figure 2:
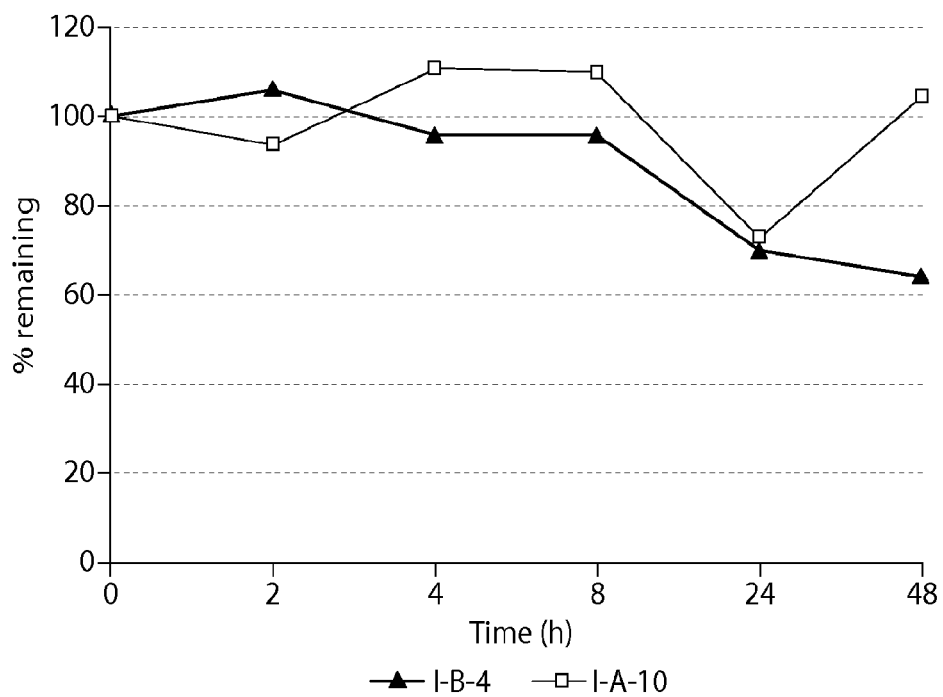
FIG. 2 shows the stability of the probe compound I-B-4 (ML316) and compound I-A-10 (CID56604835) in PBS Buffer (pH 7.4, 23° C.).
Figure 3A:
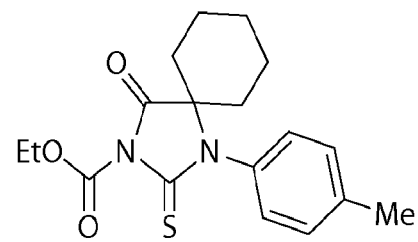
FIGS. 3A-B show the dose response curves for initial hit compound I-A-1 (CID3889161). Compound I-A-1 was used over a range of concentrations up to 26 μM in the primary assay and secondary assays. Dose curves were generated with Genedata Condeseo and show normalized percent activity for the individual doses. C. albicans CaCi-2 growth inhibition (AID 623899), IC$_{50}$=0.3 µM (FIG. 3A); Murine 3T3 fibroblasts growth inhibition (AID 602394), IC$_{50}$>26 µM (FIG. 3B).
Figure 3A:
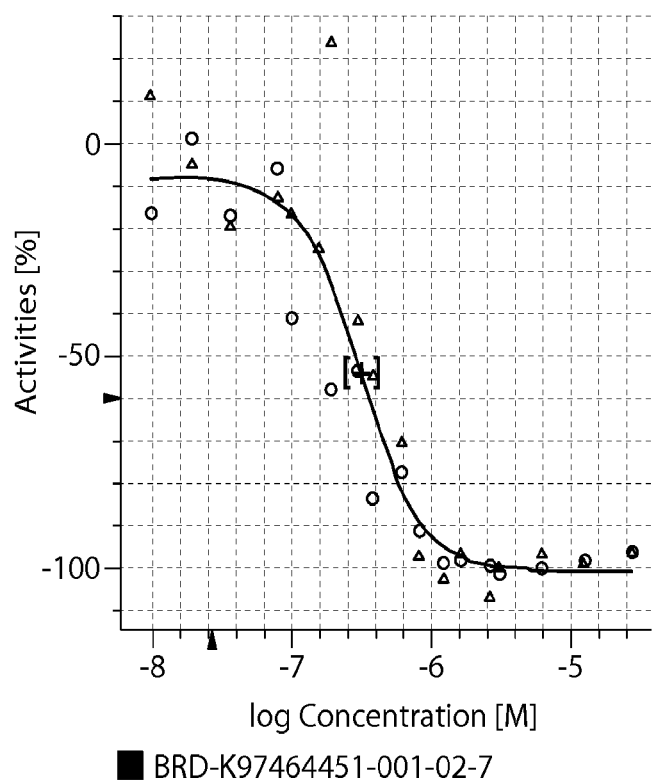
Figure 3B:
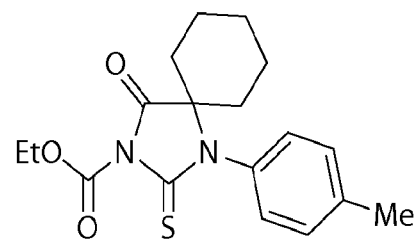
Figure 3B:
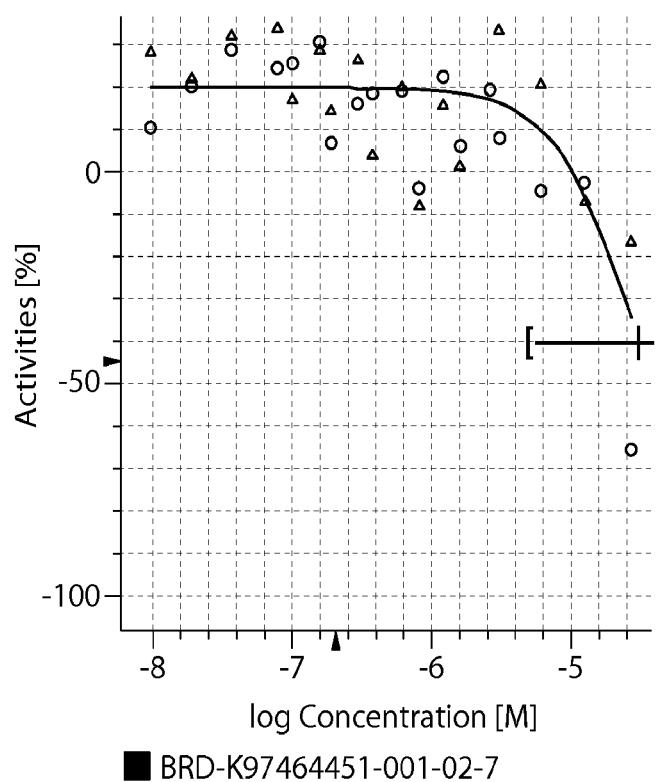

Stability was determined in the presence of PBS pH 7.4 µM and 50 M glutathione with 0.1% DMSO. Each compound was prepared in duplicate on six separate plates and allowed to equilibrate at room temperature with a 250-rpm orbital shake for 48 hours. One plate was removed at each time point (0, 2, 4, 8, 24, and 48 hours). An aliquot was vided in FIG. 2. The probe compound I-B-4 is unstable in human and murine plasma with less than 1% remaining after incubation at 37° C. for 5 hours. The ethyl carbamate appears to be the primary source of instability since replacing the carbamate with a methyl group (compound I-A-10, CID56604835) significantly increases plasma stability (Table 1). Unfortunately, the stable analog compound I-A-10 (CID56604835) shows no activity against the *C. albicans* test strains (see Section 3.4 for full details).

TABLE 1

Plasma Stability of Compound I-B-4 and Compounds I-A-1 and I-A-10.

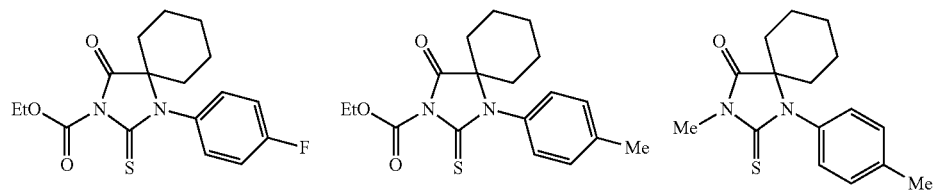

| Compound # | I-B-4 | I-A-1 | I-A-10 |
|---|---|---|---|
| PubChem CID | 56604860 | 3889161 | 56604835 |
| ML# | ML316 | Not applicable | Not applicable |

| | | | | |
|---|---|---|---|---|
| Plasma stability (% remaining after 5 hours) | Human | <1.0% | <1.0% | 95.7% |
| | Murine | <1.0% | <1.0% | 96.6% |
| Plasma protein binding (% bound) | Human | N/A | N/A | 98.6% |
| | Murine | N/A | N/A | 99.9% | removed from each well and analyzed by UPLC-MS (Waters, Milford, Mass.) with compounds detected by SIR detection on a single quadrupole mass spectrometer. Additionally, to the remaining material at each time point, acetonitrile was added to force dissolution of compound (to test for recovery of compound). An aliquot of this was also analyzed by UPLC-MS.

3.4. Plasma Protein Binding

Plasma protein binding was determined by equilibrium dialysis using the Rapid Equilibrium Dialysis (RED) device (Pierce Biotechnology, Rockford, Ill.) for both human and mouse plasma. Each compound was prepared in duplicate at 5 µM in plasma (0.95% acetonitrile, 0.05% DMSO) and added to one side of the membrane (200 µL) with PBS pH 7.4 added to the other side (350 µL). Compounds were incubated at 37° C. for 5 hours with a 250-rpm orbital shake. After incubation, samples were analyzed by UPLC-MS (Waters, Milford, Mass.) with compounds detected by SIR detection on a single quadrupole mass spectrometer.

3.5. Plasma Stability

Plasma stability was determined at 37° C. at 5 hours in both human and mouse plasma. Each compound was prepared in duplicate at 5 µM in plasma diluted 50/50 (v/v) with PBS pH 7.4 (0.95% acetonitrile, 0.05% DMSO). Compounds were incubated at 37° C. for 5 hours with a 250-rpm orbital shake with time points taken at 0 hours and 5 hours. Samples were analyzed by UPLC-MS (Waters, Milford, Mass.) with compounds detected by SIR detection on a single quadrupole mass spectrometer.

3.6. Results

The solubility of the probe compound I-B-4 (ML316) was experimentally determined to be 1.1 µM in phosphate buffered saline with 1% (v/v) DMSO. The probe is reasonably stable in PBS solution (>60% remaining after a 48-hour incubation). The data from the PBS stability assay is pro- The physical properties of compound I-B-4 (ML316) are summarized below in Table 2.

TABLE 2

Computed Properties of the Probe Compound I-B-4 (ML316)

| | |
|---|---|
| IUPAC chemical name | ethyl 1-(4-fluorophenyl)-4-oxo-2-thioxo-1,3-diazaspiro[4.5]decane-3-carboxylate |
| PubChem CID | 56604860 |
| Molecular Formula | $C_{17}H_{19}FN_2O_3S$ |
| Molecular Weight (g/mol) | 350.41 |
| Exact Mass (amu) | 350.1100 |
| ClogP* | 4.57 |
| Topological Polar Surface Area* | 49.85 |
| H-Bond Donors | 0 |
| H-Bond Acceptors | 3 |
| Rotatable Bond Count | 4 |

*Calculated with ChemBioDraw Ultra, version 12.0.

Example 4

Biological Assays of the Compounds 4.1. Materials and Methods

Materials and Reagents.

Ilicicolin H was previously purchased from Analyticon Discovery (Catalog No. NP-005728) and was purified by column chromatography prior to use.

Alamar Blue was purchased from Invitrogen (Catalog No. DAL1100).

Amphotericin B was purchased from Sigma-Aldrich (Catalog No. A2411).

Geldanamycin was obtained from AG Scientific (Catalog No. G-1047).

JC-1 dye was obtained from Invitrogen (Catalog No. T-3168).

Antimycin A was obtained from Sigma (Catalog No. A8674).

Cell Lines.

*Candida albicans* CaCi-2; a drug-resistant clinical isolate was provided by the Whitehead Institute (Redding et al., *Clin. Infect. Dis.* 1994, 18(2):240-2). This strain was used for the primary assay.

*Candida albicans* CaCi-17; a strongly drug-resistant clinical isolate was provided by the Whitehead Institute (Redding et al., *Clin. Infect. Dis.* 1994, 18(2):240-2). This strain was used for the primary assay

*Saccharyomyces cerevisiae* W303-1a (ATCC 208352); a well-characterized *Saccharomyces* strain used for determination of glycolytic vs. respiratory metabolism, as well as in the mitochondrial disruption assay.

*Candida glabrata* (ATCC 2001); used for determination of glycolytic vs. respiratory metabolism.

NIH-3T3 mammalian fibroblasts (ATCC; CRL no.1658); used for mammalian toxicity assays.

A summary listing completed assays and corresponding PubChem AID numbers is provided in Table 11.

output is read. Compounds possessing an $IC_{50}$ value less than 10 μM were selected for further studies.

Materials and Reagents

Clear, flat bottom, black, 384-well plates (Corning, Catalog No. 3712BC Lot No. 35808016); Amphotericin (Sigma, Catalog No. A2411) 15 mM stock solution in DMSO; Pen/Strep (Gibco, Catalog No. 10378-016; Lot No. 21040170) 100× in PBS; Alamar Blue (AG Scientific, Catalog no.DAL 1100; Lot No. 151016SA); PBS without Calcium and Magnesium (Cellgro, Catalog No. 21-040-CV).

Synthetic defined growth medium. RPMI 1640 medium, (powder without sodium bicarbonate; Invitrogen, Catalog No. 31800-089; Lot No. 648072); Uridine 8 mg/mL in water (Sigma, Catalog No. U3750, Lot No. 028KO760); Glucose 40% (w/v) in water (Sigma, Catalog No. G-5400); MOPS Buffer (Sigma, Catalog No. M-1254; Lot No. 098K0033).

Prepare 1×RPMI medium by dissolving 10.4 grams powdered medium in 800 mL water.

Add 34.52 g MOPS. While stirring, adjust pH to 7.0 with 10 N NaOH.

Add 10 mL uridine solution and 50 mL glucose solution; adjust final volume to 1000 mL. Filter sterilize.

TABLE 11

Summary of Completed Assays and AIDs

| PubChem AID | Type | Target | Concentration Range (μM) | Samples Tested |
|---|---|---|---|---|
| 558529 | Primary | CaCi-2 growth inhibition | 26-0.01 | 39 |
| 588530 | Primary | CaCi-17 growth inhibition | 26-0.01 | 39 |
| 602190 | Confirmatory (Powder) | CaCi-2 growth inhibition | 26-0.1 | 24 |
| 602189 | Confirmatory (Powder) | CaCi-17 growth inhibition | 26-0.1 | 24 |
| 623899 | Analogs | CaCi-2 growth inhibition | 26-0.01 | 55 |
| 623897 | Analogs | CaCi-17 growth inhibition | 26-0.01 | 55 |
| 623981, 624006 | Analogs (low dose) | CaCi-2 growth inhibition | 3-0.000006 | 7 |
| 623982 | Analogs (low dose) | CaCi-17 growth inhibition | 3-0.000006 | 7 |
| 588634 | Secondary | Fibroblast Toxicity | 26-0.01 | 39 |
| 602394 | Secondary (Analogs) | Fibroblast Toxicity | 26-0.01 | 55 |
| 623967, 624013 | Secondary (Analogs) | *C glabrata* on glucose | 3-0.000006 | 7 |
| 623965, 624014 | Secondary (Analogs) | *C glabrata* on glycerol | 3-0.000006 | 7 |
| 623971, 624025 | Secondary (Analogs) | *S cerevisiae* on glucose | 3-0.000006 | 7 |
| 623969, 624012 | Secondary (Analogs) | *S cerevisiae* on glycerol | 3-0.000006 | 7 |
| 624062 | Secondary (Analogs) | *C. glabrata* mitochondria inhibition | 1.0 | 7 |
| 624068 | Secondary (Analogs) | *S. cerevisiae* mitochondria inhibition | 1.0 | 7 |

4.2. Primary CaCi-2 (AID No. 588529) and CaCi-17 (588530), CaCi-2 Dose-Response Retest (AID Nos. 602190, 623899, 623981, 624006) and CaCi-17 Dose-Response Retest (AID Nos. 602189, 623897, 623982)

The primary assay measures reduction of viability (as measured by reduced fluorescence in the presence of Alamar Blue) by potential inhibitors. The assay was performed using two *Candida albicans* clinical isolates to determine the range of the antifungal activity. In this assay, a fungal inoculum is dispensed into 384-well assay plates in which 100 nL of compounds have been pinned. After 48 hours of incubation at 30° C., Alamar Blue is added and fluorescence Fungal inoculum. Test Strains: *C. albicans* CaCi-2 and *C. albicans* CaCi-17.

Inoculate 500 μL of strain from cryopreserved stock into 250 mL shaker flask containing 30 mL growth medium. Shake at 30° C. overnight.

Read OD 600 of 1 mL fungal culture in a cuvette using a standard optical density reader (Eppendorf BioPhotometer Plus), with growth medium as a background blank.

Dilute to desired volume of fungal inoculums according to the following formula: (1/*OD* measured)×(Desired Final Volume of Inoculum)×0.3=Volume of fungal culture (μL) to add to desired volume of growth medium.

When added to media in wells, this yields a calculated starting OD of the fungal inoculum of 0.00015.

Procedures

Add Pen/Strep at 0.1 mL per 10 ml media (1% v/v).

Use a Thermo Combi nL to dispense 20 µL/well of assay media into all wells.

Pin 100 nL test compound from compound plates into assay plates using CyBi-Well pin tool.

Dispense 20 µL/well of culture into the assay media in all wells.

Incubate plates in a humidified (90% humidity) Liconic incubator at 37° C. without agitation for 48 hours.

Dilute Alamar Blue Reagent 1:40 in Ca/Mg-free PBS.

To all plates, add 5 µL/well of the diluted Alamar to a final dilution factor of 1:200.

Incubate the plates for an additional 2 hours.

Read the Relative Fluorescence Intensity (RFU) of wells on a standard plate reader as a measure of relative fungal growth. Envision (Perkin Elmer) plate reader set-up: Ex 544 nm, Em 590 nm, Bandwidth 12 nm, Top read.

4.3. Counterscreen Mammalian Cell Toxicity Assay (AID Nos. 588634, 602394)

Quiescent murine fibroblasts were subjected to incubation with compounds of interest for 48 hours. Subsequent cell viability was determined via measuring Alamar Blue fluorescence. Toxicity at less than 10 times the effective CaCi-2 $IC_{50}$ or less than 20 µM was an indication of a poor therapeutic index and resulted in exclusion of the associated compound from further consideration.

Materials and Reagents

Clear, flat bottom, black 384-well plates (Corning, Catalog No. 3712BC; Lot No. 35808016); Geldanamycin (AG Scientific, Catalog No. G-1047) 15 mM stock solution in DMSO; Alamar Blue (AG Scientific, Catalog No. DAL1100, Lot No. 151016SA); PBS without Calcium and Magnesium (Cellgro, Catalog No. 21-040-CV).

Assay medium. Optimem medium (Invitrogen, Catalog No. 31985-070; Lot No. 548536); 2.5% (v/v) Fetal Bovine Serum (Hyclone, Catalog No. 30071.03; Lot No. ARF26748); 1% (v/v) Pen/Strep solution (Invitrogen, Catalog No. 15140-122; Lot No. 529891).

Cell inoculum. Test Strain: NIH-3T3 mammalian fibroblasts (ATCC CRL No. 1658).

Plate cells in 384-well plates at 1,000 cells/well in 40 µL assay medium.

Incubate plates overnight at 37° C. under 5% $CO_2$.

Procedures

After overnight culture, pin compounds into wells at 100 nL/well using the CyBio CyBi-Well pinning instrument.

Return the plates to the tissue culture incubator and incubate the culture for an additional 48 hours at 37° C. under 5% $CO_2$.

At the completion of this incubation, add Alamar Blue solution diluted 1:40 in PBS to each well (10 µL/well) to achieve a final dilution of 1:200.

Incubate the plates for an additional 2-3 hours at 37° C. under 5% $CO_2$.

Read the Relative Fluorescence Intensity (RFU) of wells on a standard plate reader as a measure of relative cell growth. Envision (Perkin Elmer) plate reader set-up: Ex 544 nm, Em 590 m, Bandwidth12 nm, Top read.

4.4. Secondary *S. cerevisiae* Inhibition in Glucose Media (AID Nos. 623971, 624025), *S. cerevisiae* Inhibition in Glycerol Media (AID Nos. 623969, 624012), *C. glabrata* Inhibition in Glucose Media (AID Nos. 623967, 624013), and *C. glabrata* Inhibition in Glycerol Media (AID Nos. 623965, 624014)

*Saccharomyces*, while not a major human pathogen, is a useful lab model with well-developed genetic tools available. *Candida glabrata* is an increasingly prominent clinical problem for immune-compromised patients but with fewer genetic tools available with which to study it. These organisms can utilize alternative metabolic pathways to support growth and survival depending on the carbon source. By comparing the concentration-dependent inhibition of yeast growth in glycerol relative to glucose media, a quantitative assessment of a compound's ability to disrupt respiration can be determined. It is preferred that compounds in this assay have an $IC_{50}$ of less than 10 µM in both organisms when grown in glycerol media. It is also preferred that there is at least a 10-fold loss in potency against both organisms when they are grown in glucose media, thus indicating respiratory disruption.

Secondary Glycerol Assay Protocol (AID 623969, 623965, 624014, 624012)

Materials and Reagents

Clear, flat bottom, black 384-well plates (Corning Catalog no. 3712BC; Lot no. 35808016); Amphotericin B (Sigma Catalog no. A2411) 15 mM stock solution in DMSO; Pen/Strep (Gibco Catalog no. 10378-016; Lot no21040170) 100× in PBS.

Synthetic defined growth medium. Complete Supplement Mixture; (Sunrise Science, Catalog No. 1001-100); Yeast Nitrogen Base without ammonium sulfate (MP Biomedicals, Catalog No. 4027-012); Glycerol (Sigma Catalog No. G-9012).

Prepare medium by dissolving 0.79 g Complete Supplement Mixture and 1.7 g Yeast Nitrogen Base in 800 mL water.

Add 20 mL of glycerol. Adjust final volume to 1000 mL. Filter sterilize.

Fungal Inoculum. Test Strains: *C. glabrata* (ATCC 2001) and *Saccharomyces cerevisiae* W303.

Inoculate 100 µL of yeast from cryopreserved stock into 250 mL shaker flask containing 20 mL growth medium. Shake at 30° C. overnight (about 16 hours).

Read OD 600 of 1 mL of fungal culture in a cuvette using a standard optical density reader (Eppendorf BioPhotometer Plus), with growth medium as a background blank.

Dilute to desired volume of fungal inoculum to produce an OD600 reading of 0.005 (*S. cerevisiae*) or 0.004 (*C. glabrata*).

Procedures

Use a Thermo Combi nL to dispense 20 µL/well of assay media into all wells.

Add 2 µL of Amphotericin B to control wells.

Pin 100 nL of test compound from compound plates into assay plates using a CyBi-Well pin tool.

Dispense 20 µL/well of culture into the assay media in all wells.

Incubate the plates in a humidified (90% humidity) Liconic incubator at 37° C. without agitation for 48 hours.

Shake plates briefly.

Read OD600 of wells on a standard plate reader as measure of relative fungal growth. Envision (Perkin Elmer) plate reader settings: Ex Photometric 600, Top read.

Secondary Glucose Assay Protocol (AID 623971, 623967, 624013, 624025)

Materials and Reagents

Clear, flat bottom, black 384-well plates (Corning, Catalog No. 3712BC; Lot No. 35808016); Amphotericin B (Sigma, Catalog no. A2411) 15 mM stock solution in DMSO; Pen/Strep (Gibco, Catalog No. 10378-016; Lot no21040170) 100× in PBS.

Synthetic defined growth medium. Complete Supplement Mixture; (Sunrise Science, Catalog No. 1001-100); Yeast Nitrogen Base without ammonium sulfate (MP Biomedicals, Catalog No. 4027-012); Glucose (Sigma, Catalog No. G7021).

Prepare medium by dissolving 0.79 g of Complete Supplement Mixture and 1.7 g of Yeast Nitrogen Base in 800 mL of water.

Add 20 g of glucose. Adjust final volume to 1000 mL. Filter sterilize.

Fungal Inoculum. Test Strains: *C. glabrata* (ATCC 2001) and *Saccharomyces cerevisiae* W303.

Inoculate 100 L of yeast from cryopreserved stock into a 250 mL shaker flask containing 20 mL of growth medium. Shake at 30° C. overnight (about 16 hours).

Read OD 600 of 1 mL of fungal culture in a cuvette using a standard optical density reader (Eppendorf BioPhotometer Plus), with growth medium as a background blank.

Dilute to desired volume of fungal inoculum to produce an OD600 reading of 0.005 (*S. cerevisiae*) or 0.004 (*C. glabrata*).

Procedures

Use a Thermo Combi nL to dispense 20 μL/well of assay media into all wells.

Add 2 μL of Amphotericin B to control wells.

Pin 100 nL of test compound from compound plates into assay plates using a CyBi-Well pin tool.

Dispense 20 μL/well of culture into the assay media in all wells.

Incubate the plates in a humidified (90% humidity) Liconic incubator at 37° C. without agitation for 48 hours.

Shake plates briefly.

Read OD600 of wells on a standard plate reader as measure of relative fungal growth. Envision (Perkin Elmer) plate reader settings: Ex Photometric 600, Top read.

4.5. Secondary Mitochondrial Disruption Assay (AID No. 624062 and 624068)

The fluorescent dye JC-1 was used to quantify the ability of compounds to disrupt the mitochondrial membrane potential of fungi. Mitochondrial membrane depolarization is indicated by a decrease in the yellow/green fluorescence intensity ratio. This is a non-gating, binning assay that establishes whether inhibition of fungal growth in glycerol results from direct compromise of mitochondrial function or alternative components of fungal respiratory metabolism. Probes that disrupt mitochondrial function as well as those that perturb other metabolic components are desirable.

Materials and Reagents

JC-1 Dye (Invitrogen, Catalog No. T-3168); Antimycin A (Sigma, Catalog No. A8674).

Synthetic defined growth medium. Complete Supplement Mixture; (Sunrise Science, Catalog No. 1001-010); Yeast Nitrogen Base without ammonium sulfate (BD, Catalog No. 239210); Glucose (Sigma, Catalog No. G7021).

Prepare medium by dissolving 0.79 g of Complete Supplement Mixture and 6.7 g of Yeast Nitrogen Base in 800 mL water.

Add 20 g of glucose. Adjust final volume to 1000 ml. Filter sterilize.

Test Strains. *Saccharomyces cerevisiae* strain W303-1a (ATCC#208352) and *Candida glabrata* (ATCC#2001).

Procedures

Grow a 2 mL of overnight culture of W303 strain at 30° C.

Dilute to an OD600 of 0.1 in 2 mL of fresh media (one tube per compound replicate).

Incubate at 30 OC with agitation for 90 minutes.

Add compounds at desired concentrations.

Incubate 4 hr at 30° C. with agitation.

Aliquot 1 mL of culture into a microcentrifuge tube.

Add JC-1 dye stock to tube at a final concentration of 1 μg/mL.

Incubate 30 minutes in the dark with agitation at 30° C.

Wash out dye by centrifuging and resuspending in SD-CSM media twice.

Analyze by flow cytometry using a 488 nM excitation laser and detect emission on FL1 and FL2 channels. Polarized mitochondria will emit strongly at about 590 nm in the FL2 channel; while depolarized mitochondria will emit mainly at about 525 nm in the FL1 channel. The ratio of FL2 to FL1 fluorescence thus reports on polarization, which must be initially calibrated with a negative DMSO control.

4.6. Data Analysis

For the primary screen and other assays, negative-control (NC) wells and positive-control (PC) wells were included on every plate. The raw signals of the plate wells were normalized using the "Stimulators Minus Neutral Controls" method in Genedata Assay Analyzer (v7.0.3). The median raw signal of the intra-plate NC wells was set to a normalized activity value of 0, while the median raw signal of the intra-plate PC wells was set to a normalized activity value of 100. Experimental wells were scaled to this range, resulting in an activity score representing the percent change in signal relative to the intra-plate controls. The mean of the replicate percent activities were presented as the final "Pubchem Activity Score." The "Pubchem Activity Outcome" class was assigned as described below, based on an activity threshold of 70%:

Activity_Outcome=1 (inactive), less than half of the replicates fell outside the threshold.

Activity_Outcome=2 (active), all of the replicates fell outside the threshold, OR at least half of the replicates fell outside the threshold AND the "Pubchem Activity Score" fell outside the threshold.

Activity_Outcome=3 (inconclusive), at least half of the replicates fell outside the threshold AND the "Pubchem Activity Score" did not fall outside the threshold.

4.7. Results

Probe Attributes

Inhibits growth in primary screen cell line *C. albicans* CaCi-2 at an $IC_{50} \leq 10$ μM.

Inhibits growth in resistant cell line *C. albicans* CaCi-17 at an $IC_{50} \leq 10$ μM.

Inhibits growth in *S. cerevisiae* grown on glycerol at an $IC_{50} \leq 10$ μM.

Inhibits growth in *C. glabrata* grown on glycerol at an $IC_{50} \leq 10$ μM.

Shows at least 10-fold selectivity between the CaCi-2 test strain and murine 3T3 cells.

Shows at least 10-fold selectivity between *S. cerevisiae* grown on glycerol and *S. cerevisiae* grown on glucose.

Show at least 10-fold selectivity between *C. glabrata* grown on glycerol and *C. glabrata* grown on glucose.

An earlier MLPCN effort has identified compounds capable of reversing antifungal drug-resistance, thereby providing probes to interrogate the mechanisms responsible for drug-resistance in medically relevant fungi (PubChem summary AID 2007). Here, a primary assay is used to identify compounds that directly inhibit fungal growth, and a secondary assay is used to measure a compound's intrinsic antifungal activity (AID 2387), rather than its ability to reverse resistance to the widely used antimycotic fluconazole. This secondary assay identified a number of compounds that possessed potent single agent activity against a range of opportunistic human fungal pathogens, preferably under culture conditions that require mitochondrial respiratory metabolism for growth and survival.

Data reported in PubChem for growth inhibition of *Candida albicans* as well as mammalian fibroblasts (AID 2387 and 2327, respectively) have been analyzed. Analysis of this data identified 43 compounds that inhibited *C. albicans* growth with $IC_{50} \leq 10$ µM. Approximately 75% (30 of 43) of these single-agent antimycotics showed modest selectivity against fibroblasts ($IC_{50} \geq 20$ µM). Based on this data mining, seventeen dry powders were obtained and evaluated for *C. albicans* and fibroblast growth inhibition. After examining the re-test data, a spirocyclic thiohydantoin derivative I-A-1 (CID3889161) was identified for further development.

The initial hit compound I-A-1 (CID3889161, FIG. 3) is a potent inhibitor of *C. albicans* growth ($IC_{50}$=0.3 µM), with insignificant activity against murine fibroblasts ($IC_{50}$>26 µM). Analogs of I-A-1 (CID3889161) were designed and prepared accordingly, resulting in the identification of the more potent probe compound I-B-4 (ML316). The biological properties of compound I-B-4 (ML316) are summarized in Tables 12-13.

TABLE 12

Biological Properties of Compound I-B-4 (ML316)

| CID/ML No. | Targets | $IC_{50}$ (µM) [SID, AID] | Anti-Target | $IC_{50}$ (µM) [SID, AID] | Fold Selective* |
|---|---|---|---|---|---|
| 56604860 ML316 | CaCi-2 growth inhibition | 0.04 [134356650, 623899] | Fibroblast toxicity | >26 [134356650, 602394] | >650x |
| | CaCi-17 growth inhibition | 1.0 [134356650, 623897] | | | >37x |

*Selectivity = Anti-target $IC_{50}$/Target $IC_{50}$

TABLE 13

Biological Properties of Compound I-B-4 (ML316)

| CID/ML No. | Secondary Assays | $IC_{50}$ (µM) [SID, AID] | Fold Selective[†] |
|---|---|---|---|
| 56604860 ML316 | Inhibition of *S. cerevisiae* growth on glycerol | 0.004 [134356650, 623969] | >750x |
| | Inhibition of *S. cerevisiae* growth on glucose | >3.0 [134356650, 623971] | |
| | Inhibition of *C. glabrata* growth on glycerol | 0.011 [134356650, 623965] | >272x |
| | Inhibition of *C. glabrata* growth on glucose | >3.0 [134356650, 623967] | |

[†]Selectivity = Glucose $IC_{50}$/Glycerol $IC_{50}$.

Summary of Screening Results

An earlier high-throughput screen evaluated 302,509 compounds for their ability to chemosensitize the fluconazole-resistant *Candida albicans* strain CaCi-2 to a sublethal concentration of fluconazole (PubChem AID 1979). A secondary screen of the primary assay hits was included to identify any intrinsic antimycotic activity, and 342 compounds were evaluated in this assay. 43 compounds displayed inhibitory activity against CaCi-2 with $IC_{50}$ values below 10 µM (AID 2387). While their antifungal activity disqualified these compounds from the prior project, this set of 43 compounds was re-purposed for the current campaign to identify potent single-agent antimycotics.

DMSO stocks of only 39 compounds were available for re-test against the *C. albicans* strain CaCi-2 (PubChem AID 588529) and the more highly drug-resistant CaCi-17 (PubChem AID 588530). Of the 39 compounds, 23 surpassed the less than 10 µM $IC_{50}$ screening cutoff for both assays. Unfortunately, the cytotoxicity of many compounds appeared to be non-specific as determined by a murine 3T3 fibroblast counterscreen (AID 588634). Of the 23 antifungal compounds, only two compounds (CID26662188 and CID3889161) displayed greater than 10-fold selectivity towards fungal cells. One compound (CID26662188) was deemed chemically intractable and subsequently discarded.

In order to identify additional candidates, the PubChem data for AID 2387 was revisited. The CaCi-2 inhibitory activity threshold was raised from 10 µM to 15 µM to produce a list of 67 compounds. This hit list was cross-referenced against the 39 compounds previously evaluated as described above and also checked for fibroblast toxicity using available PubChem data (AID 2327). After applying these filters, an additional 17 compounds were obtained.

Figure 4:
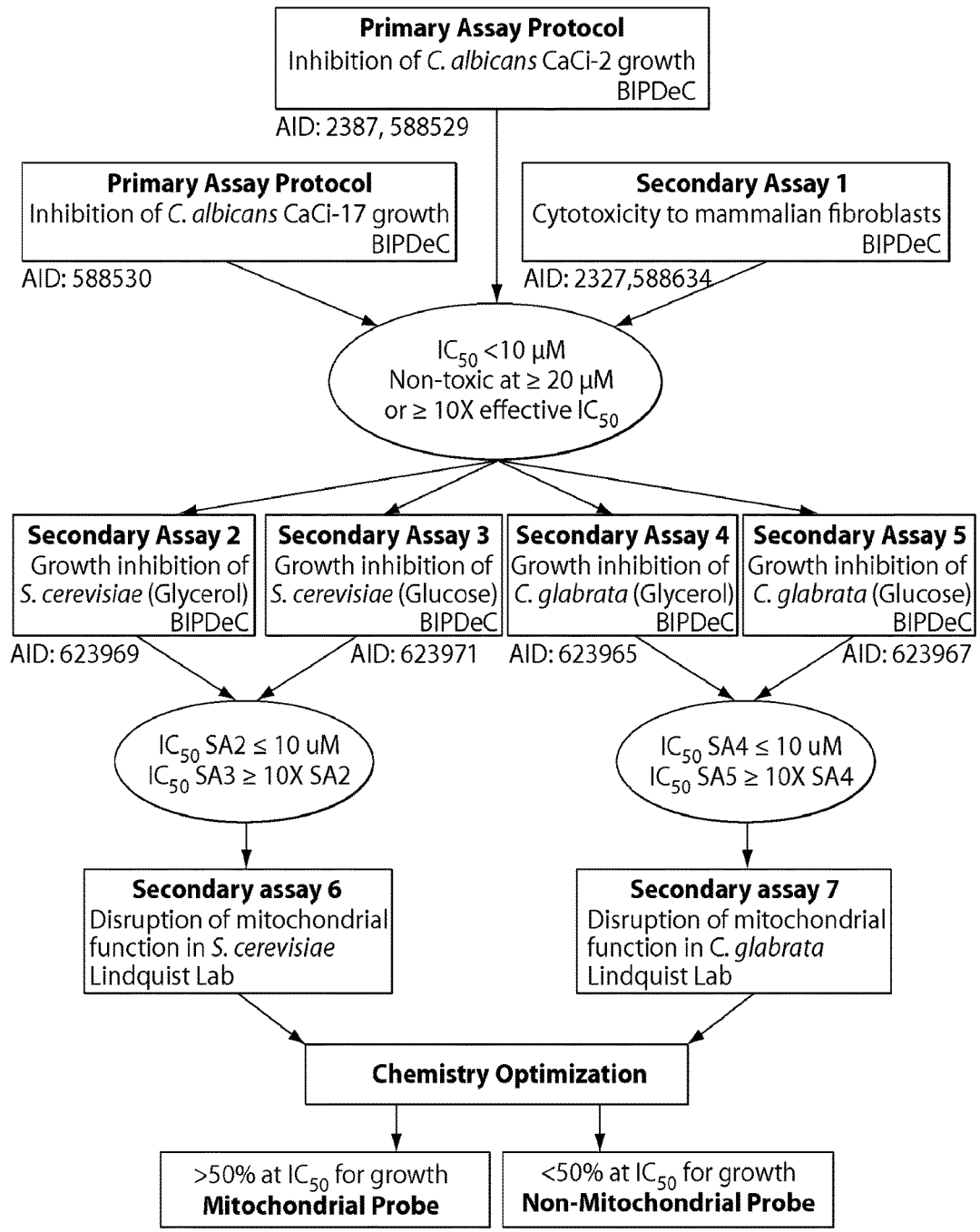
FIG. 4 shows the critical path for the probe development.

Dry powders for these 17 compounds, as well as for CID3889161, were procured for re-testing. In addition, several analogs of promising compounds were obtained to provide preliminary SAR data and validate these scaffolds. After purity analysis and structural confirmation by NMR spectroscopy, a total 24 substances was screened according to the workflow outlined below in FIG. 4. The screens in this pathway consist of CaCi-2 and CaCi-17 inhibitory activity, mammalian toxicity, and growth media-dependent activity against *C. glabrata* and *S. cerevisiae*. The associated PubChem AIDs for these assays are provided in FIG. 4. CID3889161 emerged as the most promising candidate and was subsequently prioritized for further investigation. A number of analogs related to this scaffold were prepared and assayed for fungal selective respiratory inhibition.

Dose Response Curves for Probe Compound I-B-4 (ML316)

Figure 5A:
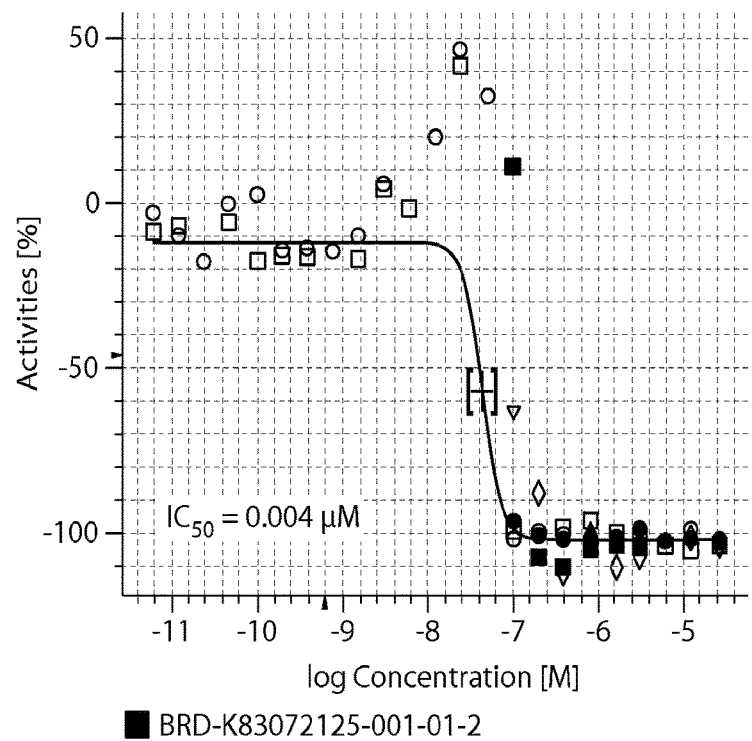
FIGS. 5A-C show the C. albicans and fibroblast dose response curves for probe compound I-B-4 (ML316). C. albicans CaCi-2 growth inhibition (AID 623899), IC$_{50}$=0.04 µM (FIG. 5A); C. albicans CaCi-17 growth inhibition (AID 623897), IC$_{50}$=1.0 µM (FIG. 5B); Murine 3T3 fibroblasts growth inhibition (AID 602394), IC50>26 µM (FIG. 5C); Dose curves were generated with Genedata Condeseo and show normalized percent activity for the individual doses.
Figure 5B:
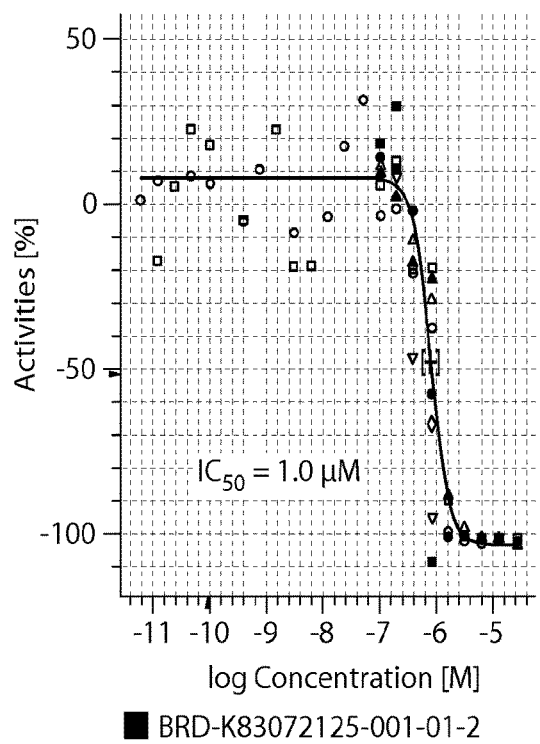
Figure 5C:
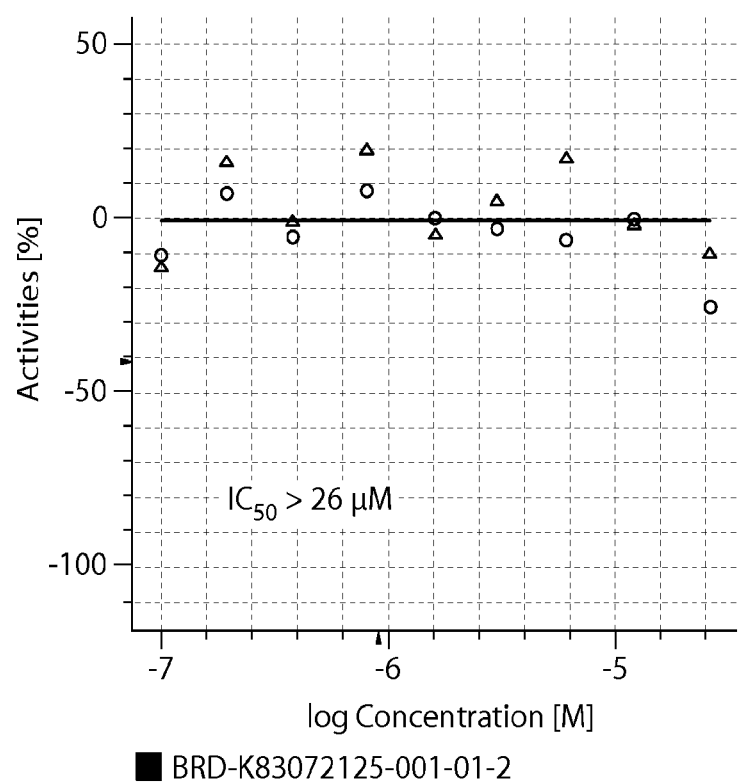
Figure 6A:
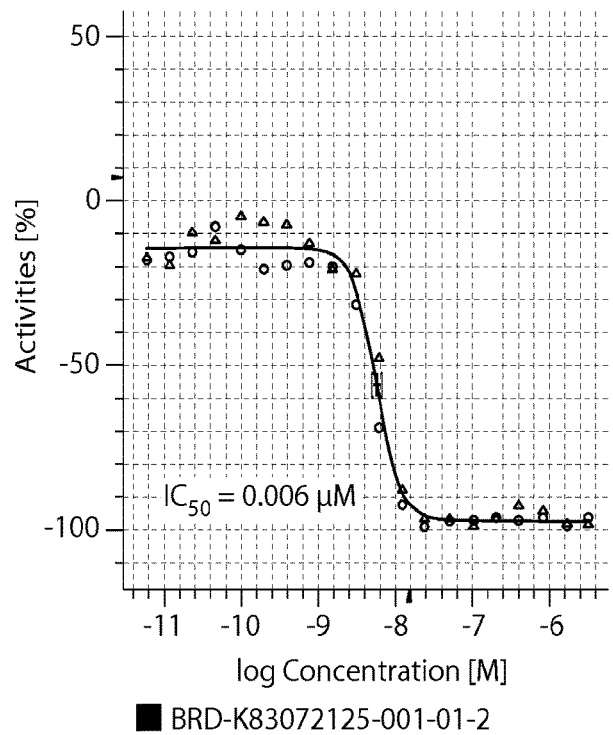
FIGS. 6A-D show the S. cerevisiae and C. glabrata dose response curves for probe compound I-B-4 (ML316). S. cerevisiae on glycerol growth inhibition (AID 623969), IC$_{50}$=0.004 µM (FIG. 6A); S. cerevisiae on glucose growth inhibition (AID 623971), IC50>3.0 µM (FIG. 6B); C. glabrata on glycerol growth inhibition (AID 623965), IC$_{50}$=0.011 µM (FIG. 6C); C. glabrata on glucose growth inhibition (AID 623967), IC$_{50}$>3.0 µM (FIG. 6D). Dose curves were generated with Genedata Condeseo and show normalized percent activity for the individual doses.
Figure 6B:
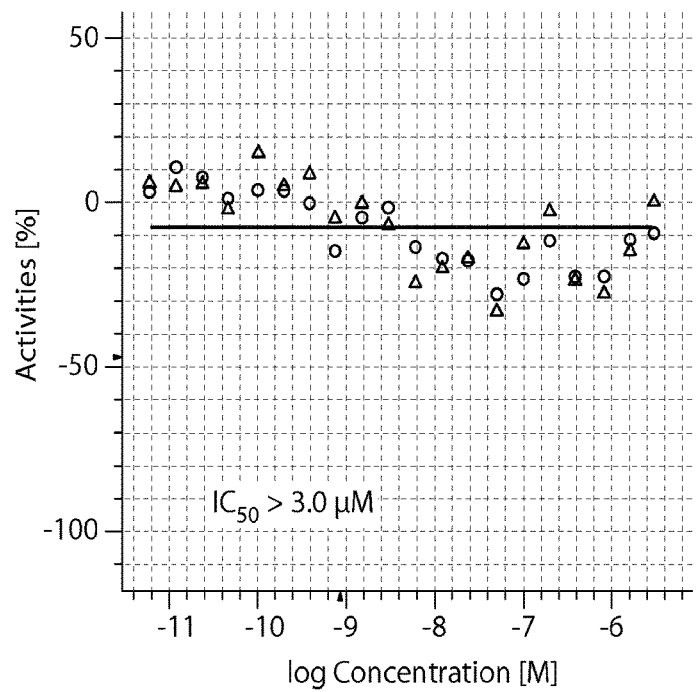
Figure 6C:
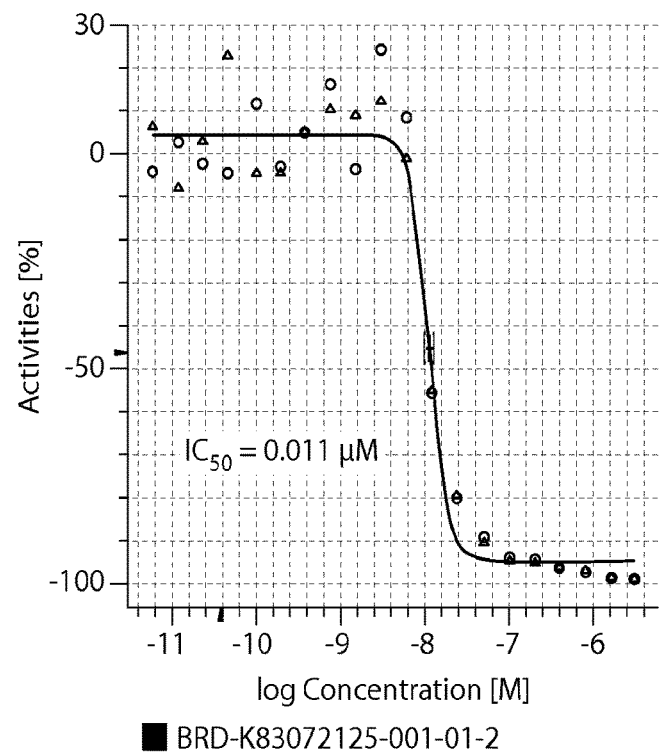
Figure 6D:
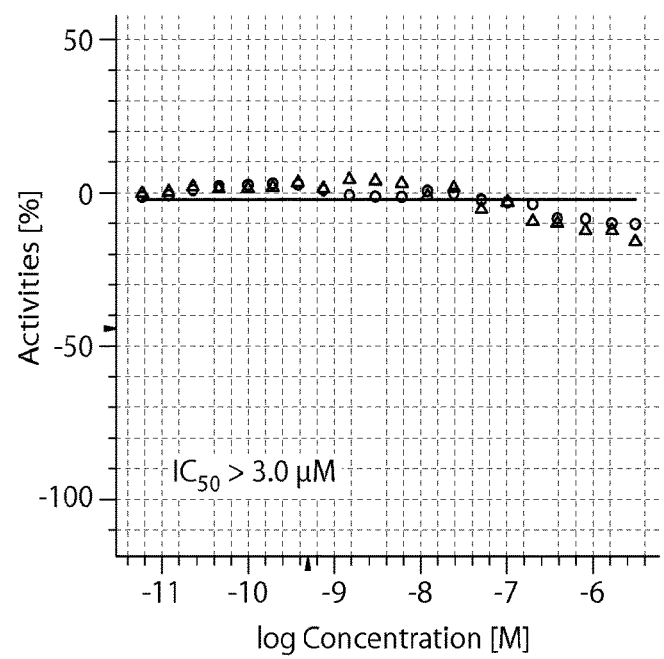

The dose response curves for probe compound I-B-4 (ML316) are shown in FIGS. 5-6.

SAR Tables

In order to investigate the activity of the hit (CID3889161), a collection of 51 structurally related analogs were synthesized and evaluated for their ability to inhibit growth in the *C. albicans* test strains. The biological assay data of these analogs are presented in Tables 3-8 (PubChem AIDs 623899, 623897, 602394).

The hit compound (CID3889161, Table 3, Entry 1) displayed significant activity against the *C. albicans* CaCi-2 strain ($IC_{50}$=0.3 µM), but was considerably less effective at inhibiting the growth of the more resistant CaCi-17 strain ($IC_{50}$=8.5 µM). There was also no noticeable toxicity to fibroblasts ($IC_{50}$>26 µM).

The importance of the ethyl carbamate was examined first, and the results are presented in Table 3. Alternative alkyl carbamates displayed moderate activity against CaCi-2 (Table 3, entries 2-5). Potency against this strain correlated with the size of the carbamate, and smaller alkyl chains were more effective. Except for the methyl carbamate derivative which only showed marginal activity, these analogs had no effect on CaCi-17 growth. Phenyl carbamate (Table 3, entry 6) showed no activity against either *C. albicans* strain. Replacing the nitrogen cap with other functionalities such as methyl sulfonamide, butyl amide, and N-alkyl chains did not confer additional antifungal activity (Table 3, entries 7-10). Similarly, the unsubstituted nitrogen failed to inhibit *C. albicans* growth (Table 3, entry 11).

While the substituent of the imide nitrogen seemed resistant to modification, the neighboring N-tolyl group was considerably more pliant (Table 4). Substitution at the phenyl ring's 4-position was not required for activity, and removing the methyl group appeared to improve potency against the more resistant CaCi-17 line (Table 4, entry 2). Conversely, incorporating methyl ether at that position attenuated the compound's effect on both *C. albicans* strains (Table 4, entry 3). Progressing to electron-deficient phenyl rings provided the most significant gains in potency (Table 4, entries 4-7). While the trifluoromethyl was the worst performer among the electron-withdrawing substituents examined, this analog was still only 2-fold weaker than the original hit. In comparison, the 4-fluoro, chloro, and cyano replacements were all 4 to 8-fold more effective against both CaCi-2 and CaCi-17. Comparison of positional effects showed that the location of the substituent has only a marginal influence on the compound's potency (Table 4, entries 8-9), although minor gains in PBS solubility were observed. The 4-ethyl and 4-propyl derivatives retain potency against CaCi-2 (Table 4, entries 10-11), but potency diminishes rapidly with larger substituents at this position (Table 4, entries 12-14). However, significantly smaller substituents are not effective growth inhibitors either (Table 4, entries 15-16). The N-benzyl analog showed a 10-fold drop in activity (Table 4, entry 17). The activity trends of this subset suggest the N-tolyl cap may lie within a sizeable pocket. While excessively large substituents attenuate activity, smaller functionalities (e.g. isopropyl or N—H) seem unable occupy this space effectively and therefore lower cellular activity.

Modification of the spirocyclic cyclohexane led to drastic reductions in activity (Table 5). Incorporating oxygen into the ring system provided a large increase in solubility, but this was accompanied by a 100-fold drop in potency (Table 5, entry 2). Substituting smaller aliphatic rings reiterated this trend; gains in solubility were offset by the inability to affect *C. albicans* growth (Table 5, entries 3-5).

Table 6 summarizes attempts to alter the underlying thiohydantoin core. Exchanging any of the chalcogens for other elements (O→N or S→O) eliminated cellular activity (Table 6, entries 2-3). Similarly, switching the nitrogen substituents produced an inactive derivative (Table 6, entry 4). N-alkyl hydantoins showed no ability to inhibit *C. albicans* growth (Table 6, entries 5-6) and neither did N-alkylated 4-thiohydantoins (Table 6, entries 7-8). Many intermediates prepared were also evaluated for antifungal activity, but none of these compounds were able to affect *C. albicans* (Table 7). The results summarized in Table 7 clearly demonstrate the importance of the carbamate (cf. Table 7, entries 7-8 & 10).

Six of the most potent inhibitors of *C. albicans*, including hit CID3889161, were then evaluated against *C. glabrata* and *S. cerevisiae* under different growth conditions to investigate their ability to perturb cellular respiration pathways in fungi (Table 8). All of the compounds tested were able to deter growth in both fungal strains at nanomolar concentrations ($IC_{50}$'s 0.006-0.058 µM) when the yeast were cultured on non-fermentable media. Conversely, yeast grown on a glucose-derived media showed considerable resistance to the test compounds ($IC_{50}$>3µM). Amphotericin B significantly inhibited *C. glabrata* and *S. cerevisiae* growth regardless of the growth media (Table 8, entry 7).

Of the analogs evaluated, the 4-fluoro derivative (CID56604860) demonstrated the most activity against the *C. albicans* test strains CaCi-2 ($IC_{50}$=0.04 µM) and CaCi-17 ($IC_{50}$=1.0 µM) (Table 4, entry 4). In addition, CID56604860 appears to disrupt cellular respiration processes of the fermenting yeast *C. glabrata* and *S. cerevisiae*. CID56604860 is a potent growth inhibitor of these species when only non-fermentable carbon sources are available ($IC_{50}$=0.011 and 0.004 µM, respectively), but its antifungal properties can be mitigated by permitting the yeast to ferment glucose ($IC_{50}$>3.0 µM) (Table 8, entry 3). Because of its impressive performance in these cellular assays, CID56604860 was nominated as the probe (compound I-B-4 (ML316)) for the respiration-selective growth inhibition of pathogenic fungi.

TABLE 3

SAR Analysis of Exemplary Compounds of Formula (I)

[Core structure: 1-(4-methylphenyl)-3-R-2-thioxo-1,3-diazaspiro[4.5]decan-4-one]

| Entry No. | CID / SID / Broad ID | R | PBS Solubility (μM) | C. albicans CaCi-2 (n=3) | C. albicans CaCi-17 (n=3) | 3T3 Fibroblasts (n=1) |
|---|---|---|---|---|---|---|
| 1 | 3889161 / 131404760 / BRD-K97464451-001-02-7 | –C(O)OCH$_2$Me | <1.0 | 0.3 | 8.5 | Inactive |
| 2 | 3951437 / 134356653 / BRD-K26272324-001-01-7 | –C(O)OMe | 1.2 | 1.9 | 17.1 | Inactive |
| 3 | 56604849 / 134356659 / BRD-K19100570-001-01-0 | –C(O)OCH$_2$CH$_2$Me | <1.0 | 1.2 | inactive | Inactive |
| 4 | 56604859 / 134356634 / BRD-K65907975-001-01-2 | –C(O)OCH(Me)Me | <1.0 | 5.9 | inactive | Inactive |
| 5 | 656604866 / 134356630 / BRD-K98528213-001-01-9 | –C(O)OCH$_2$Ph | <1.0 | inactive | inactive | 7.0 |
| 6 | 56604875 / 134356666 / BRD-K53670532-001-01- | –C(O)OPh | <1.0 | inactive | inactive | Inactive |
| 7 | 56604886 / 134356649 / BRD-K03429132-001-01-2 | –S(O)$_2$Me | 29 | inactive | inactive | Inactive |
| 8 | 56604869 / 134356667 / BRD-K80955814-001-01-7 | –C(O)CH$_2$CH$_2$Me | 2.2 | inactive | inactive | 18.8 |
| 9 | 56604814 / 134356625 / BRD-K89849897-001-01-3 | –CH$_2$CH$_2$CH$_2$Me | <1.0 | inactive | inactive | 24.2 |

Growth Inhibition Activity, IC$_{50}$ (μM)$^†$

TABLE 3-continued

SAR Analysis of Exemplary Compounds of Formula (I)

| Entry No. | CID SID Broad ID | R | PBS Solubility (μM) | C. albicans (n = 3) CaCi-2 | CaCi-17 | 3T3 Fibroblasts (n = 1) |
|---|---|---|---|---|---|---|
| 10 | 56604835 134356654 BRD-K32391448-001-01-8 |  | 6.6 | inactive | inactive | Inactive |
| 11 | 56604892 134356619 BRD-K14153519-001-01-8 | 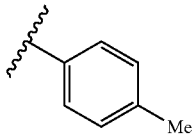 [SMILES: *c1ccc(C)cc1] | 7.8 | inactive | inactive | Inactive |

†Inactive compounds showed no significant activity when tested below 26 μM.

TABLE 4

SAR Analysis of Exemplary Compounds of Formula (I)

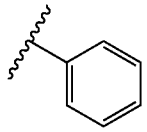 [SMILES: *c1ccccc1]

| Entry No. | CID SID Broad ID | R | PBS Solubility (μM) | C. albicans (n = 3) CaCi-2 | CaCi-17 | 3T3 Fibroblasts (n = 1) |
|---|---|---|---|---|---|---|
| 1 | 3889161 131404760 BRD-K97464451-001-02-7 | 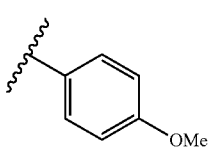 [SMILES: *c1ccc(OC)cc1] | <1.0 | 0.3 | 8.5 | Inactive |
| 2 | 56604821 134356644 BRD-K49254495-001-01-1 | | 1.6 | 0.2 | 4.2 | Inactive |
| 3 | 56604819 134356620 BRD-K86579583-001-01-8 | | <1.0 | 1.8 | inactive | Inactive |

TABLE 4-continued

SAR Analysis of Exemplary Compounds of Formula (I)

| Entry No. | CID SID Broad ID | R | PBS Solubility (μM) | C. albicans (n = 3) CaCi-2 | C. albicans (n = 3) CaCi-17 | 3T3 Fibroblasts (n = 1) |
|---|---|---|---|---|---|---|
| 4 | 56604860 134356650 BRD-K83072125-001-01-2 | 4-F-C6H4 | 1.1 | 0.04‡ | 1.0 | Inactive |
| 5 | 56604865 134356623 BRD-K39763022-001-01-5 | 4-Cl-C6H4 | <1.0 | 0.06‡ | 1.4 | 22.3 |
| 6 | 56604813 134356635 BRD-K52387572-001-01-9 | 4-CF3-C6H4 | <1.0 | 0.8 | 16.2 | 12.5 |
| 7 | 56604847 134356662 BRD-K50804393-001-01-2 | 4-CN-C6H4 | <1.0 | 0.08‡ | 1.8 | Inactive |
| 8 | 24052146 134356624 BRD-K36592023-001-01-0 | 2-Me-C6H4 | 18 | 1.2 | 23.9 | Inactive |
| 9 | 56604823 134356628 BRD-K16218093-001-01-1 | 3-Me-C6H4 | 2.6 | 0.2 | 8.2 | 24.2 |
| 10 | 56604836 134356632 BRD-K00266879-001-01-8 | 4-CH2Me-C6H4 | <1.0 | 1.9 | inactive | 19.5 |
| 11 | 56604858 134356652 BRD-K16262788-001-01-9 | 4-CH2CH2Me-C6H4 | <1.0 | 6.9 | inactive | Inactive |

TABLE 4-continued

SAR Analysis of Exemplary Compounds of Formula (I)

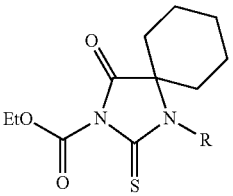

| Entry No. | CID SID Broad ID | R | PBS Solubility (μM) | Growth Inhibition Activity, IC$_{50}$ (μM)[†] | | 3T3 Fibroblasts (n = 1) |
| --- | --- | --- | --- | --- | --- | --- |
| | | | | *C. albicans* (n = 3) | | |
| | | | | CaCi-2 | CaCi-17 | |
| 12 | 56604817 134356638 BRD-K05712817-001-01-1 | 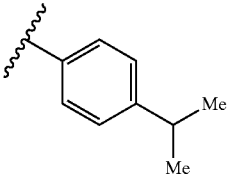 [SMILES: *c1ccc(C(C)C)cc1] | <1.0 | inactive | inactive | 13.8 |
| 13 | 56604837 134356629 BRD-K05074617-001-01-8 | 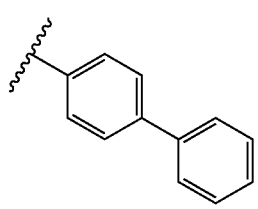 [SMILES: *c1ccc(-c2ccccc2)cc1] | <1.0 | inactive | inactive | 16.5 |
| 14 | 56604882 134356647 BRD-K01156547-001-01-2 | 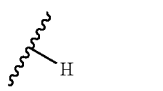 | <1.0 | inactive | inactive | 9.8 |
| 15 | 56604830 134356618 BRD-K23441366-001-01-0 | H | 61 | inactive | inactive | Inactive |
| 16 | 56604896 134356656 BRD-K23097153-001-01-7 | 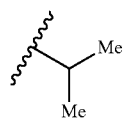 | 12 | inactive | inactive | Inactive |
| 17 | 56604878 134356658 BRD-K43828902-001-01-5 | 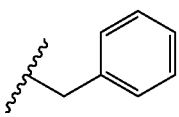 [SMILES: *Cc1ccccc1] | 7.2 | 3.8 | 22.8 | Inactive |

[†]Inactive compounds showed no significant activity when tested below 26 μM.

[‡]For this compound, n = 6. The IC$_{50}$ value was determined to be less than 0.10 μM from three independent runs, performed in duplicate (n = 3, PubChem AID 623899). Subsequent re-tests at lower concentrations were used to calculate the reported IC$_{50}$ value (n = 3, PubChem AIDs 623981, 624006).

TABLE 5

SAR Analysis of Exemplary Compounds of Formula (I)

| Entry No. | CID SID Broad ID | R | PBS Solubility (μM) | Growth Inhibition Activity, IC$_{50}$ (μM)[†] | | 3T3 Fibroblasts (n = 1) |
|---|---|---|---|---|---|---|
| | | | | *C. albicans* (n = 3) | | |
| | | | | CaCi-2 | CaCi-17 | |
| 1 | 3889161 131404760 BRD-K97464451-001-02-7 | cyclohexyl | <1.0 | 0.3 | 8.5 | Inactive |
| 2 | 56604818 134356640 BRD-K45116687-001-01-4 | tetrahydropyranyl | 28.5 | 20.6 | inactive | Inactive |
| 3 | 56604843 134356657 BRD-K27513748-001-01-1 | cyclopentyl | 9.2 | 9.8 | inactive | Inactive |
| 4 | 56604894 134356661 BRD-K83367276-001-01-3 | cyclobutyl | 9.9 | Inactive | inactive | Inactive |
| 5 | 56604873 134356665 BRD-K82164803-001-01-7 | C(Me)$_2$ | 45.3 | inactive | inactive | Inactive |

[†]Inactive compounds showed no significant activity when tested below 26 μM.

TABLE 6

Modifications of the Thiohydantoin Core

| Entry No. | CID SID Broad ID | Structure | PBS Solubility (μM) | Growth Inhibition Activity, IC$_{50}$ (μM)[†] | | 3T3 Fibroblasts (n = 1) |
| --- | --- | --- | --- | --- | --- | --- |
| | | | | *C. albicans* (n = 3) | | |
| | | | | CaCi-2 | CaCi-17 | |
| 1 | 3889161 131404760 BRD-K97464451-001-02-7 | | <1.0 | 0.3 | 8.5 | Inactive |
| 2 | 56604827 134356639 BRD-K51126930-001-01-9 | | 55 | inactive | inactive | Inactive |
| 3 | 56604867 134356626 BRD-K04998372-001-01-4 | | 26 | inactive | inactive | Inactive |
| 4 | 56604852 134356655 BRD-K81345344-001-01-9 | | <1.0 | inactive | inactive | Inactive |
| 5 | 56604845 134356664 BRD-K57101886-001-01-0 | | 100 | inactive | inactive | Inactive |
| 6 | 56604877 134356636 BRD-K60902532-001-01-4 | | 64 | inactive | inactive | Inactive |

TABLE 6-continued

Modifications of the Thiohydantoin Core

| Entry No. | CID SID Broad ID | Structure | PBS Solubility (μM) | Growth Inhibition Activity, IC$_{50}$ (μM)[†] | | 3T3 Fibroblasts (n = 1) |
|---|---|---|---|---|---|---|
| | | | | C. albicans (n = 3) | | |
| | | | | CaCi-2 | CaCi-17 | |
| 7 | 56604857 134356617 BRD-K41190721-001-01-1 | 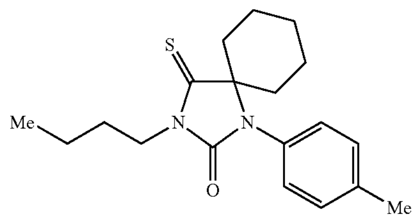 [SMILES: CCCCN1C(=O)N(c2ccc(C)cc2)C2(CCCCC2)C1=S] | <1.0 | inactive | inactive | 20.9 |

[†]Inactive compounds showed no significant activity when tested below 26 μM.

TABLE 7

Bioactivity of Various Intermediates

| Entry No. | CID SID Broad ID | Structure | PBS Solubility (μM) | Growth Inhibition Activity, IC$_{50}$ (μM)[†] | | 3T3 Fibroblasts (n = 1) |
|---|---|---|---|---|---|---|
| | | | | C. albicans (n = 3) | | |
| | | | | CaCi-2 | CaCi-17 | |
| 1 | 3889161 131404760 BRD-K97464451-001-02-7 | 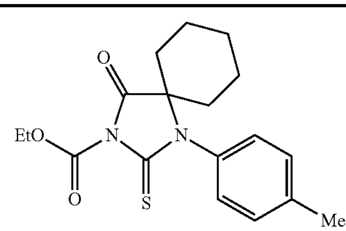 | <1.0 | 0.3 | 8.5 | Inactive |
| 2 | 56604883 134356663 BRD-K15707586-001-01-8 | 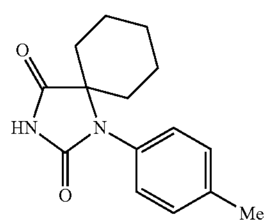 [SMILES: Cc1ccc(N2C(=O)NC(=O)C23CCCCC3)cc1] | 14 | inactive | inactive | Inactive |
| 3 | 56604884 134356642 BRD-K51157407-001-01-8 | 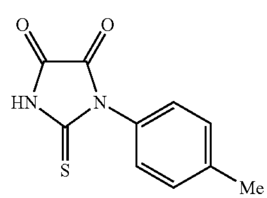 [SMILES: Cc1ccc(N2C(=O)C(=O)NC2=S)cc1] | 21 | inactive | inactive | Inactive |
| 4 | 56604829 134356622 BRD-K69099108-001-01-4 | 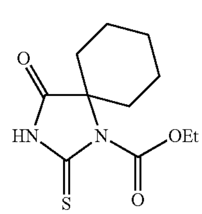 [SMILES: CCOC(=O)N1C(=S)NC(=O)C12CCCCC2] | >100 | inactive | inactive | Inactive |

TABLE 7-continued

Bioactivity of Various Intermediates

| Entry No. | CID<br>SID<br>Broad ID | Structure | PBS Solubility (μM) | Growth Inhibition Activity, IC$_{50}$ (μM)$^\dagger$ | | 3T3 Fibroblasts (n = 1) |
|---|---|---|---|---|---|---|
| | | | | *C. albicans* (n = 3) | | |
| | | | | CaCi-2 | CaCi-17 | |
| 5 | 56604856<br>134356646<br>BRD-K54655126-001-01-8 | | 5.9 | inactive | inactive | Inactive |
| 6 | 56604841<br>134356648<br>BRD-K28436532-001-01-4 | | >100 | inactive | inactive | Inactive |
| 7 | 56604862<br>134356631<br>BRD-K16604305-001-01-6 | | 43 | inactive | inactive | Inactive |
| 8 | 823120<br>134356621<br>BRD-K77788822-001-01-7 | | 79 | inactive | inactive | Inactive |
| 9 | 56604820<br>134356637<br>BRD-K41378710-001-01-5 | | 32 | inactive | inactive | Inactive |
| 10 | 14297244<br>134356660<br>BRD-K97666538-001-01-6 | | >100 | inactive | inactive | Inactive |

TABLE 7-continued

Bioactivity of Various Intermediates

| Entry No. | CID<br>SID<br>Broad ID | Structure | PBS Solubility (μM) | Growth Inhibition Activity, IC$_{50}$ (μM)[†] | | 3T3 Fibroblasts (n = 1) |
|---|---|---|---|---|---|---|
| | | | | *C. albicans* (n = 3) | | |
| | | | | CaCi-2 | CaCi-17 | |
| 11 | 56604885<br>134356641<br>BRD-K48843907-001-01-4 | 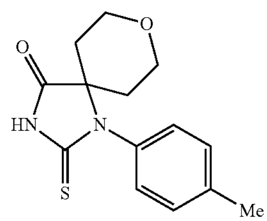 [SMILES: Cc1ccc(N2C(=S)NC(=O)C23CCOCC3)cc1] | >100 | inactive | inactive | Inactive |
| 12 | 56604876<br>134356668<br>BRD-K01920745-001-01-1 | 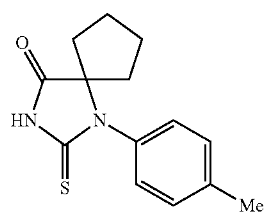 [SMILES: Cc1ccc(N2C(=S)NC(=O)C23CCCC3)cc1] | 72 | inactive | inactive | 32.6 |
| 13 | 56604811<br>134356643<br>BRD-K83470897-001-01-4 | 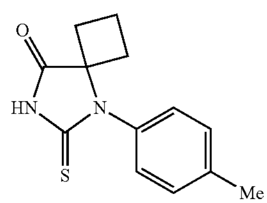 [SMILES: Cc1ccc(N2C(=S)NC(=O)C23CCC3)cc1] | 62 | inactive | inactive | Inactive |
| 14 | 56604879<br>134356651<br>BRD-K33397992-001-01-4 | 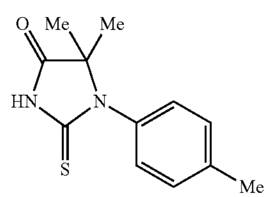 [SMILES: Cc1ccc(N2C(=S)NC(=O)C2(C)C)cc1] | 55 | inactive | inactive | Inactive |
| 15 | 56604844<br>134356645<br>BRD-K10211459-001-01-0 | 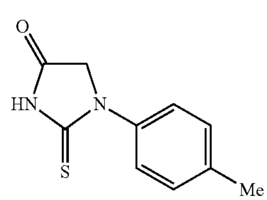 [SMILES: Cc1ccc(N2CC(=O)NC2=S)cc1] | <1.0 | inactive | inactive | 20.7 |
| 16 | 759335<br>134356627<br>BRD-K28884125-001-01-8 | 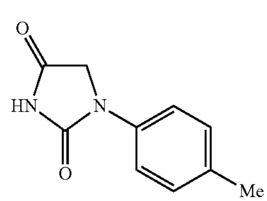 [SMILES: Cc1ccc(N2CC(=O)NC2=O)cc1] | >100 | inactive | inactive | Inactive |

[†]Inactive compounds showed no significant activity when tested below 26 μM.

TABLE 8

Growth Media-Dependent Activity of *C. Albicans* Active Analogs

| Entry No. | CID<br>SID<br>Broad ID | Structure | Growth Inhibition Activity, IC$_{50}$ (µM) | | | |
|---|---|---|---|---|---|---|
| | | | *C. glabrata* (n = 3) | | *S. cerevisiae* (n = 3) | |
| | | | On glycerol | On glucose | On glycerol | On glucose |
| 1 | 3889161<br>131404760<br>BRD-K97464451-001-02-7 | (structure: hydantoin-thione with cyclohexyl spiro, N-ethoxycarbonyl, N-(4-methylphenyl)) | 0.041 | >3.0 | 0.011 | >3.0 |
| 2 | 56604821<br>134356644<br>BRD-K49254495-001-01-1 | (structure: hydantoin-thione with cyclohexyl spiro, N-ethoxycarbonyl, N-phenyl) | 0.026 | >3.0 | 0.015 | >3.0 |
| 3 | 56604860<br>134356650<br>BRD-K83072125-001-01-2 | (structure: hydantoin-thione with cyclohexyl spiro, N-ethoxycarbonyl, N-(4-fluorophenyl)) | 0.011 | >3.0 | 0.004 | >3.0 |
| 4 | 56604865<br>134356623<br>BRD-K39763022-001-01-5 | (structure: hydantoin-thione with cyclohexyl spiro, N-ethoxycarbonyl, N-(4-chlorophenyl)) | 0.022 | >3.0 | 0.006 | >3.0 |
| 5 | 56604847<br>134356662<br>BRD-K50804393-001-01-2 | (structure: hydantoin-thione with cyclohexyl spiro, N-ethoxycarbonyl, N-(4-cyanophenyl)) | 0.033 | >3.0 | 0.004 | >3.0 |
| 6 | 56604823<br>134356628<br>BRD-K16218093-001-01-1 | (structure: hydantoin-thione with cyclohexyl spiro, N-ethoxycarbonyl, N-(3-methylphenyl)) | 0.034 | >3.0 | 0.019 | >3.0 |
| 7 | 46897897<br>99351062<br>BRD-A42129474-001-02-7 | Amphotericin B | 0.62 | 1.2 | 0.26 | 0.38 |

Cellular Activity

Both primary assays were performed with whole cells. One secondary screen evaluating toxicity utilized murine 3T3 fibroblast cells, and growth inhibition assays of whole S. cerevisiae and C. glabrata on different media were included as additional secondary assays. An overview of the assays and full experimental details are described herein. The probe (CID56604860/compound I-B-4 (ML316)) met the established cellular activity criteria specified for this project (Table 9).

TABLE 9

Comparison of Probe Compound I-B-4 (ML316) to Project Criteria

| No. | Property | CPDP Requirement | I-B-4 (ML316) |
|---|---|---|---|
| 1 | C. albicans CaCi-2 growth inhibition | $IC_{50} \leq 10$ μM | 0.04 μM |
| 2 | C. albicans CaCi-17 growth inhibition | $IC_{50} \leq 10$ μM | 1.0 μM |
| 3 | Growth inhibition of S. cerevisiae on glycerol | $IC_{50} \leq 10$ μM | 0.004 μM |
| 4 | Growth inhibition of S. cerevisiae on glucose | $\geq 10X$ glycerol $IC_{50}$ | >3.0 μM |
| 5 | Growth inhibition of C. glabrata on glycerol | $IC_{50} \leq 10$ μM | 0.011 μM |
| 6 | Growth inhibition of C. glabrata on glucose | >10X glycerol $IC_{50}$ | >3.0 μM |
| 7 | Fibroblast growth inhibition | $IC_{50} \leq 20$ μM | >26 μM |

4.8. Discussion

Publicly available data from the NIH's PubChem repository facilitated an abbreviated screening campaign for the current project. 302,509 compounds from the NIH's screening collection had been previously evaluated for inhibitory activity against C. albicans CaCi-2 (AIDs 1979, 2387) as well as 3T3 mammalian fibroblasts (AID 2327), and cross-referencing this data identified 67 compounds demonstrating acceptable potency against CaCi-2 that were also reasonably non-toxic towards fibroblasts. After dry powder validation of these candidates, thiohydantoin CID3889161 was selected as a priority scaffold for further investigation.

Figure 7:
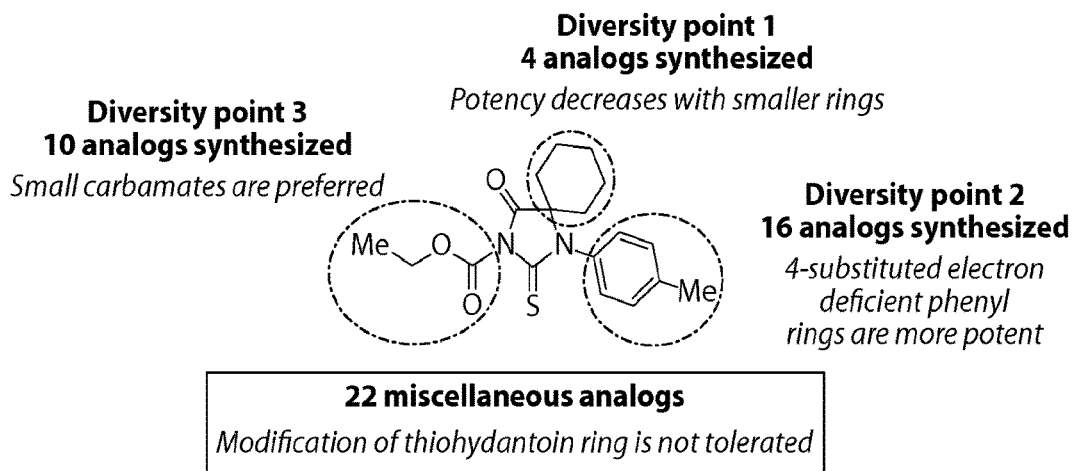
FIG. 7 depicts the SAR (structure-activity relationship) strategy based on the initial hit compound I-A-1 (CID3889161). Key SAR findings for each site of diversification are provided in italics.

Over 50 derivatives of CID3889161 were synthetically prepared and evaluated for antifungal activity against two Candida albicans clinical isolates, CaCi-2 and CaCi-17. Both strains have demonstrated resistance towards the commonly prescribed antimycotic fluconazole, with CaCi-17 being significantly more resistant than CaCi-2. In addition to fungal growth inhibition, these analogs were screened for non-specific toxicity using murine 3T3 fibroblasts. FIG. 7 summarizes the various modifications explored during SAR studies. Three primary diversity points were investigated, and the number of analogs prepared for each location is reported in FIG. 7. Several analogs do not fit into these three clusters and are classified as "miscellaneous" analogs.

From the SAR study, it was determined that carbamates were the preferred substituent for the imide nitrogen and that the ethyl carbamate was optimal. Electron-deficient phenyl rings are superior to the original N-tolyl group, while ortho- and meta-substituents do not appear to significantly influence cellular activity. Contracting the cyclohexyl ring system provides increases in solubility while diminishing antifungal potency. While some variation of the nitrogen substituents is tolerated, the modification of the underlying thiohydantoin motif is not. The 4-fluorophenyl analog I-B-4 (CID56604860) emerged from these studies as the most potent antifungal of this class. Subsequent investigation of compound I-B-4 revealed that its antifungal properties could be modulated by the specific growth media given to the fungal test strains, as desired by the project criteria. Consequently, compound I-B-4 was nominated as the probe compound I-B-4 (ML316).

Based on the project goals summarized below in Table 9, the probe compound I-B-4 clearly surpasses all of the specified criteria. Compound I-B-4 possesses potent activity against the C. albicans test strains CaCi-2 ($IC_{50}$=0.04 μM) and CaCi-17 ($IC_{50}$=1.0 μM). In addition, compound I-B-4 is a potent growth inhibitor of C. glabrata and S. cerevisiae when only non-fermentable carbon sources are available ($IC_{50}$=0.011 and 0.004 μM, respectively), but its antifungal properties are lost when the yeast is supplied glucose for fermentation ($IC_{50}$>3.0 μM). There is no apparent toxicity against mammalian fibroblasts at concentrations up to 26 μM, indicating that compound I-B-4 may be a fungal selective, respiratory inhibitor.

According to PubChem, compound I-B-4 (ML316, CID56604860) has not been tested in any other assay reported to its database. The original hit, compound I-A-1 (CID3889161), has been evaluated in seven assays. All seven assays are associated with the original screening campaign (AID 2007) from which the current project is derived. The cellular activity of ompound I-A-1 (CID3889161) described herein recapitulates the published PubChem data.

A search of the available literature identified several compounds capable of disrupting fungal respiration (von Jagow et al., Methods Enzymol. 1986, 126:253-71; Ueki et al., Curr. Opin. Anti-Infective Invest. Drugs 2000, 2(4):387-398; Sridhara et al., J. Pharmaceutical. Res. 2011, 4(2):496-500; Mathre, Pest Biochem. Physiol. 1971, 1(2):216-224). With the exception of ilicicolin H, these compounds do not show appreciable selectivity towards fungi over mammalian targets or cells. Hence, it was decided to compare the probe compound I-B-4 (ML316) with ilicicolin H.

Previous work with the antifungal antibacterial ilicicolin H has shown that this natural product is a potent inhibitor of the mitochondrial cytochrome $bc_1$ complex (Gutierrez-Cirlos et al., J. Biol. Chem. 2004, 279(10):8708-14; Rotsaert et al., Biochim. Biophys. Acta 2008, 1777(2):211-9). Using purified proteins, Trumpower et al. determined that ilicicolin H binds to the S. cerevisiae enzyme complex with almost 100-fold greater selectivity than the corresponding bovine homolog. This selectivity has not been reproduced within a cell-based assay.

A commercial sample of ilicicolin H was procured from Analyticon Discovery and determined to be approximately 85% pure by HPLC. The commercial sample was purified by column chtomatography over silica gel prior to testing in cellular assays. It was recently attempted to obtain additional quantities of ilicicolin H but discovered that this compound is no longer commercially available.

Probe compound I-B-4 (ML316) was tested alongside ilicicolin H in a direct comparison of biological activity. The results are summarized below in Table 10. Compound I-B-4 (ML316) clearly shows a stronger inhibitory effect upon Candida albicans growth than ilicicolin H. While both compounds show differential activity relative to growth media, the distinction is far less pronounced with ilicicolin H regardless of the fungal test strain.

Given the complex structure of ilicicolin H, optimization of biological and physical properties through synthetic methods will be difficult. Despite having been isolated 40 years ago (Hayakawa et al., J. Antibiot. 1971, 24(9):653-4), the first and only total synthesis of the ilicicolin H was reported in 1985 (Williams et al., J. Org. Chem. 1985, 50(15):2807-9). That this pioneering synthesis produced racemic material further underscores the inherent difficulties of preparing analogs of this compound. While semi-synthetic analogs are possible (Liu et al., Tetrahedron Lett. 2005, 46(46): 8009-12; Singh et al., Tetrahedron Lett. 2011, 52(46): 6190-1), the lack of a commercial feedstock renders this option untenable at the present time.

As a small molecule probe, compound I-B-4 (ML316) is the superior compound because of its cellular potency and selectivity, and its simple preparation and chemical tractability facilitate further optimization.

TABLE 10

Comparison of Probe Compound I-B-4 (ML316) to Prior Art Compound Ilicicolin H

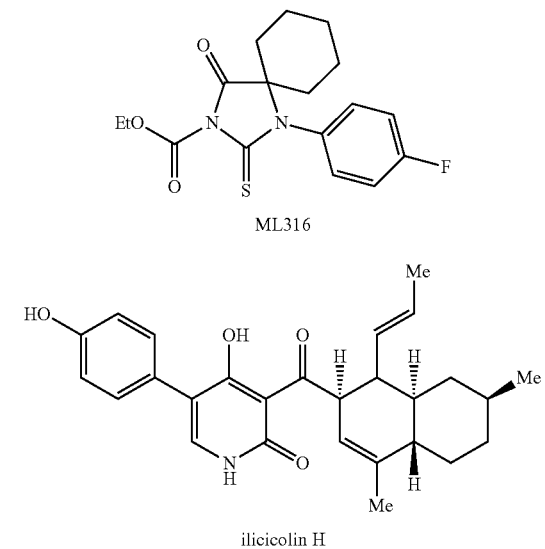

| No. | Property | ML316 (I-B-4) | ilicicolin H |
|---|---|---|---|
| 1 | C. albicans CaCi-2 growth inhibition | 0.04 µM | >3.0 µM |
| 2 | C. albicans CaCi-17 growth inhibition | 1.0 µM | >3.0 µM |
| 3 | Growth inhibition of S. cerevisiae on glycerol | 0.004 µM | 0.03 µM |
| 4 | Growth inhibition of S. cerevisiae on glucose | >3.0 µM | >3.0 µM |
| 5 | Growth inhibition of C. glabrata on glycerol | 0.011 µM | 2.6 µM |
| 6 | Growth inhibition of C. glabrata on glucose | >3.0 µM | >3.0 µM |
| 7 | Fibroblast growth inhibition | >26 µM | 10.0 µM |
| 8 | PBS solubility (with 1% v/v DMSO) | 1.1 µM | <1.0 µM |

Mechanism of Action Studies

A series of secondary assays were performed to interrogate the possible mode of action. Compound I-B-4 (ML316) appears to disrupt cellular respiration of fungal organisms as demonstrated by the distinctly different growth patterns of C. glabrata and S. cerevisiae when they are fed fermentable and non-fermentable carbon sources. In both species, compound I-B-4 (ML316) is most effective when the yeast are given glycerol and displays a greater than 250-fold reduction in potency when glucose is available.

Additionally, direct impairment of mitochondrial function in C. glabrata and S. cerevisiae was assessed using a fluorescence assay. Application of JC-1 dye to living S. cerevisiae treated with 1 µM compound I-B-4 (ML316) determined that depolarization of the mitochondrial membrane does not occur (PubChem AIDs 624062, 624068). Comparison of the DMSO controls with compound I-B-4 suggests the yeast can still maintain their normal mitochondrial membrane potential; it appears that the molecular target of ML316 may be integrated within an alternative metabolic pathway that fungi utilize for respiration (Ferrari et al., PLoS Pathog. 2009, 5(1):e1000268).

Example 5

Biological Assays of Compound I-B-4 (ML316)

Figure 8:
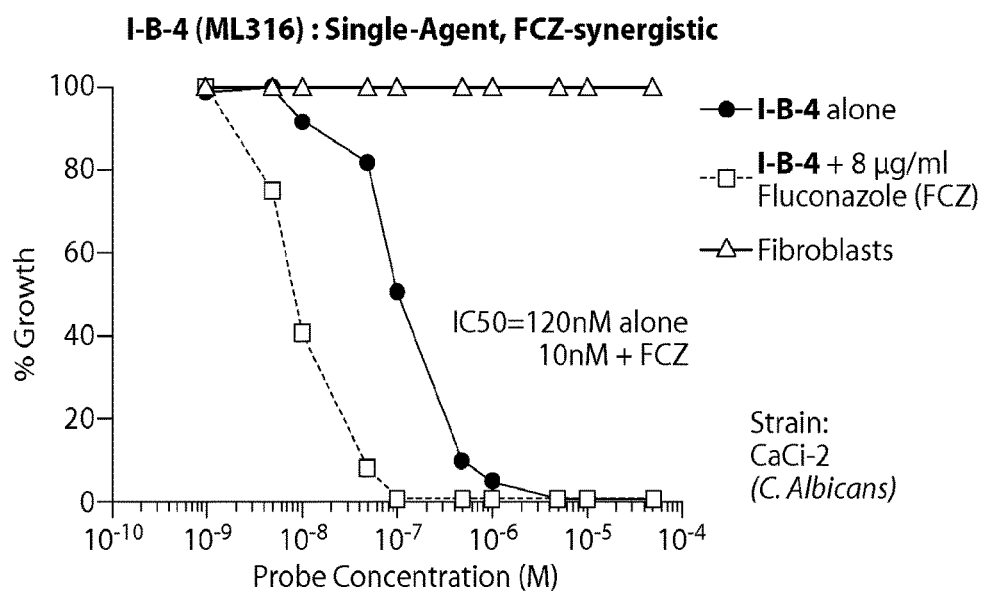
FIG. 8 shows the inhibitory activities of compound I-B-4 (ML316) against C. albicans CaCi-2 growth in absence and presence of fluconazole (FCZ). IC$_{50}$=120 nM for I-B-4 (ML316) alone. IC50=10 nM for I-B-4 (ML316) with FCZ.

5.1. Materials and Methods
 Materials and Reagents.
 Cell Lines.
  Candida albicans CaCi-2; a drug-resistant clinical isolate was provided by the Whitehead Institute (Redding et al., Clin. Infect. Dis. 1994, 18(2):240-2). This strain was used for the primary assay.
  Candida albicans strain SC5314
  Candida albicans ATCC 200950
  S. cerevisiae strain BY4743; BY4743+pRS316-MIR1; BY4743 MIR1Δ/+; BY4743+pRS316-MIR1N184T; BY4741 mir1Δ
 Procedures Growth inhibition of I-B-4 (ML316) against Candida albicans CaCi-2 in the presence or absence of fluconazole was assessed using the broth microdilution method with RPMI media. FIG. 8 summarizes the inhibitory activities ($IC_{50}$=120 nM for I-B-4 (ML316) alone; IC50=10 nM for I-B-4 (ML316) with FCZ).

Figure 9:
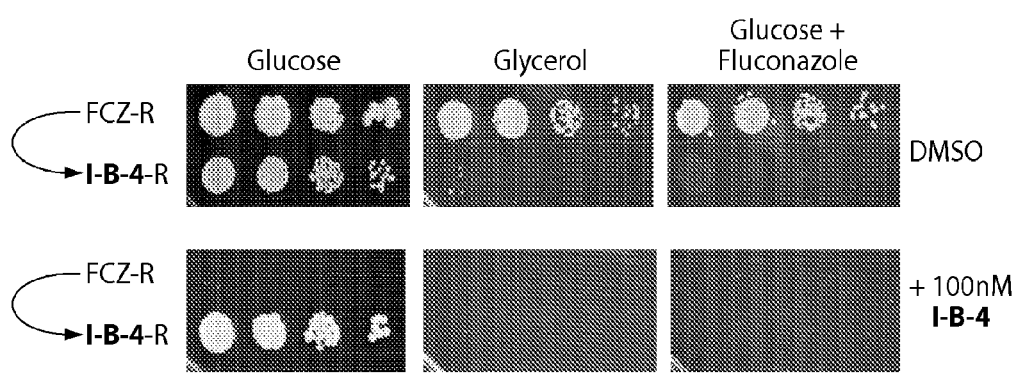
FIG. 9 shows the interaction of I-B-4 (ML316) with fluconazole against C. albicans CaCi-2 (FCZ-R). Strain "I-B-4-R" is a derivative of the CaCi-2 strain selected for resistance to I-B-4 (ML316). These data show that Candida from a fluconazole-resistant background that evolves resistance to I-B-4 (ML316) loses the ability to grow on glycerol media (indicative of a loss of respiration) and becomes hypersensitive to fluconazole (32 µg/mL).

Growth of Candida albicans CaCi-2 and derived I-B-4-R strain were assessed on solid agar media containing yeast nitrogen base with either 2% glucose or 2% glycerol as carbon source; I-B-4 was included as indicated at 100 nM; fluconazole was included at 32 µg/mL. Photos were taken after 2 days of growth at 37° C. FIG. 9 shows the results of the growth assessment.

Figure 10:
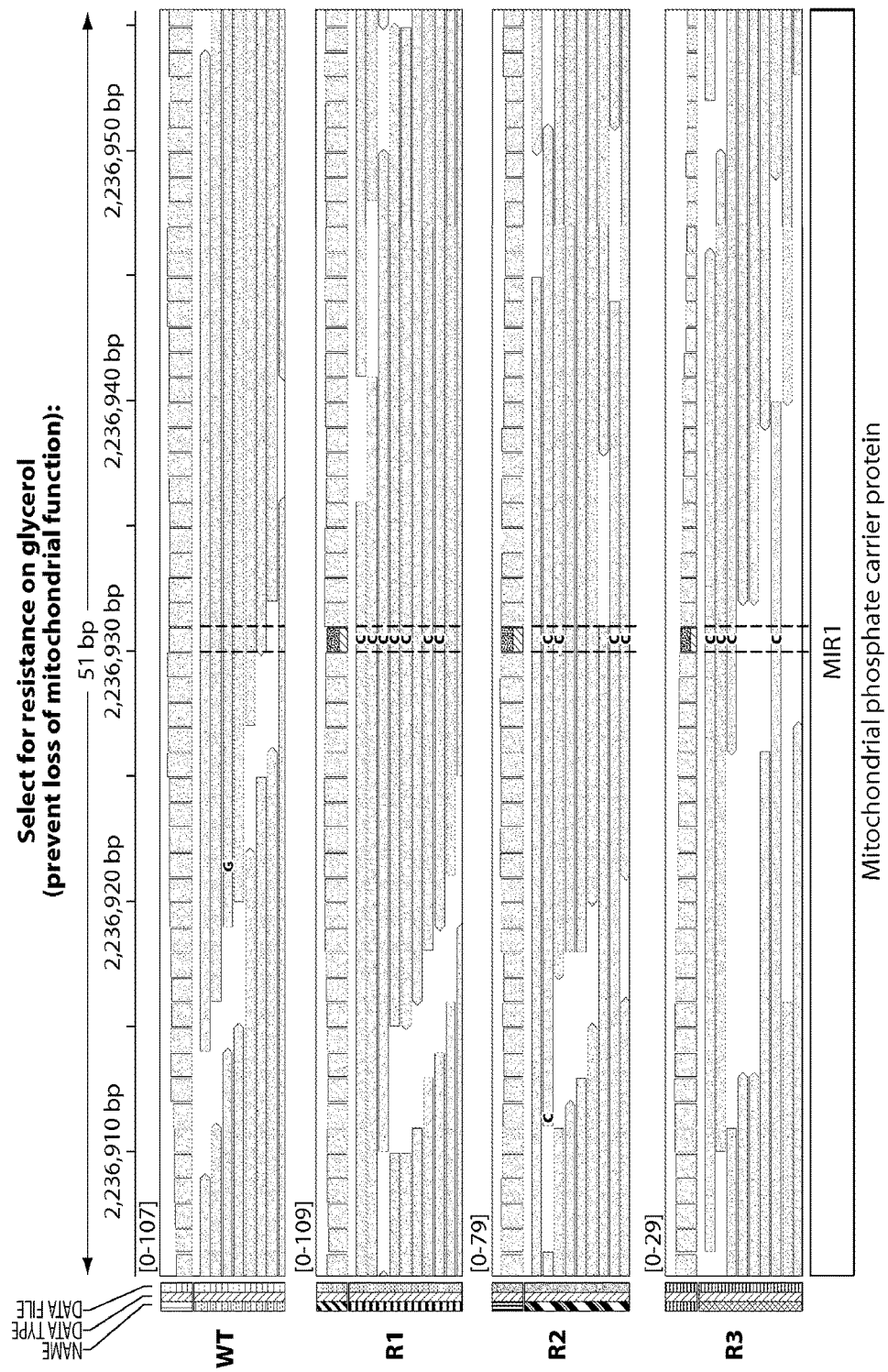
FIG. 10 shows results of genome sequencing of three independent selections in C. albicans ATCC 200950 for resistance to I-B-4 (ML316); in all three selections, the same mutation in the MIR1 protein (N184T) emerged.
Figures 11, 12:
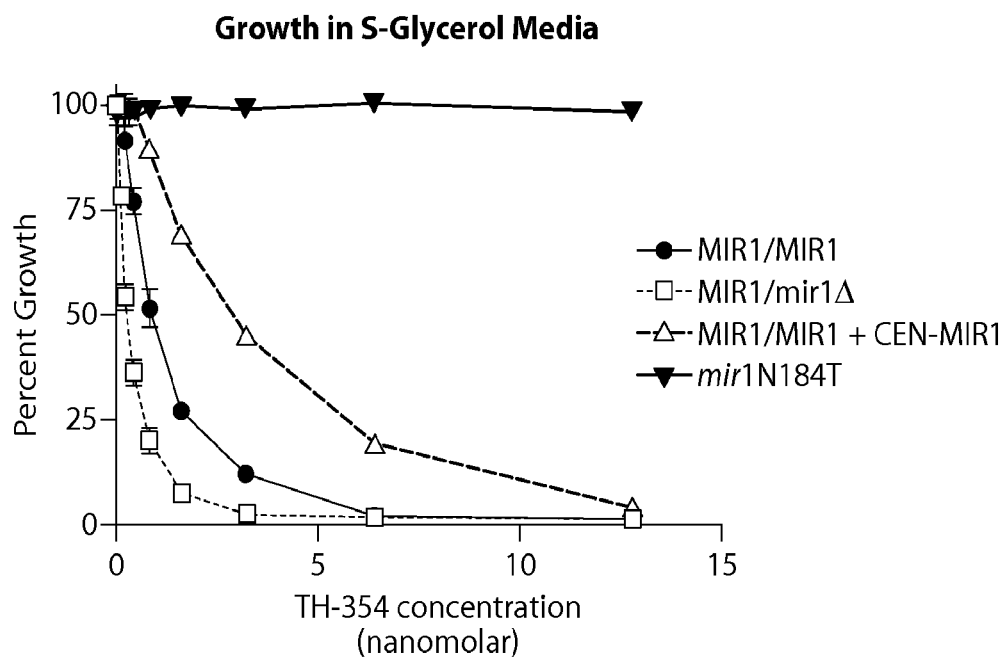
FIG. 11 shows an alignment of the MIR1 protein sequences from different yeast species and in human ("H. sapiens"). The resistant mutation is N184T in the listed yeast species and corresponds to a particular amino acid in the human protein. The mutation confers resistance to I-B-4 (ML316).
FIG. 12 shows the inhibitory activities of compound I-B-4 (ML316) against S. cerevisiae strain BY4743 and several derived strains. Data is provided for cells containing MIR1/MIR1, MIR1/mir1Δ, MIR1/MIR1+CEN-MIR1, and the MIR1 resistant mutation N184T.

Whole genome sequence of ATCC 200950 and three I-B-4-resistant mutants was determined using Illumina HiSeq sequencing system. Sequences were aligned to C. albicans reference genome to identify unique mutations in resistant strains. FIG. 10 shows the results of the genome sequencing. FIG. 11 shows the protein sequence alignment of a region of MIR1 homologs from fungi and humans to highlight the N184T polymorphism.

The inhibitory activities of I-B-4 (ML316) on the growth of S. cerevisiae strain BY4743; BY4743+pRS316-MIR1; BY4743 MIR1Δ/+; BY4743+pRS316-MIR1N184T strains were performed in synthetic glycerol media with varying concentrations of I-B-4. Strains were grown in liquid media in 96-well plates. Growth was measured by OD600 after 3 days (see FIG. 12).

Figure 13:
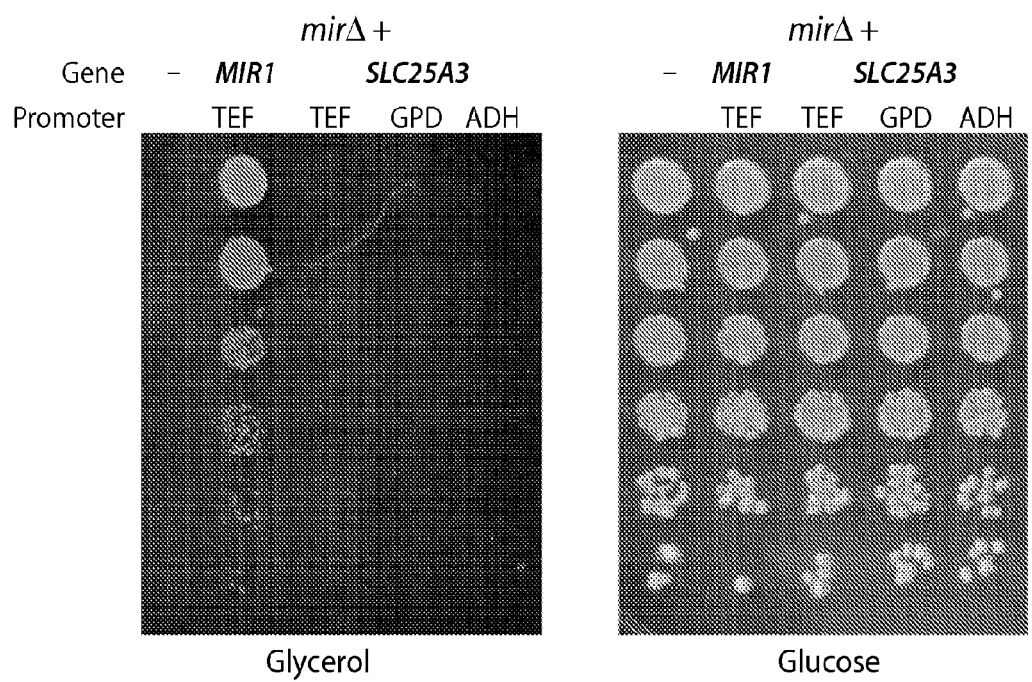
FIG. 13 shows the growth of untransformed and transformed S. cerevisiae mir1Δ+ cells in both glycerol and glucose media. The mutant cells were transformed with either the MIR1 (under the control of a TEF promoter) or the human SLC25A3 gene (under either the control of a TEF, GPD, or ADH promoter).

The growth of untransformed and transformed S. cerevisiae mir1Δ+ cells in both glycerol and glucose media was conducted. BY4741 mir1Δ was transformed with empty pRS316 vector or pRS316 vector containing S. cerevisiae MIR1 under the TEF promoter, or human homolog SLC25A3 under the TEF, GPD, or ADH promoters. Strains were grown on solid agar yeast synthetic media containing 2% glucose or 2% glycerol (FIG. 13).

Figure 14:
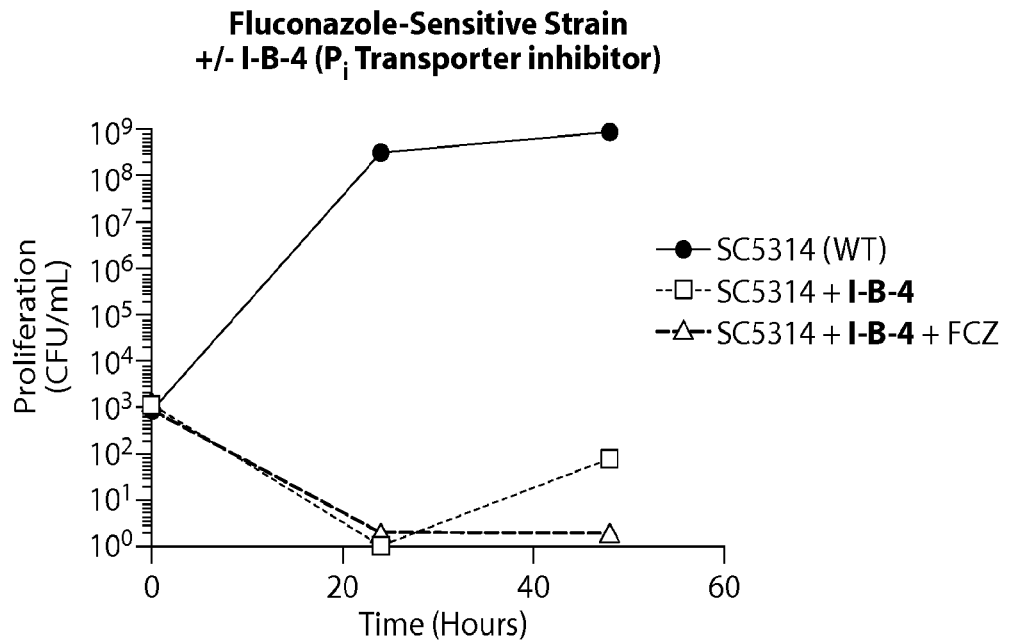
FIG. 14 shows that compound I-B-4 (ML316) and a combination of I-B-4 (ML316) and fluconazole (FCZ) were cytotoxic to fluconazole-sensitive Candida albicans strain SC5314 (WT: wild type).

Compound I-B-4 (ML316) was studied in fluconazole-sensitive Candida albicans strain SC5314. The SC5314 strain was inoculated into RPMI media at 10^3 CFU/mL in the presence or absence of 5 µM I-B-4 (ML316) and 32 ug/mL fluconazole. Colonies were plated from the cultures after 24 and 48 hours and counted. FIG. 14 shows the cell proliferation data over time.

Figure 15:
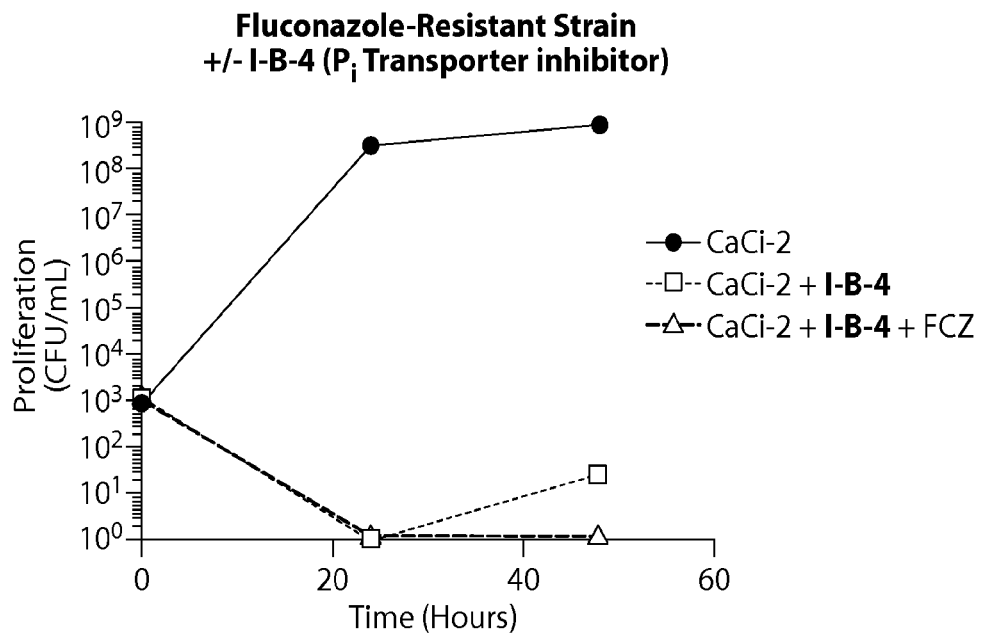
FIG. 15 shows that compound I-B-4 (ML316) and a combination of I-B-4 (ML316) and fluconazole (FCZ) were cytotoxic to fluconazole-resistant Candida albicans strain CaCi-2.

Compound I-B-4 (ML316) was also studied in fluconazole-sensitive *Candida albicans* CaCi-2. The CaCi-2 strain was inoculated into RPMI media at 10^3 CFU/mL in the presence or absence of 5 μM I-B-4 (ML316) and 32 ug/mL fluconazole. Colonies were plated from the cultures after 24 and 48 hours and counted. FIG. 15 shows the cell proliferation data over time.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive termsfrom one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein.

The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. An inhibitor of fungal or protozoan mitochondrial phosphate carrier protein Formula (I):

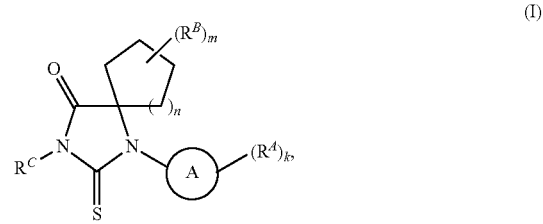

or a pharmaceutically acceptable salt thereof, wherein:

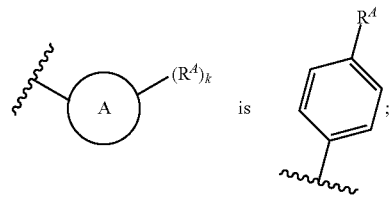

$R^A$ is halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{A1}$, —N(R$^{A1}$)$_2$, —SR$^{A1}$, —CN, —SCN, —C(=NR$^{A1}$)R$^{A1}$, —C(=NR$^{A1}$)OR$^{A1}$, —C(=NR$^{A1}$)N(R$^{A1}$)$_2$, —C(=O)R$^{A1}$, —C(=O)OR$^{A1}$, —C(=O)N(R$^{A1}$)$_2$, —NO$_2$, —NR$^{A1}$C(=O)R$^{A1}$, —NR$^{A1}$C(=O)OR$^{A1}$, —NR$^{A1}$C(=O)N(R$^{A1}$)$_2$, —OC(=O)R$^{A1}$, —OC(=O)OR$^{A1}$, —OC(=O)N(R$^{A1}$)$_2$, or a nitrogen protecting group when attached to a nitrogen atom;

each instance of $R^{A1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom;

m is 0;

n is 1 or 2;

$R^C$ is —C(=O)R$^{C1}$, —C(=O)OR$^{C1}$, —C(=O)N(R$^{C1}$)$_2$, —S(=O)$_2$R$^{C1}$, —S(=O)$_2$OR$^{C1}$, or —S(=O)$_2$N(R$^{C1}$)$_2$; and each instance of $R^{C1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or an oxygen protecting group when attached to an oxygen atom;

provided that the Compound of Formula (I) is not

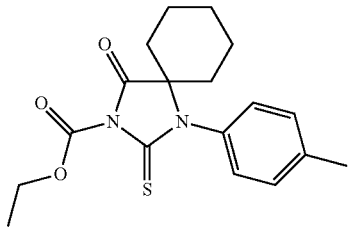

or

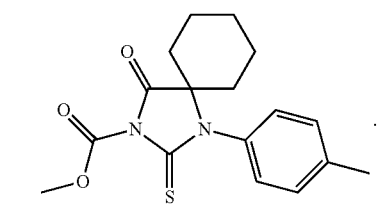

2. The compound of claim 1, or a pharmaceutically acceptable salt thereof, wherein $R^4$ is halogen, substituted or unsubstituted alkyl, substituted or unsubstituted aryl, —$OR^{41}$, or —CN.

3. The compound of claim 1, or a pharmaceutically acceptable salt thereof, wherein n is 1.

4. The compound of claim 1, or a pharmaceutically acceptable salt thereof, wherein n is 2.

5. The compound of claim 1, wherein the compound is of the formula:

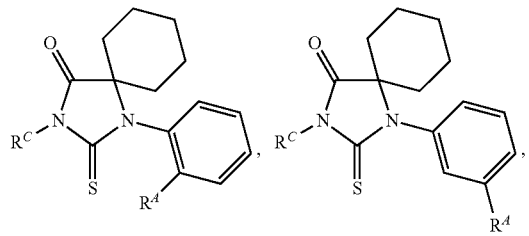

or a pharmaceutically acceptable salt thereof.

6. The compound of claim 1, wherein the compound is of the formula:

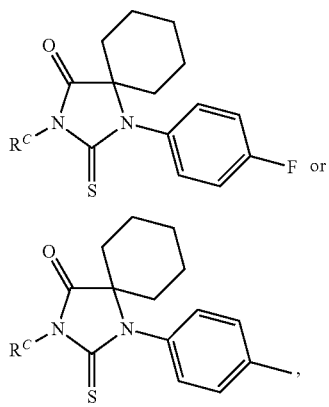

or a pharmaceutically acceptable salt thereof.

7. The compound of claim 1, wherein the compound is of the formula:

(I-A-3)

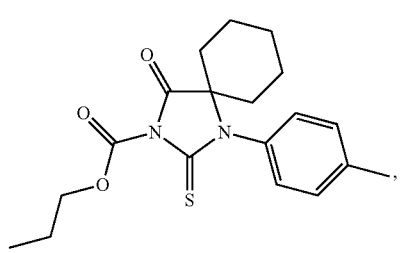

(I-A-4)

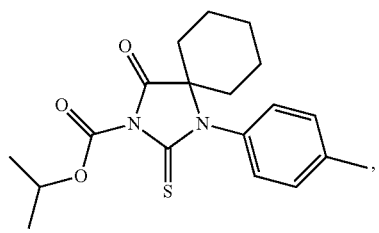

(I-A-5)

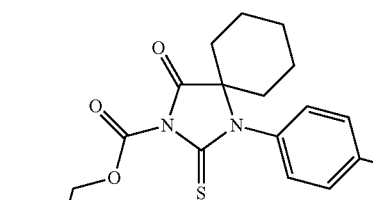

(I-A-6)

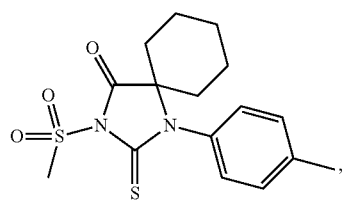
(I-A-7)

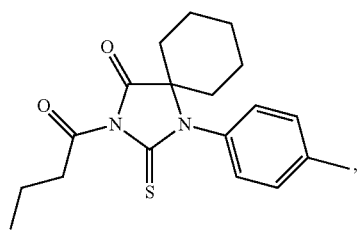
(I-A-8)

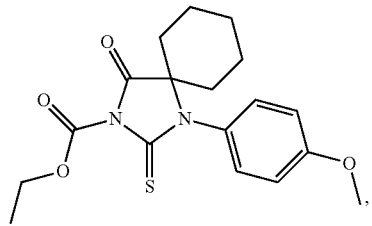
(I-B-3)

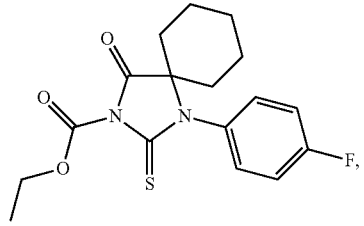
(I-B-4)

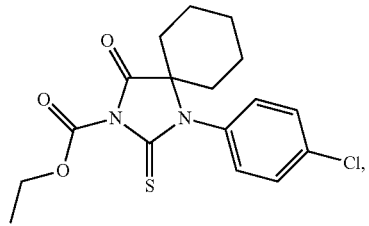
(I-B-5)

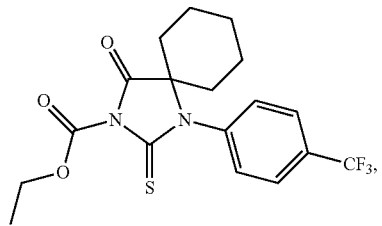
(I-B-6)

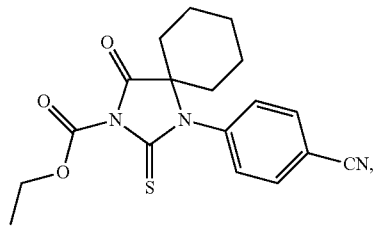
(I-B-7)

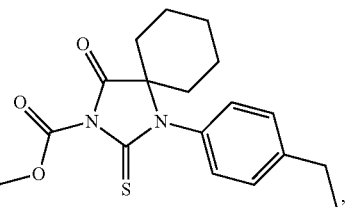
(I-B-10)

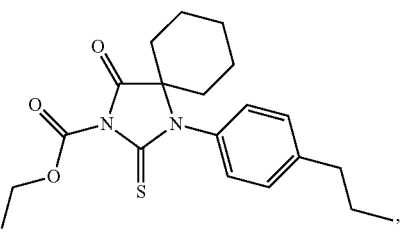
(I-B-11)

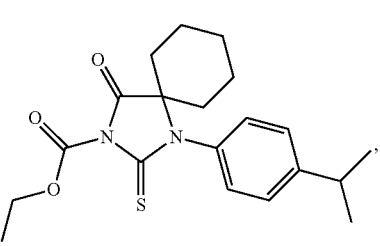
(I-B-12)

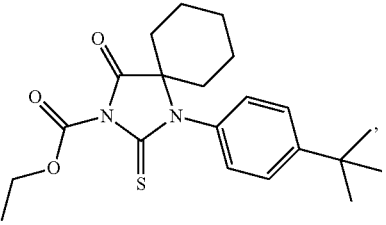
(I-B-13)

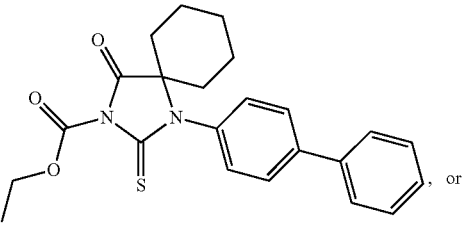
(I-B-14)

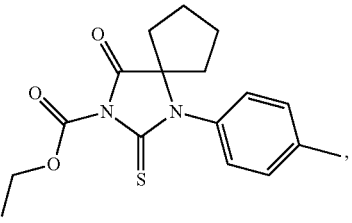
, or (I-C-3)

or a pharmaceutically acceptable salt thereof.

8. A pharmaceutical composition comprising a compound of claim 1, or a pharmaceutically acceptable salt thereof, and optionally a pharmaceutically acceptable excipient.

9. The compound of claim 1, or a pharmaceutically acceptable salt thereof, wherein $R^A$ is F, Cl, Br, —CH$_2$F, —CHF$_2$, —CF$_3$, Me, Et, Pr, Bu, Ph, —OMe, —OEt, —OPr, —OBu, or —CN.

10. The compound of claim 1, or a pharmaceutically acceptable salt thereof, wherein $R^A$ is F, Cl, or —CN.

11. The compound of claim 1, or a pharmaceutically acceptable salt thereof, wherein $R^A$ is F.

12. The compound of claim 1, or a pharmaceutically acceptable salt thereof, wherein $R^{A1}$ is hydrogen, substituted or unsubstituted alkyl, substituted or unsubstituted alkenyl, substituted or unsubstituted alkynyl, or an oxygen protecting group.

13. The compound of claim 1, or a pharmaceutically acceptable salt thereof, wherein $R^C$ is —C(=O)Me, —C(=O)Et, —C(=O)Pr, —C(=O)Bu, —C(=O)OMe, —C(=O)OEt, —C(=O)OPr, —C(=O)OBu, —C(=O)OBn, —C(=O)OPh, —C(=O)NH$_2$, —C(=O)NHMe, —C(=O)N(Me)$_2$, —S(=O)$_2$Me, —S(=O)$_2$CF$_3$, —S(=O)$_2$OMe, —S(=O)$_2$OEt, —S(=O)$_2$NH$_2$, —S(=O)$_2$NHMe, or —S(=O)$_2$N(Me)$_2$.

14. The compound of claim 1, or a pharmaceutically acceptable salt thereof, wherein $R^C$ is —C(=O)OMe, —C(=O)OEt, or —C(=O)OPr.

15. The compound of claim 1, or a pharmaceutically acceptable salt thereof, wherein $R^C$ is —C(=O)OEt.

16. The compound of claim 1, wherein the compound is of the formula:

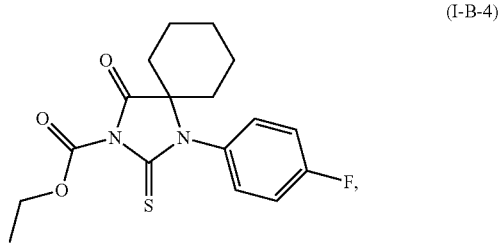 [SMILES: CCOC(=O)N1C(=O)C2(CCCCC2)N(c2ccc(F)cc2)C1=S]

(I-B-4)

or a pharmaceutically acceptable salt thereof.

\* \* \* \* \*